US008663915B2

(12) United States Patent
Miller et al.

(10) Patent No.: US 8,663,915 B2
(45) Date of Patent: Mar. 4, 2014

(54) METHODS OF CONTROLLING TUMORIGENESIS AND DIAGNOSING THE RISK THEREOF

(75) Inventors: Lance D. Miller, Singapore (SG); Bing Lim, Singapore (SG); Jinqiu Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 879 days.

(21) Appl. No.: 12/595,824

(22) PCT Filed: Apr. 11, 2008

(86) PCT No.: PCT/SG2008/000116
§ 371 (c)(1),
(2), (4) Date: Mar. 25, 2010

(87) PCT Pub. No.: WO2008/127199
PCT Pub. Date: Oct. 23, 2008

(65) Prior Publication Data
US 2012/0269732 A1    Oct. 25, 2012

Related U.S. Application Data

(60) Provisional application No. 60/911,573, filed on Apr. 13, 2007.

(51) Int. Cl.
*C12Q 1/68* (2006.01)
(52) U.S. Cl.
USPC .............................. 435/6; 435/325; 435/375
(58) Field of Classification Search
None
See application file for complete search history.

(56) References Cited

U.S. PATENT DOCUMENTS

| | | | |
|---|---|---|---|
| 5,217,999 A | 6/1993 | Levitzki et al. | |
| 5,302,606 A | 4/1994 | Spada et al. | |
| 5,330,992 A | 7/1994 | Eissenstat et al. | |
| 6,107,048 A | 8/2000 | Goldenring et al. | |
| 6,740,665 B1 | 5/2004 | Murali et al. | |
| 6,906,093 B2 | 6/2005 | Tang et al. | |
| 8,053,183 B2 * | 11/2011 | Nakamura et al. | 435/6.14 |
| 2005/0191618 A1 | 9/2005 | McSwiggen et al. | |
| 2007/0066616 A1 | 3/2007 | Shapiro et al. | |

FOREIGN PATENT DOCUMENTS

| | | |
|---|---|---|
| EP | 0 566 266 | 10/1993 |
| WO | WO-91/15495 | 10/1991 |
| WO | WO-92/20642 | 11/1992 |
| WO | WO-92/21660 | 12/1992 |
| WO | WO-94/03427 | 2/1994 |
| WO | WO-94/14808 | 7/1994 |
| WO | WO-96/18738 | 6/1996 |
| WO | WO-96/23879 | 8/1996 |
| WO | WO-01/04144 | 1/2001 |
| WO | WO-01/20022 | 3/2001 |
| WO | WO-01/92655 | 12/2001 |
| WO | WO-03/029462 | 4/2003 |
| WO | WO-03/035621 | 5/2003 |
| WO | WO-2004/005923 | 1/2004 |
| WO | WO-2004/015130 | 2/2004 |
| WO | WO-2005/019254 | 3/2005 |
| WO | WO-2005/019255 | 3/2005 |
| WO | WO-2005/019256 | 3/2005 |
| WO | WO-2007/082542 | 7/2007 |
| WO | WO-2007/147067 | 12/2007 |

OTHER PUBLICATIONS

International Search Report dated Apr. 22, 2010 for EP Application No. 08724378.8.
Melchor et al., Genomic analysis of the 8p11-12 amplicon in familial breast cancer, Int. J. Cancer: 120, 714-717 (2006).
Zhang et al, Oncogene triangulation through clinical and genomic intersect identification and functional validation of RAB11FLP1 as a new breast cancer oncogene on the 8p11 amplicon, # 2450 Proceedings of the American Association for Cancer Research, vol. 48, p. 582 (2007).
Adnane et al, BEK and FLG, two receptors to members of the FGF family, are amplified in subsets of human breast cancers, Oncogene (1991), 6(4):659-663.
Cheng et al, Assay of Rab25 function in ovarian and breast cancers, Methods Enzymol (2005), 403:202-215.

(Continued)

*Primary Examiner* — Kimberly Chong
(74) *Attorney, Agent, or Firm* — Blakely, Sokoloff, Taylor & Zafman LLP

(57) ABSTRACT

The present invention relates to methods of controlling tumorigenesis, including preventing, inhibiting, arresting or reversing tumorigenesis. The present invention also provides methods of treatment, prevention and diagnosis of neoblastoma, including cancer, such as metastatic cancer. In one method one or more cells having a predisposition to turn tumorigenic are identifyied. In the one or more cells an altered amount, an altered subcellular localisation or an altered activity of a Rab binding protein is detected. In a method of diagnosing the risk of developing a neoplasmt at least one of the expression level, the activity level and the subcellular localisation of a Rab binding protein is determined. In an in-vitro method of identifying a compound capable of forming a complex with a Rab binding protein the components that form the respective complex are contacted with each other. In a method of determining whether a neoplasm is sensitive to an alteration of intracellular calcium levels, at least one of the expression and the activity of a Rab binding protein is determined. An altered expression or an altered activity of the Rab binding protein is an indication that the neoplasm is sensitive to an alteration of intracellular calcium levels.

9 Claims, 27 Drawing Sheets

(56) References Cited

OTHER PUBLICATIONS

Hansen et al, Seocalcitol (EB 1089): a vitamin D analogue of anti-cancer potential. Background, design, synthesis, pre-clinical and clinical evaluation, Curr Pharm Des (2000), 6:803-828.
Rippe et al, Techniques to measure nucleic acid-protein binding and specificity. Nuclear extract preparations, DNase I footprinting, and mobility shift assays, Methods Mol Biol (2001), 160:459-479.
Sergeev et al, 1,25-dihydroxyvitamin D3 triggers calcium mediated apoptosis, Vitamin D Endocrine System: Structural, Biological, Genetic and Clinical Aspects (2000), pp. 399-402.
Streicher et al, Transforming function of the LSM1 oncogene in human breast cancers with the 8p11-12 amplicon, Oncogene (2007), 26(14):2104-2114.
Velazquez-Campoy et al, Characterization of protein-protein interactions by isothermal titration calorimetry, Methods Mol Biol (2004), 261:35-54.
Jones et al, Endocytic recycling pathways: emerging regulators of cell migration, Curr Opin Cell Biol (2006), 18(5):549-57.
Kubodera, Search for development of active vitamin D3 analogs, Current Bioactiv Compounds (2006), 2(3):301-315.
Rechsteiner et al, PEST sequences and regulation by proteolysis, Trends Biochem Sci (1996), 21(7):267-271.
Vandewalle et al, Vitamin-D3 derivatives and breast-tumor cell growth: effect on intracellular calcium and apoptosis, Int J Cancer (1995), 61:806-811.
Adler et al, From description to causality: mechanisms of gene expression signatures in cancer, Cell Cycle (2006), 5(11):1148-1151.
Andre et al, Microtubule-associated protein-tau is a bifunctional predictor of endocrine sensitivity and chemotherapy resistance in estrogen receptor-positive breast cancer, Clin Cancer Res (2007), 13(7):2061-2067.
Balsara et al, Comparative genomic hybridization analysis detects frequent, often high-level, overrepresentation of DNA sequences at 3q, 5q, 7p and 8q in human non-small cell lung carcinomas, Cancer Res. (1997), 57(11):2116-2120.
Baudet et al, Cytotoxic effects of $1\alpha$,25-dihydroxyvitamin D3 and synthetic vitamin D3 analogues on a glioma cell line, Cancer Lett (1996), 100:3-10.
Beste et al, Small antibody-like proteins with prescribed ligand specificities derived from the lipocalin fold, PNAS (1999), 96:1898-1903.
Cheng et al, The RAB25 small GTPase determines aggressiveness of ovarian and breast cancers, Nat Med (2004), 10(11):1251-1256.
Chin et al, Genomic and transcriptional aberrations linked to breast cancer pathophysiologies, Cancer Cell (2006), 10:529-541.
Colston et al, EB1089: a new vitamin D analogue that inhibits the growth of breast cancer cells in vivo and in vitro, Biochem Pharmacol (1992), 44:2273-2280.
Costa, Non-coding RNAs: new players in eukaryotic biology, Gene (2005), 357(2):83-94.
Cuny et al, Relating genotype and phenotype in breast cancer: an analysis of the prognostic significance of amplification at eight different genes or loci and of p53 mutations, Cancer Res (2000), 60:1077-1083.
Dai et al, A cell proliferation signature is a marker of extremely poor outcome in a subpopulation of breast cancer patients, Cancer Res (2005), 65(10):4059-4066.
Demasters et al, Potentiation of radiation sensitivity in breast tumor cells by the vitamin D3 analogue, EB 1089, through promotion of autophagy and interference with proliferative recovery, Mol Cancer Ther (2006), 5(11):2786-2797.
Dice, Molecular determinants of protein half-lives in eukaryotic cells, FASEB J (1987), 1(5):349-357.
Douglas et al, Array comparative genomic hybridization analysis of colorectal cancer cell lines and primary carcinomas, Cancer Res (2004), 64:4817-4825.
Ducharme et al, MARK2/EMK1/Par-$1b\alpha$ Phosphorylation of Rab11-Family Interacting Protein 2 is Necessary for the Timely Establishment of Polarity in Madin-Darby Canine Kidney Cells, Mol Biol Cell (2006), 17(8):3625-3637.
Fukuda et al, Slac2-a/melanophilin contains multiple PEST-like sequences that are highly sensitive to proteolysis, J Biol Chem (2004), 279(21):22314-22321.
Garcia et al, a 1Mb minimal amplicon at 8pll-12 in breast cancer identifies new candidate oncogenes, Oncogene (2005), 24:5235-5245.
Gebhardt et al, c-Fos-dependent induction of the small ras-related GTPase Rab11a in skin carcinogenesis, Am J Pathol (2005), 167:243-253.
Gelsi-Boyer et al, Comprehensive profiling of 8p11-12 amplification in breast cancer, Mol Cancer Res (2005), 3(12):655-667.
Gill et al, Biopharmaceutical drug discovery using novel protein scaffolds, Curr Opin Biotechnol (2006), 17(6):653-658.
Goldenring et al, Rab11 in dysplasia of Barrett's epithelia, Yale J Biol Med (1999), 72:113-120.
Hales et al, Identification and Characterization of a Family of Rab11-interacting Proteins, J Biol Chem (2001), 276(42):39067-39075.
Holt et al, Domain antibodies: proteins for therapy, Trends Biotechnol (2003), 21(11):484-90.
Horgan et al, Rab11-FIP3 Is Critical for the Structural Integrity of the Endosomal Recycling Compartment, Traffic (2007), 8:414-430.
Hsieh et al, Induction of apoptosis and altered nuclear/cytoplasmic distribution of the androgen receptor and prostate-specific antigen by $1\alpha,25$-dihydroxyvitamin $D_3$ in androgen-responsive LNCaP cells, Biochem Biophys Res Commun (1997), 235:539-544.
Illiades et al, Triabodies: single chain Fv fragments without a linker form trivalent trimers, FEBS Lett 1997, 409(3):437-441.
International Preliminary Report on Patentability dated Jun. 23, 2009 for PCT Application No. PCT/SG2008/000116.
International Search Report and the Written Opinion dated Jun. 16, 2008 for PCT Application No. PCT/SG2008/000116.
Ishihara et al, Activation of calpain precedes morphological alterations during hydrogen peroxide-induced apoptosis in neuronally differentiated mouse embryonal carcinoma P19 cell line, Neurosci Lett (2000), 279:97-100.
Ishiwata et al, Establishment and characterization of HEPFT, a cell line derived from hepatoid carcinoma of the fallopian tube, with special reference to alpha-fetoprotein, lectin affinity and histogenesis, Human Cell (2007), 20:119-130.
Ivshina et al, Genetic reclassification of histologic grade delineates new clinical subtypes of breast cancer, Cancer Res (2006), 66(21):10292-10301.
James et al, Leukemia cell differentiation: cellular and molecular interactions of retinoids and vitamin D, Gen Pharmacol (1999), 32(1):143-154.
Kim et al, Genome-Wide Screening of Genomic Alterations and Their Clinicopathologic Implications in Non-Small Cell Lung Cancers, Clin Cancer Res (2005), 11(23):8235-8242.
Kluger et al, Spectral biclustering of microarray data: coclustering genes and conditions, Genome Res (2003), 13(4):703-716.
Kwon et al, Quantitative Evaluation of the Relative Cell Permeability of Peptoids and Peptides. J Am Chem Soc (2007), 129(6):1508-1509.
Lee et al, Activation of bone morphogenetic protein signaling by a Gemini vitamin $D_3$ analogue is mediated by Ras/protein kinase $C\alpha$, Cancer Res (2007), 67(24):11840-11847.
Letessier et al, Frequency, prognostic impact, and subtype association of 8p12, 8q24, 11q13, 12q13, 17q12, and 20q13 amplifications in breast cancers, BMC Cancer (2006), 6(245):1-13.
LIN, piRNAs in the germ line, Science (2007), 316:397.
Lindsay et al, Rab coupling protein (RCP), a novel Rab4 and Rab11 effector protein, J Biol Chem (2002), 277(14):12190-12199.
Loi et al, Definition of clinically distinct molecular subtypes in estrogen receptor-positive breast carcinomas through genomic grade, J Clin Oncol (2007), 25(10):1239-1246.
Marie et al, Rab coupling protein is selectively degraded by calpain in a Ca2+-dependent manner, Biochem J (2005), 389:223-231.
Mathiasen et al, Apoptosis Induced by Vitamin D Compounds in Breast Cancer Cells is Inhibited by Bcl-2 but Does Not Involve Known Caspases or P531, Cancer Res (1999), 59:4848-4856.
Mathiasen et al, Calcium and calpain as key mediators of apoptosis-like death induced by vitamin D compounds in breast cancer cells, J Biol Chem (2002), 277(34):30738-30745.

(56) References Cited

OTHER PUBLICATIONS

Mathiasen et al, EB 1089, a novel vitamin D analogue, has strong antiproliferative and differentiation inducing effects on cancer cells, J Steroid Biochem Mol Biol (1993), 46:365-371.
Miller et al, An expression signature for p53 status in human breast cancer predicts mutation status, transcriptional effects, and patient survival, PNAS (2005), 102(38):13550-13555.
Mosavi et al, The ankyrin repeat as molecular architecture for protein recognition, Protein Science (2004), 13:1435-1448.
Nakagawa et al, Cross-talk between two cysteine protease families. Activation of caspase-12 by calpain in apoptosis, J Cell Biol (2000), 150:887-894.
Nakao et al, High-resolution analysis of DNA copy number alterations in colorectal cancer by array-based comparative genomic hybridization, Carcinogenesis (2004), 25(8):1345-1357.
Ono et al, Systematic solution-phase parallel synthesis of active vitamin D3 analogs with elongated side chains and their cell differentiation activities, J Comb Chem (2007), 9(4):711-716.
Pawitan et al, Gene expression profiling spares early breast cancer patients from adjuvant therapy: derived and validated in two population-based cohorts, Breast Cancer Res (2005), 7(6):R953-964.
Peden et al, The RCP-Rab11 Complex Regulates Endocytic Protein Sorting, Mol Biol Cell (2004), 15:3530-3541.
Perou et al, Molecular portraits of human breast tumours, Nature (2000), 406(6797):747-752.
Pole et al, High-resolution analysis of chromosome rearrangements on 8p in breast, colon and pancreatic cancer reveals a complex pattern of loss, gain and translocation, Oncogene (2006), 25:5693-5706.
Pollack et al, Microarray analysis reveals a major direct role of DNA copy number alteration in the transcriptional program of human breast tumors, PNAS (2002), 99(20):12963-12968.
Posner et al, Difluoromethyl analogs of the natural hormone 1alpha,25-dihydroxyvitamin $D_3$: Design, synthesis, and preliminary biological evaluation, J Steroid Biochem Mol Biol (2007), 103:213-221.
Powelka et al, Stimulation-Dependent Recycling of Integrin β1 Regulated by ARF6 and Rab11, Traffic (2004), 5:20-36.
Ray et al, Genomic and expression analysis of the 8p11-12 amplicon in human breast cancer cell lines, Cancer Res (2004), 64:40-47.
Ray et al, Oxidative Stress and Ca2 influx upregulate calpain and induce apoptosis in PC12 cells, Brain Res (2000), 852:326-334.
Reyal et al, Visualizing chromosomes as transcriptome correlation maps: evidence of chromosomal domains containing co-expressed genes—a study of 130 invasive ductal breast carcinomas, Cancer Res (2005), 65(4):1376-1383.
Reynolds et al, Rational siRNA design for RNA interference, Nat Biotechnol (2004), 22(3):326-330.
Rosenwald et al, The proliferation gene expression signature is a quantitative integrator of oncogenic events that predicts survival in mantle cell lymphoma, Cancer Cell (2003), 3(2):185-197.
Runnebaum et al, p53 mutant His175 identified in a newly established fallopian tube carcinoma cell line secreting interleukin 6, FEBS Lett (1994), 353:29-32.
Sergeev et al, Regulation of intracellular calcium in human breast cancer cells, Endocrine (1998), 9(3):321-327.
Shimizu et al, Design and evaluation of new antipsoriatic antedrug candidates having 16-en-22-oxa-vitamin $D_3$ structures, Bioorg Med Chem Lett (2006), 16(12):3323-3329.

Shumway et al, The PEST domain of IκBα is necessary and sufficient for in vitro degradation by μ-calpain, J Biol Chem (1999), 274(43):30874-30881.
Silverman et al, Multivalent avimer proteins evolved by exon shuffling of a family of human receptor domains, Nat Biotechnol (2005), 23(12):1556-1561.
Simon et al, High-throughput tissue microarray analysis of 3p25 (RAF1) and 8p12 (FGFR1) copy number alterations in urinary bladder cancer, Cancer Res (2001), 61(11):4514-4519.
Skerra, Engineered protein scaffolds for molecular recognition, J Mol Recognit (2000), 13(4):167-187.
Snijders et al, Genome-wide-array-based comparative genomic hybridization reveals genetic homogeneity and frequent copy number increases encompassing CCNE1 in fallopian tube carcinoma, Oncogene (2003), 22(27):4281-4286.
Song et al, Antibody mediated in vivo delivery of small interfering RNAs via cell-surface receptors, Nature Biotech (2005), 23(6):709-717.
Steen et al, Analysis of protein-nucleic acid interactions by photochemical cross-linking and mass spectrometry, Mass Spectrom Rev (2002), 21(3):163-182.
Stone et al, The assembly of single domain antibodies into bispecific decavalent molecules, J Immunol Methods (2007), 318:88-94.
Theillet et al, FGFRI and PLAT genes and DNA amplification at 8p12 in breast and ovarian cancers, Genes Chromosomes Cancer (1993), 7:219-226.
Thompson et al, Recent advances in fluorescence correlation spectroscopy, Curr Opin Struct Biol (2002), 12(5):634-641.
Tompa et al, On the sequential determinants of calpain cleavage, J Biol Chem (2004), 279(20):20775-20785.
Tonon et al, High-resolution genomic profiles of human lung cancer, PNAS (2005), 102(27): 9625-9630.
Turk, Targeting proteases: successes, failures and future projects, Nat Rev Drug Discov (2006), 5(9):785-799.
Whitfield et al, Common markers of proliferation, Nat Rev Cancer (2006), 6(2):99-106.
Whitfield et al, Identification of Genes periodically Expressed in the Human Cell Cycle and Their Expression in Tumors, Mol Biol Cell (2002), 13:1977-2000.
Wojtkielewicz et al, Synthesis of γ-and δ-lactones from 1α-hydroxy-5,6-trans-vitamin $D_3$ by ring-closing metathesis route and their reduction with metal hydrides, Steroids (2007), 72(6-7):552-558.
Written Opinion of the International Preliminary Examining Authority dated Mar. 27, 2009 for PCT Application No. PCT/SG2008/000116.
Yaginuma et al, Genomic copy-number aberrations related to lymph-node metastasis of colon cancer, J Int Med Res (2006), 34(4):390-396.
Yang et al, Multiple interacting oncogenes on the 8p11-p12 amplicon in human breast cancer, Cancer Res (2006), 66(24):11632-11643.
Yoon et al, Hypoxia Stimulates Carcinoma Invasion by Stabilizing Microtubules and Promoting the Rab11 Trafficking of the α6B4 Integrin, Caner Res (2005), 65(7):2761-2769.
Yoon et al, Antileukemic effect of a synthetic vitamin D2 analog, HY-11, with low potential to cause hypercalcemia, International Journal of Oncology (2008), 23:387-396.
Zamore, et al; Ribo-gnome: the big world of small RNAs; Science (2005); 309:1519-1524.

* cited by examiner

Fig. 2

| characteristics | Uppsala n=251 | Stockholm n=159 | Belgium n=227 | Singapore n=100 |
|---|---|---|---|---|
| Age (years) | | | | |
| Median | 64 | 56 | 61 | 51 |
| Range | 28-93 | 31-87 | 24-86 | 29-86 |
| Tumor Size | | | | |
| <2 cm | 112 (45%) | 64 (40%) | 86 (38%) | 16 (16%) |
| 2-3 cm | 101 (40%) | 71 (45%) | 93 (41%) | 47 (47%) |
| >3 cm | 38 (15%) | 22 (14%) | 48 (21%) | 35 (35%) |
| Unknown | 0 (0%) | 2 (1%) | 0 (0%) | 2 (2%) |
| Histologic Grade | | | | |
| Grade 1 | 67 (27%) | 28 (18%) | 34 (15%) | 11 (11%) |
| Grade 2 | 127 (51%) | 58 (36%) | 91 (40%) | 40 (40%) |
| Grade 3 | 55 (22%) | 61 (38%) | 60 (26%) | 47 (47%) |
| Unknown | 2 (0.8%) | 12 (8%) | 42 (19%) | 2 (2%) |
| Lymph Node Status | | | | |
| Positive | 82 (33%) | 60 (38%) | 38 (17%) | 45 (45%) |
| Negative | 160 (64%) | 94 (59%) | 183 (81%) | 53 (53%) |
| Unknown | 9 (4%) | 5 (3%) | 6 (3%) | 2 (2%) |
| ER Status | | | | |
| Positive | 213 (85%) | 130 (82%) | 171 (75%) | 61 (61%) |
| Negative | 34 (14%) | 29 (18%) | 48 (21%) | 36 (36%) |
| Unknown | 4 (2%) | 0 (0%) | 8 (4%) | 3 (3%) |
| Metastasis within 5 years | | | | |
| Yes | 42 (17%) | 26 (16%) | 43 (19%) | 15 (15%) |
| No | 183 (73%) | 121 (76%) | 135 (59%) | 35 (35%) |
| Censored | 26 (10%) | 12 (8%) | 49 (22%) | 50 (50%) |
| Treatment | | | | |
| No Systemic Therapy | 143 (57%) | 33 (21%) | 77 (34%) | 10 (10%) |
| Endocrine | 80 (32%) | 96 (60%) | 109 (48%) | 23 (23%) |
| Chemo | 24 (10%) | 12 (8%) | 41 (18%) | 30 (30%) |
| Endocrine & Chemo | 4 (2%) | 18 (11%) | 0 (0%) | 15 (15%) |
| Unknown | 0 (0%) | 0 (0%) | 0 (0%) | 22 (22%) |

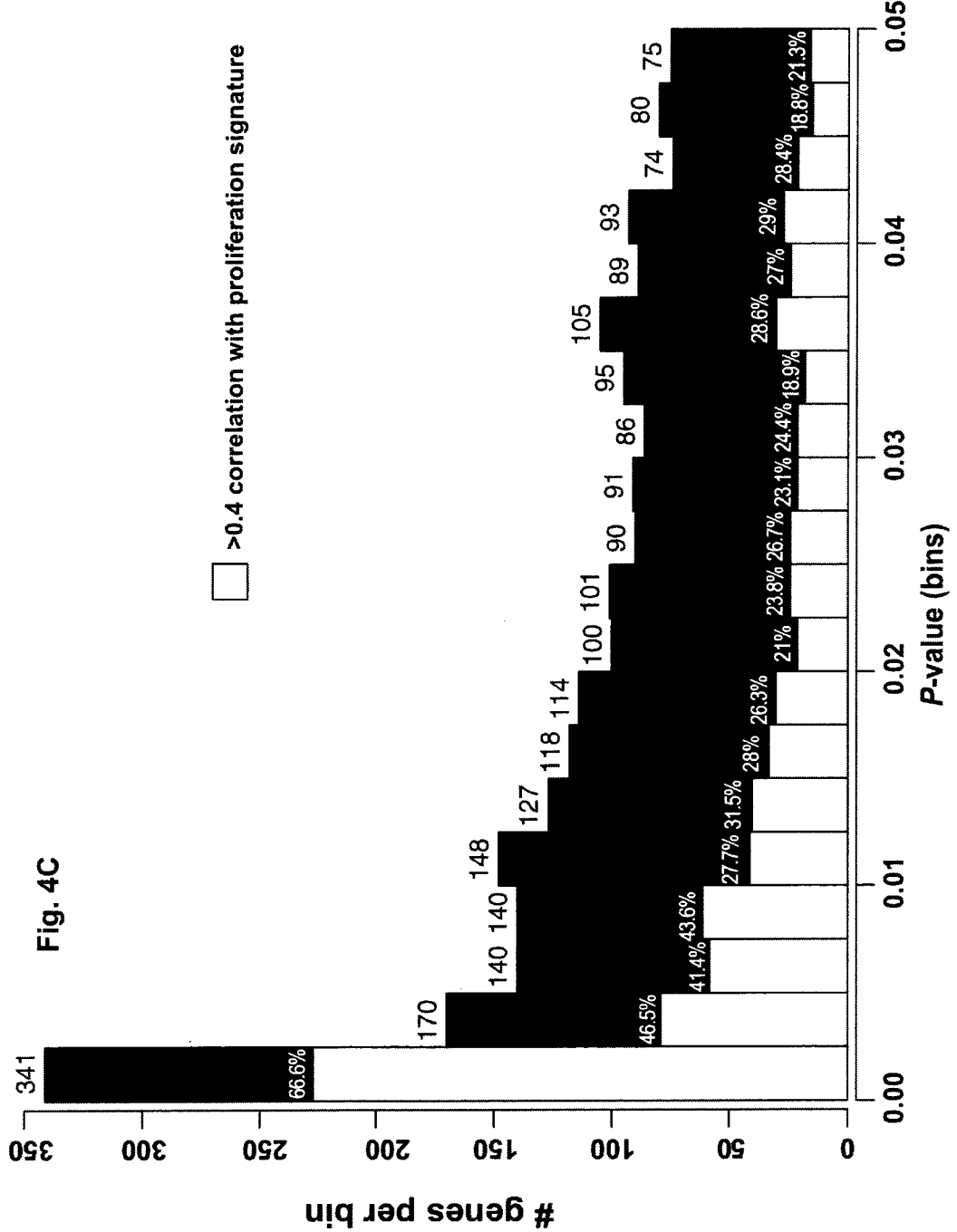

Fig. 5
A Chromosome 17q12 PEA
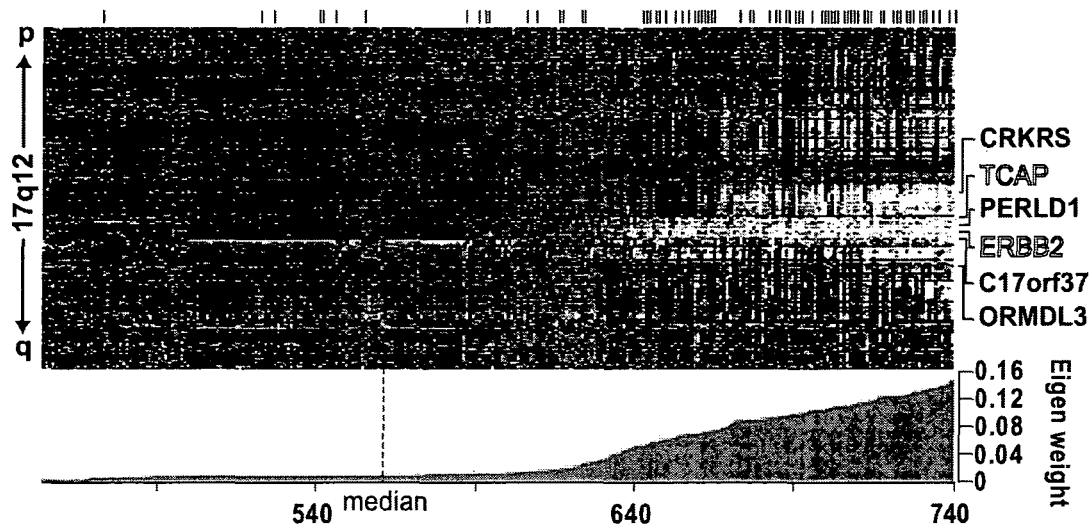
B Chromosome 8p11-12 PEA
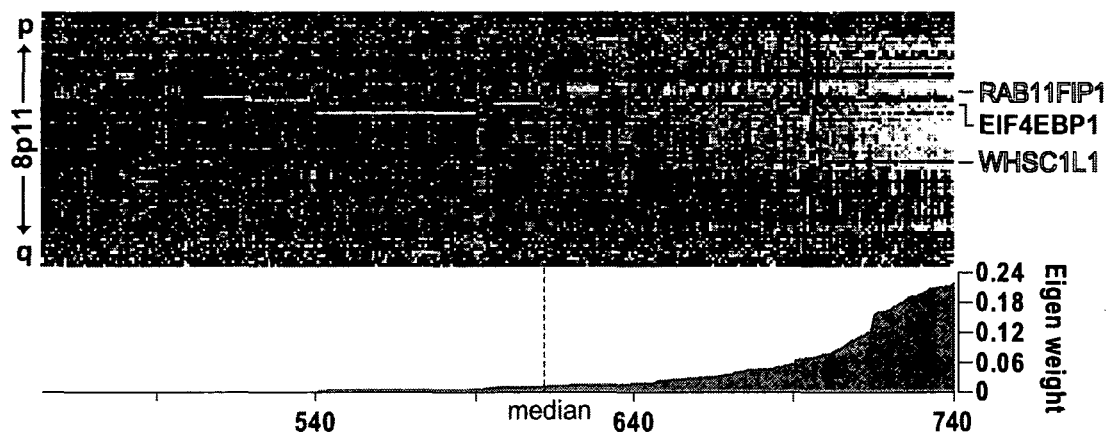

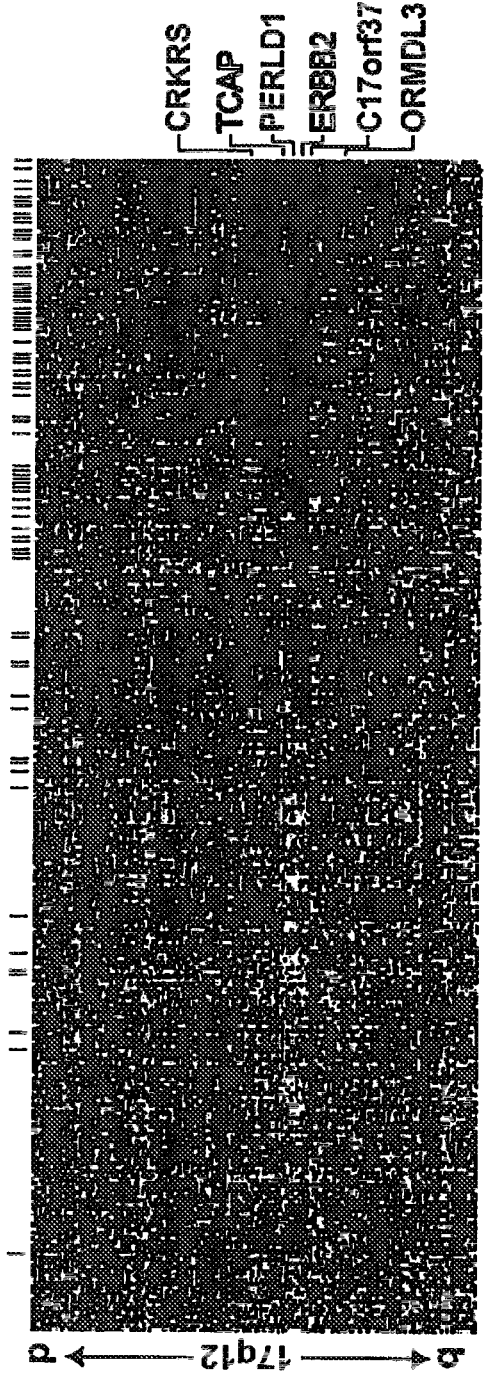
Fig. 5C Chromosome 17q12 PEA
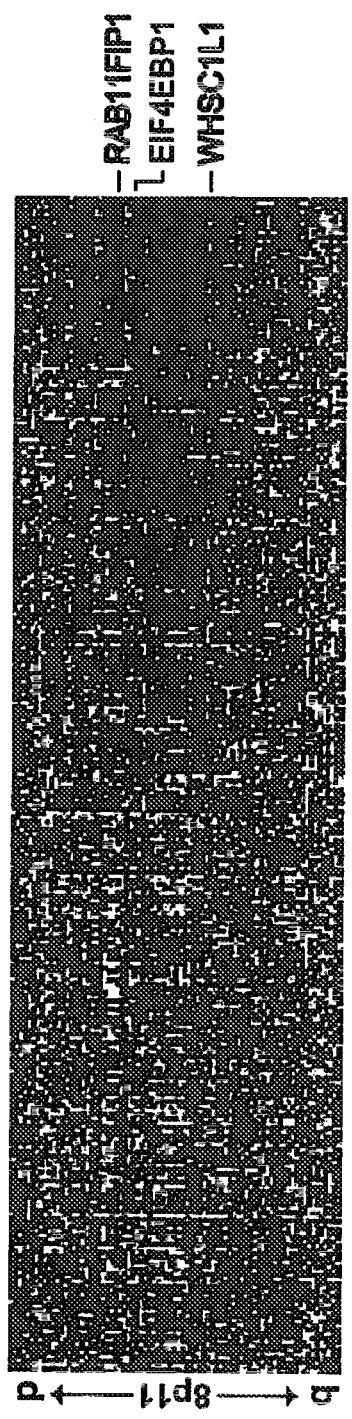
Fig. 5D Chromosome 8p11-12 PEA TRIAGE output:

| TRIAGE steps: | 2,3 | 4 | 5 | 6 |
|---|---|---|---|---|
| | unselected survival | selected survival | exp. rank | prolif. corr. |
| CRKRS | 0.006 | NS | 29 | 0.45* |
| TCAP | 0.004 | 0.038 | 19 | 0.20 |
| PERLD1 | 0.039 | NS | 12 | 0.17 |
| ERBB2 | 0.010 | 0.037 | 3 | 0.13 |
| C17orf37 | 0.006 | NS | 2 | 0.42* |
| ORMDL3 | 0.011 | NS | 14 | 0.18 |
| | unselected survival | selected survival | exp. rank | prolif. corr. |
| RAB11FIP1 | 0.0002 | 0.004 | 4 | 0.16 |
| EIF4EBP1 | 0.006 | NS | 13 | 0.58* |
| WHSC1L1 | 0.035 | 0.049 | 46 | 0.05 |

Fig. 6A    Endogenous Expression of RAB11-FIP1 (RCP)

Fig. 6D
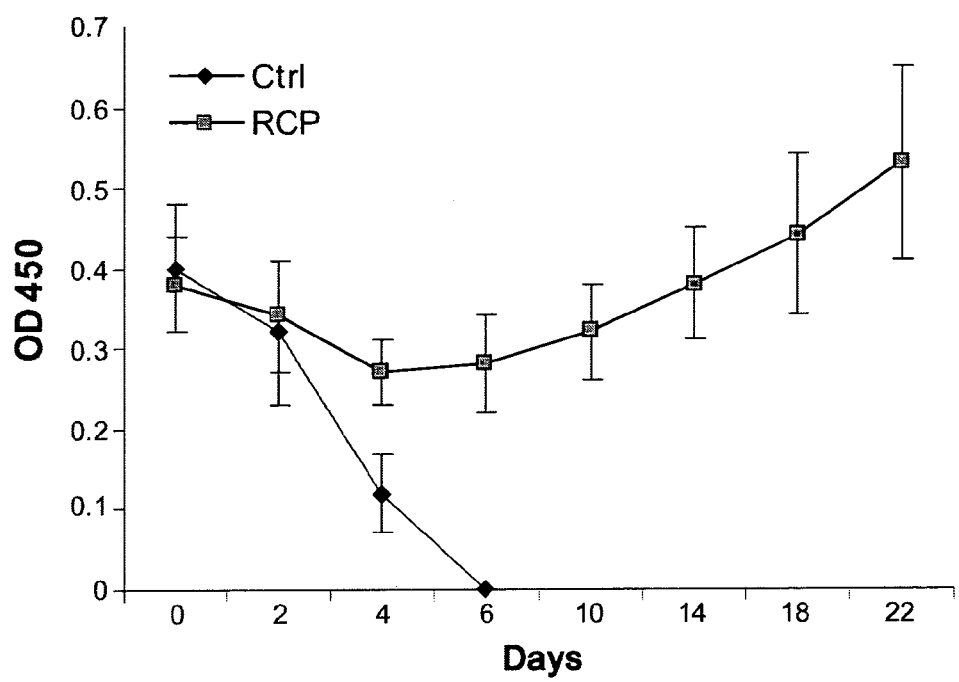
Fig. 6E Anchorage-Independent Growth
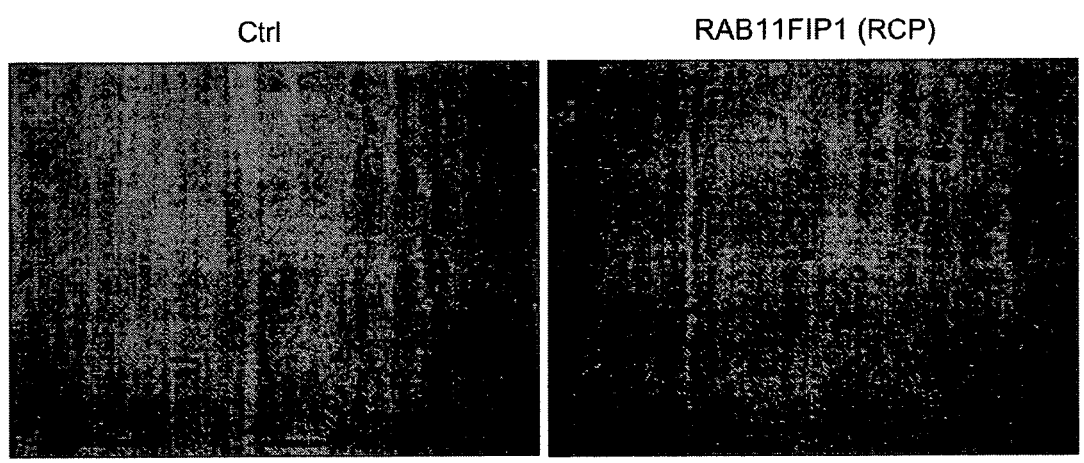

Fig. 9G *RCP expression in tumors*
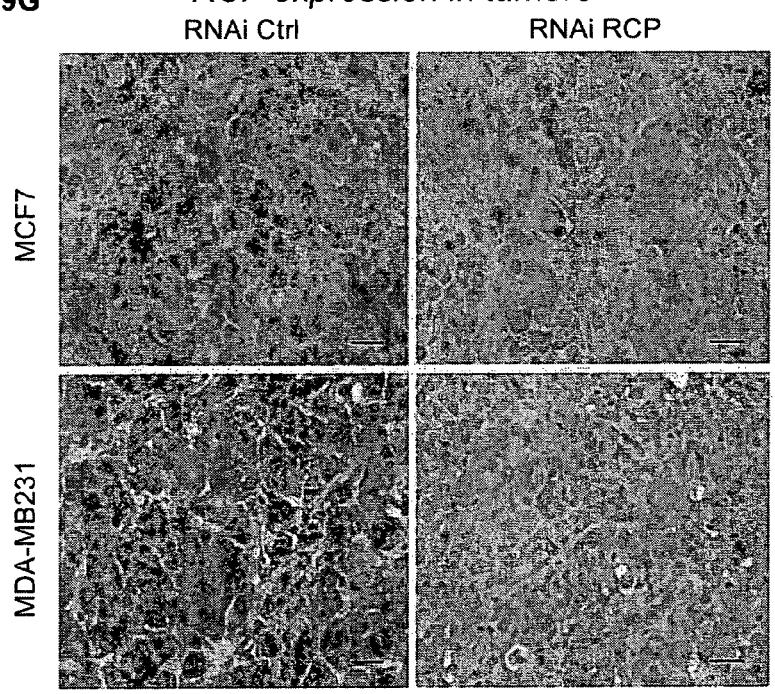
Fig. 9H *Apoptosis of MDA-MB231 cells*
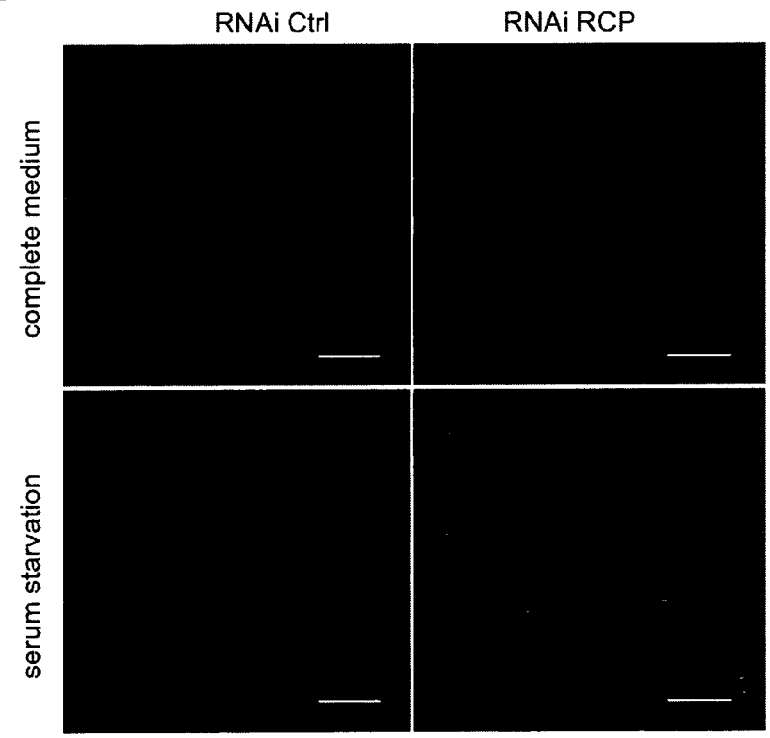

METHODS OF CONTROLLING TUMORIGENESIS AND DIAGNOSING THE RISK THEREOF

CROSS-REFERENCE TO RELATED APPLICATIONS

This application makes reference to and claims the benefit of priority of an application for "Preventing, inhibiting, arresting or reversing tumorigenesis by modulation of a rab binding protein and related uses of a rab binding protein" filed on Apr. 13, 2007 with the U.S. Patent and Trademark Office and there duly assigned Ser. No. 60/911,573. The content of said application filed on Apr. 13, 2007 is incorporated herein by reference for all purposes, including an incorporation of any element or part of the description, claims or drawings not contained herein and referred to in Rule 20.5(a) of the PCT, pursuant to Rule 4.18 of the PCT.

This application incorporates by referenced the material (Sequence Listing) in the ASCII text file called SequenceListing.txt, created Apr. 17, 2013, having a file size of 1.48 kilobytes.

FIELD OF THE INVENTION

The present invention relates to methods of controlling tumorigenesis and diagnosing the risk thereof. The methods rely on an altered amount and/or activity of a Rab binding protein. The invention also relates to methods of identifying a compound capable of forming a complex with a Rab binding protein, and of modulating the amount, the expression and/or the activity of a Rab binding protein. The invention also provides a method of determining whether a neoplasm is sensitive to an alteration of intracellular calcium levels.

BACKGROUND OF THE INVENTION

Cancer is a major cause of death worldwide, being the second-leading cause of death in developed countries, and even the number one cause of death in e.g. Australia, Japan, Korea, Singapore and the male population of the UK and Spain. The number of people who develop cancer each year is increasing. Nevertheless cancer therapy has not managed to decrease cancer mortality in the last three decades.

Autonomous cell growth resulting in tissue invasion and metastasis is the defining feature of all malignant neoplasms. Cancers do not necessarily arise solely as a result of an accelerated rate of cell proliferation. Rather they are the consequence of an imbalance between the rate of cell-cycle progression (cell division) and cell growth (cell mass) on one hand and programmed cell death (apoptosis) on the other.

Resolving the identity of the oncogenic drivers of tumorigenesis and metastatic growth is crucial not only for understanding the pathobiology of cancer, but also for treating patients, as such genes are increasingly being exploited for therapeutic benefit (Herceptin, Avastin, Gleevec). In human cancers, oncogenes are frequently activated by aberrant overexpression resulting from genomic amplification, sequence mutations or promoter hypomethylation. Chromosomal loci that are frequently amplified in cancer, known as amplicons, are thought to be driven by one or more oncogenes, and though many recurrent amplicons have been observed, their oncogenic determinants remain largely unknown. These loci have traditionally been interrogated by cytogenetics techniques such as comparative genomic hybridization (CGH) to assess the extent and frequency of copy number gains, and although this strategy has provided many gene candidates for consideration, the extensive size of the gene lists, together with a paucity of functional information, has limited progress towards oncogene discovery. More frequently, the discovery of oncogenes has been a slow and empirical process—depending mostly on the generation of hypotheses derived from cumulative observations of gene function in different experimental contexts.

It is an object of the present invention to provide means of controlling, including preventing tumorigenesis and of identifying a cell with a predisposition to turn tumorigenic.

SUMMARY OF THE INVENTION

In a first aspect the present invention provides methods of controlling tumorigenesis, including preventing, inhibiting, arresting or reversing tumorigenesis. The present invention also provides methods of treatment, prevention and diagnosis of neoblastoma, including cancer, such as metastatic cancer.

One such method includes modulating the amount or activity of a Rab binding protein, in particular of a Rab11FIP protein (Rab11 family-interacting protein).

A further method of the invention relates to identifying one or more cells having a predisposition to turn tumorigenic. This method includes detecting in the one or more cells an altered amount, an altered subcellular localisation or an altered activity of a Rab binding protein, in particular a Rab11FIP protein.

The invention also provides a method of diagnosing the risk of developing a neoplasm. This method includes determining at least one of the expression level, the activity level and the subcellular localisation of a Rab binding protein, in particular a Rab11FIP protein.

The application is also concerned with the identification of suitable compounds capable of modulating the activity of a Rab binding protein, in particular a Rab11FIP protein, and thereby for example of acting as anti-cancer agents.

In this regard the invention provides an in-vitro method of identifying a compound capable of forming a complex with a Rab binding protein, in particular a Rab11FIP protein. The method includes contacting the components that form the respective complex with each other.

In a further aspect the invention provides a method for identifying a compound capable of modulating the activity of a Rab binding protein, in particular a Rab11FIP protein, in vivo. The method includes providing a microorganism expressing the Rab binding protein or a functional fragment thereof. The method further includes adding a compound to the microorganism. The method also includes monitoring a change in cell phenotype or activity of a Rab binding protein.

In another aspect the invention provides methods of identifying a compound capable of modulating the amount or the activity of a Rab binding protein, in particular a Rab11FIP protein.

One such method includes providing a host organism. The host organism is capable of accommodating and growing a cancer cell. The method also includes introducing a cancer cell into the host organism. Furthermore the method includes administering a compound suspected to be capable of modulating the expression and/or the activity of a Rab binding protein. The method further includes monitoring the growth of any tumor (including a plurality thereof) in the host organism.

A further such method also includes providing a host organism. The host organism is capable of accommodating and growing a cancer cell. The method also includes introducing a cancer cell into the host organism. The cancer cell comprises a compound suspected to be capable of modulating the amount or the activity of a Rab binding protein. The method further includes monitoring the growth of any tumor (including a plurality thereof) in the host organism.

In yet a further aspect the invention provides a method of determining whether a neoplasm is sensitive to an alteration of intracellular calcium levels. The method includes determining the expression and/or the activity of a Rab binding protein. An increased expression or an increased activity of the Rab binding protein is an indication that the neoplasm is sensitive to an alteration of intracellular calcium levels.

BRIEF DESCRIPTION OF THE DRAWINGS

The invention will be better understood with reference to the detailed description when considered in conjunction with the non-limiting examples and the accompanying drawings.

FIG. 2 is a table showing the clinical characteristics of the breast cancer cohorts used to construct the integrated microarray dataset.

FIG. 5 depicts TRIAGE analysis of 17q12 and 8p11 amplicons. A-B: Expression heatmaps of the probable expression amplicons (PEAs) at (A) 17q12 and (B) 8p11 are shown. Tumors are arranged in columns and genes identified by LSVD are organized in rows (in order along the chromosome). Tumors are ranked by the absolute value of the eigen weight (shown below heatmap). Above-mean expression is shown in white. Genes with significant survival associations at TRIAGE step 3 (see FIG. 1) are shown on the right. Genes in white letters indicate top oncogene candidates by TRIAGE. FIG. 5C and FIG. 5D depict the same data as FIGS. 5A and 5B, with below-mean expression shown in white.

FIG. 9 illustrates that RCP regulates tumor formation in nude mice. A-B: Effect of RCP inhibition on tumor growth in vivo using MCF7 cells (FIG. 9A, FIG. 9B, FIG. 9C) and MB231 cells (FIG. 9D, FIG. 9E, FIG. 9F). FIG. 9G depicts an immunohistochemical staining for RCP in tumor samples. (Scale bars, 100 µm.). FIG. 9H shows the apoptotic effects of RCP inhibition in serum-starved MB231 cells by TUNEL staining. (Scale bars, 100 µm.)

DETAILED DESCRIPTION OF THE INVENTION

Figure 1:
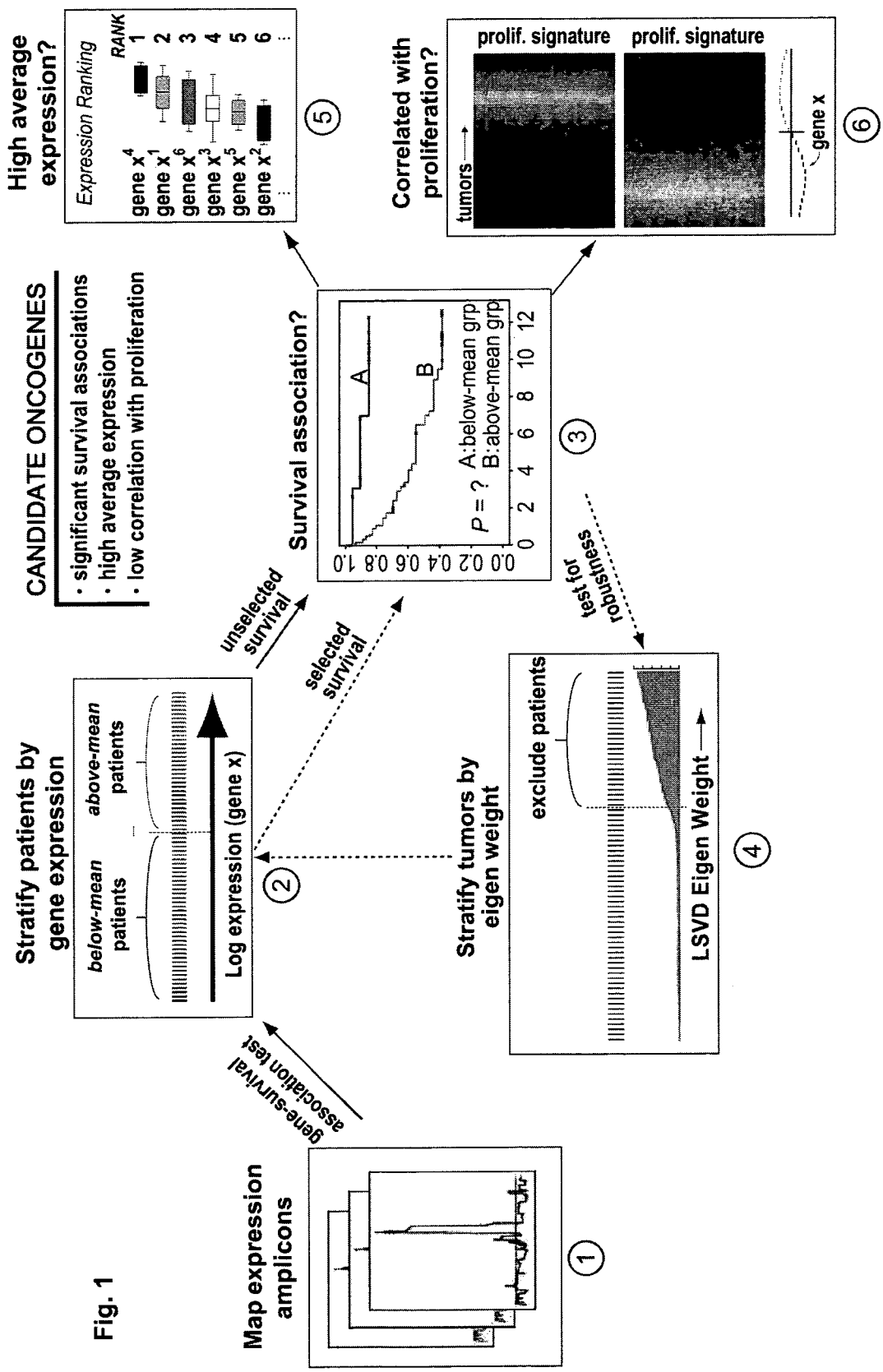
FIG. 1 depicts a multi-step schematic of the TRIAGE methodology.

The present invention is based on the surprising finding that Rab binding proteins and in particular Rab11FIP proteins (Rab11 family-interacting proteins) are able to promote the formation of neoplasms, including tumors, and in particular cancer.

The present inventors hypothesized that the pathophysiologic involvement of genes at genomic sites of recurrent amplification might be inferred with greater resolving capacity through the integration and triangulation of genomic position, gene expression and clinical data, where the latter allows for statistical associations to be drawn between gene expression and clinical measures of tumor aggressiveness. To this end, a multi-step data mining strategy was developed that led to the finding of Rab11FIP proteins as oncogene. The methods of the present invention are based on this finding.

This finding of the inventors also provides an explanation of the data reported on the involvement of the gene localizations, on which the proteins of the RAB11FIP are encoded, to an increased probability of cancers. For example, the human RAB11FIP1 gene (accession No ENSG00000156675 of the Ensembl database) is found on Chromosome 8 in the p12 region, at location 37,835,628-37,876,161. Likewise, the macaque RAB11FIP1 gene (accession No ENSMMUG00000003213 of the Ensembl database) is found on Chromosome 8, at location 38,309,752-38,349,824. The dog RAB11FIP1 gene (accession No ENSCAFG 00000006176 of the Ensembl database) is found on Chromosome 16, at location 30,456,385-30,484,441. The chicken RAB11FIP1 gene (accession No ENSGALG00000003129 of the Ensembl database) is found on Chromosome 22, at location 2,258,738-2,267,830. The human chromosomal region 8p12 has previously been shown to be amplified in a certain number of analyzed breast cancers (Letessier, A., et al., (2006) *BMC Cancer* (2006) 6, 1-13, available at http://www.biomedcentral.com/content/pdf/1471-2407-6-245.pdf). Losses, gains, amplifications and rearrangements of the short arm of chromosome 8 have also been shown to be found in a set of breast, colon and pancreatic cancer cell lines (Pole, J. C. M., et al. (2006) *Oncogene* 25, 5693-5706). A correlation of an alteration of the human chromosomal region 8p12 with lung cancers in patients who underwent surgical resection has been observed (Kim, T.-M., et al., (2005) *Clinical Cancer Research*, 11, 23, 8235-8242). Using comparative genomic hybridization, amplifications and deletions in the gene locus were also shown to occur in pancreatic and lung cancer subtypes (Tonon, G., et al., (2005) *Proc Natl Acad Sci USA*, 102, 27, 9625-9630). Copy number losses at the same locus were also observed in colon cancer samples obtained from patients (Yaginuma, Y, et al. (2006) *Journal of International Medical Research*, 34, 4, 390-396).

Rab11 family interacting proteins (FIPs) proteins share a homologous Rab11-binding domain, which is located at or near the C terminus (see e.g. Hales, C. M, et al., *J. Biol. Chem.* (2001) 276, 42, 39067-39075). Based on their domain architecture Rab11FIP proteins have been divided into two subfamilies, which are class I (FIP5/Rip11, FIP1 and FIP2) and class II (FIP3/eferin, and FIP4). The term "Rab11FIP proteins" as used herein thus refers to any member of the family of Rab11 family interacting proteins, in particular to Rab11FIP1, Rab11FIP2, Rab11FIP3 (eferin), Rab11FIP4, Rab11FIP5 (Rip11), and isoforms thereof. Examples of a Rab11FIP1 protein include, but are not limited to, the proteins of the SwissProt accession numbers Q05A58 (Q05A58_MOUSE), Q8K028 (Q8K028_MOUSE), Q6WKZ4 (RFIP1_HUMAN), Q9D620 (RFIP1_MOUSE), Q3B7T9 (RFIP1_RAT), Q6KAN5 (Q6KAN5_MOUSE), Q307T1 (Q307T1_HUMAN), Q28BL8 (Q28BL8_XENTR), (from Xenopus tropicalis), A41HL6 (A41HL6_XENTR) (from Xenopus tropicalis) e.g. with the genes of the SwissProt accession numbers ENSG00000156675 (human), ENSMUSG00000031488 (mouse), ENSPTRG00000020164 (chimpanzee), ENSPPYG00000018515 (orangutan), ENSMMUG00000003213 (rhesus monkey), ENSCAFG00000006176 (dog), ENSGALG 00000003129 (chicken), ENSMODG00000010813 (gray short-tailed opossum), ENSMLUG 00000007472 (little brown bat), ENSMICG00000010174 (gray mouse lemur), ENSOCUG 00000004502 (rabbit), ENSCPOG00000008298 (guinea pig), ENSETEG00000007044 (small Madagascar hedgehog), ENSECAG00000016134 (horse), ENSOANG00000003030 (platypus), ENSOPRG00000010860 (American pika), ENSSTOG00000005565 (thirteen-lined ground squirrel), ENSDNOG00000008299 (nine-banded armadillo), ENSLAFG00000004250 (African savanna elephant), ENSOGAG00000005737 (small-eared galago), e.g. the nucleic acid sequences of the SwissProt accession numbers DQ236342 (human), BC125400 (mouse), BC132094 (mouse), BC034201 (mouse), BC077720 (human), CX078607 (rhesus monkey), DR005339 (human), BC135580 (Xenopus tropicalis), including the coding sequences of the SwissProt accession numbers AAH34201 (mouse), AAI25401 (mouse), AAI32095 (mouse), ABB43161 (human), AAH77720 (human), EAW63349 (human), EAW63347 (human), EAW63348 (human), AAI35581 (Xenopus tropicalis) and CAJ81459 (Xenopus tropicalis). Examples of a Rab11FIP2 protein include, but are not limited to, the proteins of the SwissProt accession numbers Q5 HZIO (Q5 HZIO_MOUSE), Q7L804 (RFIP2_HUMAN), Q3U366 (Q3U366_MOUSE), e.g. with the genes of the SwissProt accession numbers ENSMUSG00000040022 (mouse), ENSG00000107560 (human), ENSGALG00000009304 (chicken), ENSPTRG00000002982 (chimpanzee), ENSMODG00000009385 (gray short-tailed opossum), ENSXETG00000009541 (Xenopus tropicalis), ENSMMUG00000021805 (rhesus monkey), ENSCAFG00000011991 (dog), ENSPPYG00000002692 (orangutan), ENSEEUG00000006651 (western European hedgehog), ENSMLUG00000015200 (little brown bat), ENSMICG00000001976 (gray mouse lemur), ENSOCUG00000009241 (rabbit), ENSCPOG00000000453 (guinea pig), ENSETEG00000019294 (small Madagascar hedgehog), ENSECAG00000019791 (horse), ENSSARG00000001794 (European shrew), IGI00014376 (Integr8 database, human), IGI00031145 (Integr8 database, mouse) and IGI02699308 (Integr8 database, bovine), and e.g. the nucleic acid sequences of the SwissProt accession numbers BC089010 (mouse), BC075073 (human), BC075074 (human) and DN994254 (human), including the coding sequences of the SwissProt accession numbers AAH89010 (mouse), EAW49423 (human), AAH75073 (human) and AAH75074 (human). Examples of a Rab11FIP3 protein include, but are not limited to, the proteins of the SwissProt accession numbers Q75154 (RFIP3_HUMAN), Q8JZT3 (Q8JZT3_MOUSE), A21DEO (A21DEO_HUMAN), A2A2G1 (A2A2G1_HUMAN), A21DD9 (A21DD9HUMAN), A2A2G0 (A2A2G0_HUMAN), and Q8CHD8 (Q8CHD8_MOUSE), e.g. with the genes of the SwissProt accession numbers ENSG00000090565 (human), ENSMUSG00000037098 (mouse), ENSPTRG00000007543 (chimpanzee), ENSMMUG00000000613, IGI00010332 (Integr8 database, human) and IGI00087092 (Integr8 database, chicken), IGI00026472 (Integr8 database, mouse) e.g. the nucleic acid sequences of the SwissProt accession numbers AL049542 (human), Z98882 (human), BC023364 (mouse), BC037132

(mouse), BC051360 (human), and AL023881 (human), including the coding sequences of the SwissProt accession numbers AAH23364 (mouse), AAH37132 (mouse), CAI95788 (mouse), CAI95591 (human), CAI95593 (human), CAM26382 (human), CAM26383 (human), CAQ09643 (human), CAQ11003 (human) CAM28374 (human), AAH51360 (human), EAW85805 (human), EAW85806 (human), EAW85807 (human), EAW85808 (human), EAW85809 (human), and EAW85810 (human). Examples of a Rab11FIP4 protein include, but are not limited to, the proteins of the SwissProt accession numbers Q6DGI2 (Q6DGI2_BRARE), Q86YS3 (RFIP4_HUMAN), Q8BQP8 (RFIP4_MOUSE), Q5SYH4 (Q5SYH4_MOUSE), Q3LGD4 (Q3LGD4_BRARE), Q3U4R6 (Q3U4R6_MOUSE) and Q3LGD3 (Q3LGD3_BRARE), e.g. with the genes of the SwissProt accession numbers ENSDARG00000053855 (zebrafish), ENSG 00000131242 (human), ENSMUSG00000017639 (mouse), ENSMODG00000019209 (gray short-tailed opossum), ENSPTRG00000008974 (chimpanzee), ENSMMUG00000008127 (rhesus monkey), ENSOCUG00000007443 (rabbit), ENSMLUG00000016407 (little brown bat), ENSCP0G00000011634 (guinea pig), IGI00013025 (Integr8 database, human), IGI00029750 (Integr8 database, mouse), IGI02693035 (Integr8 database, zebrafish) and IGI00051410 (Integr8 database, zebrafish), e.g. the nucleic acid sequences of the SwissProt accession numbers BC076363 (zebrafish), BC093914 (human), BC101517 (human), AL591174 (mouse), BC135989 (Xenopus tropicalis) and DR000701 (human), including the coding sequences of the SwissProt accession numbers AAH76363 (zebrafish), AAI35990 (Xenopus tropicalis), CAI24833 (mouse), CAI24836 (mouse), EAW80265 (human), AAI01518 (human) and AAH93914 (human). Examples of a Rab11FIP5 protein include, but are not limited to, the proteins of the SwissProt accession numbers Q6ZQ33 (Q6ZQ33_MOUSE), Q9BXF6 (RFIP5_HUMAN), Q8R361 (RFIP5_MOUSE) and Q3UM85 MOUSE, e.g. with the genes of the SwissProt accession numbers ENSG00000135631 (human), ENSMUSG00000051343 (mouse), ENSGALG00000016092 (chicken), ENSBTAG00000006162 (cattle), ENSXETG00000011781 (Xenopus tropicalis), ENSOCUG00000000840 (rabbit) ENSPTRG00000012057 (chimpanzee), ENSMMUG00000002301 (rhesus monkey), ENSOGAG00000009150 (small-eared galago), ENSECAG00000007084 (horse), IGI00035642 (Integr8 database, mouse) and IGI00006075 (Integr8 database, human), e.g. the nucleic acid sequences of the SwissProt accession numbers DQ890991 (synthetic construct of human clone), DQ894168 (synthetic construct of human clone), BC035013 (human), BC026473 (mouse), BC044833 (mouse), BC051063 (mouse), DR770942 (rhesus macaque monkey), including the coding sequences of the SwissProt accession numbers AAH26473 (mouse), AAH44833 (mouse), AAH51063 (mouse), ABM81917 (synthetic construct), ABM85094 (synthetic construct), AAH35013 (human), EAW99750 (human), EAW99749 (human) and EAW99751 (human).

The small GTPase proteins of the Rab family are known to have crucial roles in regulating cellular activity including intracellular membrane trafficking, signal transduction, receptor recycling and the recruitment of effector proteins to cellular membranes. Similar roles have accordingly been ascribed to Rab family interacting proteins such as Rab11 family interacting proteins. Rab11-FIP3 has for example been shown to play a critical role in the function of the endosomal recycling compartment (see e.g. Horgan, C. P., et al., (2007), Traffic, 8, 414-430).

The Rab proteins belong to the larger family of Ras-related small G-proteins (including the Rho-related proteins) that regulate a wide range of basic cell functions including cytoskeletal organization and cell morphology, cytokinesis, vesicle transport and secretion, cell-cycle progression and cell differentiation. Several of these proteins and their regulators and effectors have been implicated in carcinogenesis and cancer progression. Among these, RAB25, which is frequently amplified in breast and ovarian cancers, has been shown to enhance proliferation and apoptotic resistance in vitro, and tumor formation in vivo. The RAB family of proteins play a central role in membrane trafficking and organelle compartmentalization, and RAB11, RCP's primary binding partner, is specifically involved in membrane protein recycling. RAB11 has been implicated in cell migration, and disruption of RAB11 pathways compromise migration in different cell types (Jones, M. C., et al., (2006) Curr Opin Cell Biol 18, 549-557; Powelka, A. M., et al., (2004) Traffic 5, 20-36; Yoon, S. O., et al., (2005) Cancer Res 65, 2761-2769). Furthermore, the competitive inhibition of RAB11 function decreases hypoxia-induced invasiveness of breast cancer cells (Yoon et al., 2005, supra) and alters trafficking of membrane receptors involved in invasion such as Integrin alpha 6 beta 4, EGFR, CXCR2 and PKC alpha (Jones et al., 2006, supra). Dysregulation of RAB gene expression is implied as a generalized component of many human tumors. However, the role of Rab interacting proteins in tumor progression has not been studied.

The present inventors have identified a broad range of cancer-promoting effects linked to Rab11FIP1 expression. In noncancerous breast epithelial cells, Rab11FIP1 overexpression led to malignant transformation, and increased cell motility and migration. In breast cancer cell lines, attenuation of endogenous Rab11FIP1 by RNA inhibition reduced proliferation, anchorage-independent growth, invasion and apoptotic resistance, and diminished tumor formation in nude mice. Physiologically, Rab11FIP1 is thought to interact primarily with Rab11 to regulate protein sorting in tubular endosomes (Peden, A. A., et al., (2004) Mol Biol Cell 15, 3530-3541). Rab11-Rab11FIP1 complexes have been shown to channel transferrin receptor away from lysosomes (the degradation pathway) to recycling endosomes (the recycling pathway), thereby promoting a relative increase in the level of membrane-bound receptor (Peden et al., 2004, supra). Though speculative, it is plausible that the transforming effects of Rab11FIP1 may be mediated by this shift towards the recycling pathway, prolonging the membrane localization (and thus function) of certain membrane proteins such as the integrins or growth factor receptors with oncogenic roles. The strong correlation the present inventors observed between Rab11FIP1 expression and ERK phosphorylation may reflect this possibility, as it may indicate a specific link between Rab11FIP1 (in the following also named RCP) and growth factor receptor-mediated MAPK activation.

Without being bound by theory, immunoprecipitation data obtained by the present inventors (not shown) show that there is a direct interaction between Rab11FIP1 and the small GTPase Ras, indicating the formation of a complex between the two proteins. The Ras proteins are a family of small monomeric proteins that are in the art known for their central position in apoptosis, cellular proliferation, and cancer. At least 11 distinct functional classes of proteins have been shown to be effectors of Ras proteins. Accordingly, Ras proteins are thought to be centrally located in complex signal transaction networks, in which they activate at least three overlapping and cooperative protein kinase cascades, namely Raf/MEK/ERK, Ral GTPase, and PI3K/Akt. As one randomly selected further illustrative example they act via the Rb/E2F and Dnmt-1, thereby causing epigenetic changes by methylation, such as inactivation of p16, which activates tumor cell growth. In turn, ras proteins are subject to complex regulatory mechanisms. Point mutated Ras genes are frequently found in one-third of various tumors and Ras genes are known to be oncogenes.

Some methods according to the present invention are methods of controlling tumorigenesis. These methods include in particular methods of preventing, inhibiting, arresting or reversing tumorigenesis. Tumorigenesis may for example be carcinogenesis, including the formation of malignant forms of carcinomas. Accordingly, the method may for example be included in a treatment or prevention of a proliferative disease or disorder, such as cancer.

Using the present method of the invention, tumorigenesis may be prevented, inhibited, arrested or reversed in any organism, including for instance a mammal, a fish, an amphibian, a bird or a microorganism. A respective microorganism is in some embodiments a cell. Such a cell may be obtained from, including directly taken or isolated from, an organism, such as for instance one of the examples above, such as a mammal. Examples of a suitable mammal include, but are not limited to, a rat, a mouse, a rabbit, a Guinea pig, an opossum, a dog, a cat, a chimpanzee, a rhesus monkey, a macaque, an orang-utan, a cattle (cow), a marmoset, an American pika, a galago ("bushbaby"), a squirrel, a nine-banded armadillo, an elephant and a human. The cell may also be a cell of a conventional cell line, for instance a cancer cell line. The cell is in some embodiments cultured. A respective cell may in other embodiments be included, for example part of, an organism, such as for instance one of the examples above.

Some embodiments of the present method according to the invention include modulating the amount of a Rab binding protein, such as a Rab11FIP protein. Modulating the amount of the Rab binding may include allowing a portion of the total number of the Rab binding protein molecules, present in a cell, in an in vitro set-up such as a test tube or in an organism, to be degraded. Degradation of the Rab binding protein may for instance be allowed to be carried out by a protease, such as a calpain protease (also termed calcium-activated protease or calpain). As an illustrative example, Rab11FIP1 has been disclosed to contain three PEST (Pro, Gly and Ser/Thr-rich) motifs, which serve as targets for calpains, and to be cleaved by calpains in vivo (Nicolas, M., et al. (2005) *Biochem. J.*, 389, 223-231). Modulating the amount of the Rab binding protein may also include modulating the expression of the Rab11FIP protein. This may for example be carried out by administering a compound that modulates the expression of the Rab11FIP protein. The expression of the Rab11FIP protein may be increased or reduced. As an illustrative example, the expression of the Rab11FIP protein may be reduced by means of a nucleic acid molecule, such as a non-coding nucleic acid molecule.

The term "nucleic acid molecule" as used herein refers to any nucleic acid in any possible configuration, such as single stranded, double stranded or a combination thereof. Nucleic acids include for instance DNA molecules (e.g., cDNA or genomic DNA), RNA molecules (e.g., mRNA), analogues of the DNA or RNA generated using nucleotide analogues or using nucleic acid chemistry, and PNA (protein nucleic acids). DNA or RNA may be of genomic or synthetic origin and may be single or double stranded. In the present method of the invention typically, but not necessarily, an RNA or a DNA molecule will be used. Such nucleic acid can be e.g. mRNA, cRNA, synthetic RNA, genomic DNA, cDNA, synthetic DNA, a copolymer of DNA and RNA, oligonucleotides, etc. A respective nucleic acid may furthermore contain non-natural nucleotide analogues and/or be linked to an affinity tag or a label. In some embodiments the nucleic acid molecule may be isolated, enriched, or purified. The nucleic acid molecule may for instance be isolated from a natural source by cDNA cloning or by subtractive hybridization. The natural source may be mammalian, such as human, blood, semen, or tissue. The nucleic acid may also be synthesized, e.g. by the triester method or by using an automated DNA synthesizer.

Many nucleotide analogues are known and can be used in nucleic acids and oligonucleotides used in the present method of the invention. A nucleotide analogue is a nucleotide containing a modification at for instance the base, sugar, or phosphate moieties. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

In some embodiments of the present method of the invention the nucleic acid molecule is a non-coding nucleic acid molecule, such as for example an aptamer or a Spiegelmer® (described in WO 01/92655). A non-coding nucleic acid molecule may also be an nc-RNA molecule (see e.g. Costa, F F, *Gene* (2005), 357, 83-94 for an introduction on natural nc-RNA molecules). Examples of nc-RNA molecules include, but are not limited to, an anti-sense-RNA molecule, an L-RNA Spiegelmer®, a silencer-RNA molecule (such as the double-stranded Neuron Restrictive Silencer Element), a micro RNA (miRNA) molecule, a short hairpin RNA (shRNA) molecule, a small interfering RNA (siRNA) molecule, a repeat-associated small interfering RNA (rasiRNA) molecule or an RNA that interacts with Piwi proteins (piRNA) (for a brief review see e.g. Lin, H., Science (2007) 316, 397). An illustrative example of suitable shRNA is given as SEQ ID NO: 3 and SEQ ID NO: 4 in the examples below.

The use of small interfering RNAs has become a tool to "knock down" specific genes. It makes use of gene silencing or gene suppression through RNA interference (RNAi), which occurs at the posttranscriptional level and involves mRNA degradation. RNA interference represents a cellular mechanism that protects the genome. SiRNA molecules mediate the degradation of their complementary RNA by association of the siRNA with a multiple enzyme complex to form what is called the RNA-induced silencing Complex (RISC). The siRNA becomes part of RISC and is targeted to the complementary RNA species which is then cleaved. This leads to the loss of expression of the respective gene (for a brief overview see Zamore, P D, & Haley, B (2005) *Science* 309, 1519-1524). This technique has for example been applied to silencing parasitic DNA sequences, such as the cleavage of HIV RNA, as disclosed in US patent application 2005/0191618.

A typical embodiment of such a siRNA for the current invention includes an in vitro or in vivo synthesized molecule of 10 to 35 nucleotides, in some embodiments 15 to 25 nucleotides. A respective si-RNA molecule may be directly synthesized within a cell of interest (including a cell that is part of a microorganism and an animal). It may also be introduced into a respective cell and/or delivered thereto. An illustrative example of delivering a siRNA molecule into selected cells in vivo is its non-covalent binding to a fusion protein of a heavy-chain antibody fragment (Fab) and the nucleic acid binding protein protamin (Song, E. et al. (2005), *Nature Biotech.* 23, 6, 709-717). In an embodiment of the present invention siRNA molecules are used to induce a degradation of mRNA molecules encoding one or more transcription factors involved in the (e.g. in vivo) synthesis of the Rab binding protein.

Some embodiments of the present method according to the invention include modulating the activity of a Rab binding protein, e.g. of a Rab11FIP protein. Modulating the activity of the Rab binding protein may include forming a complex between the Rab binding protein and a compound. This may for example be carried out by administering a compound that modulates the activity of the Rab binding protein. The activity of the Rab binding protein (e.g. the Rab11FIP protein) may be increased or reduced.

A respective compound can be administered by any suitable means. If the host organism is a mammal, the compound may for example be administered parenterally or non-parenterally (enterally). In a typical embodiment of administering to a mammal, the application ensures a delivery to blood and liver, for instance by administering a preparation of the compound orally, intravenously or by inhalation. Examples for preparations for an oral application are tablets, pills or drinking solutions, examples for preparations for intravenous administrations are injection or infusion solutions, examples of preparations for administration by inhalation are aerosol mixtures or sprays. If the host organism is a recombinant microorganism, examples of administration are the injection or addition of the compound to the environment of the microorganism. In case of the microorganism being a single cell, the latter form of administration may possibly be performed in combination with a technique that modifies the microorganism. Such a technique may comprise electroporation or a permeabilisation of the cell membrane.

Modulating the activity of a Rab binding protein, e.g. a Rab11FIP protein, may also include altering a posttranslational modification of the Rab binding protein, including altering the pattern of posttranslational modifications of the Rab binding protein. In some embodiments altering a posttranslational modification of the Rab binding protein, such as the Rab11FIP protein, includes the use of a compound that alters the pattern of posttranslational modifications of the Rab binding protein. Illustrative example of a respective posttranslational modification are phosphorylation, dephosphorylation, acetylation, and ubiquitylation. As a result of a respective posttranslational modification, e.g. phosphorylation, the activity of the Rab binding protein changes. As an illustrative example, Rab11-FIP2 function has been shown to be regulated by phosphorylation on serine 227 (Ducharme, N. A., et al., *Molecular Biology of the Cell* (2006) 7, 8, 3625-3637). Phosphorylated by the kinase MARK2/EMK1/Par-1B (MARK2), Rab11-FIP2 serves in establishing epithelial cell polarity (ibid.).

A compound that modulates the activity, expression, amount or subcellular localisation of a Rab binding protein, such as a Rab11FIP protein, may be any compound. Examples include, but are not limited to, a nucleic acid (see above), a peptide, a peptoid, an inorganic molecule and a small organic molecule. Peptoids can have a much higher cell permeability than peptides (see e.g. Kwon, Y.-U., and Kodadek, (2007) T., *J. Am. Chem. Soc.* 129, 1508-1509). A peptide may be of synthetic origin or isolated from a natural source by methods well-known in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant) antibody fragments are Fab fragments, Fv fragments, single-chain Fv fragments (scFv), diabodies or domain antibodies (Holt, L. J., et al., (2003) *Trends Biotechnol.*, 21, 11, 484-490). An example of a proteinaceous binding molecule with antibody-like functions is a mutein based on a polypeptide of the lipocalin family (WO 03/029462, Beste et al., (1999) *Proc. Natl. Acad. Sci. U.S.A.*, 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see WO 96/23879), proteins based on the ankyrin scaffold (Mosavi, L. K., et al., (2004) *Protein Science* 13, 6, 1435-1448) or crystalline scaffold (WO 01/04144) the proteins described in Skerra, (2000) *J. Mol. Recognit.* 13, 167-187, AdNectins, tetranectins, and avimers. Avimers contain so called A-domains that occur as strings of multiple domains in several cell surface receptors (Silverman, J., et al., (2005) *Nature Biotechnology* 23, 1556-1561). Adnectins, derived from a domain of human fibronectin, contain three loops that can be engineered for immunoglobulin-like binding to targets (Gill, D. S. & Damle, N. K., (2006) *Current Opinion in Biotechnology* 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y.-U., and Kodadek, T., (2007) *J. Am. Chem. Soc.* 129, 1508-1509). Where desired, a modifying agent may be used that further increases the affinity of the respective moiety for any or a certain form, class etc. of target matter.

A respective compound may also alter a posttranslational modification of a Rab binding protein (such as a Rab11-FIP protein). The compound may for instance be able to change the phosphorylation status of cellular components, including the Rab binding protein. A respective compound may also be a modulator of the degree of the phosphorylation of cellular proteins, including proteins that differ from the Rab binding protein. Such a protein may in turn alter a posttranslational modification of the Rab binding protein. An illustrative example of a respective compound is tyrosine kinase inhibitor. A large number of tyrosine kinase inhibitors are commercially available such as tyrphostins, quinazolines, quinoxalines, quinolines, 2-phenylaminopyrimidines, flavonoids, benzoquinoids, aminosalicylates or stilbenes (which are described in e.g. WO 9618738, WO 03035621 and references cited therein, for an example of their experimental identification see e.g. U.S. Pat. No. 6,740,665). Examples of tyrphostins are AG213, AG490, AG 879, AG 1295, AG 1478, AG 1517, AGL 2043, tyrphostin 46 and methyl 2,5-dihydroxycinnamate. Quinazolines are for instance PD153035, PD 156273, gefitinib or lapatinib; quinoxalines are for example PD153035 or ZD1839. An example for a quinoline is 5-methyl-5H-indolo[2,3-β]quinoline, an example for a 2-phenylaminopyrimidine is imatinib, examples for flavonoids are genistein or quercetin, an example for a benzoquinoid is herbimycin A, an example for an aminosalicylate is lavendustin A, and an example for a stilbene is piceatannol. Other suitable compounds may comprise a receptor tyrosine kinase inhibitor such as the tyrphostin erbstatin, an EGFR specific receptor tyrosine kinase inhibitor such as WHI-P97 or the tyrphostin AG 592, a tyrosine phosphorylation stimulator such as aurin tricarboxylic acid or a tyrosine phosphatase inhibitor such as sodium pervanadate or isoxazole carboxylic acids.

Further examples of compounds that have been reported to inhibit the function of protein kinases include, but are not limited to, bis monocyclic, bicyclic or heterocyclic aryl compounds (international patent application WO 92/20642) vinylene-azaindole derivatives (PCT WO 94/14808), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (European patent application No. 0 566 266 A1), seleoindoles and selenides (international patent application WO 94/03427), tricyclic polyhydroxylic compounds (international patent application WO 92/21660), and benzyl-phosphonic acid compounds (international patent application WO 91/15495). Yet other compounds that could be used as modulators include oxindolinones such as those described in U.S. patent application Ser. No. 08/702,232 filed Aug. 23, 1996.

A further example of a compound modulating a posttranslational modification of a Rab binding protein is an agonist or antagonist for a cell surface molecule that is able to induce the regulation of a protein kinase or protein phosphatase.

Another example of a compound that modulates the activity of a Rab binding protein such as a Rab11FIP proteins is a member of the D vitamins, such as vitamin D3 or vitamin D4, for example. Vitamin D3 (also called cholecalciferol, calciol or arachitol, IUPAC name (1S,3Z)-3-[(2E)-2-[(1R,3aS,7aR)-1-[(1R)-1,5-dimethylhexyl]octahydro-7a-methyl-4H-inden-4-ylidene]ethylidene]-4-methylene-cyclohexanol, also termed (3β,5Z,7E)-9,10-Secocholesta-5,7,10(19)-trien-3-ol) in its active form has the ability to induce growth arrest, differentiation, and cell death in malignant cells of various origins, including breast cancer. This observation has led to the development of vitamin D analogs as possible anticancer agents (see e.g. Baudet, C., et al. (1996) *Cancer Lett.* 100, 3-10; Hsieh, T., & Wu, J. M., (1997) *Biochem. Biophys. Res. Commun.* 235, 539-544; James, S. Y., et al. (1999) *Gen. Pharmacol.* 32, 143-154; Mathiasen, I. S., et al., (1999) *Cancer Res.* 59, 4848-4856). Compound EB 1089 is one such analog and is currently in phase III clinical trials for the treatment of cancer (see e.g. Mathiasen, I. S., et al., (1993) *J. Steroid Biochem. Mol. Biol.* 46, 365-371; Colston, K. W., et al., (1992) *Biochem. Pharmacol.* 44, 2273-2280; Hansen, C. M., et al., (2000) *Curr. Pharm. Des.* 6, 803-828). The anticancer activity of vitamin D compounds is directly related to its effects on intracellular free calcium ($[Ca^{2+}]$). The elevation of free $Ca^{2+}$ in cells treated with vitamin D compounds correlates with the induction of apoptosis in breast cancer cells (Sergeev, I. N., et al., (2000) in *Vitamin D Endocrine System: Structural, Biological, Genetic and Clinical Aspects* (Norman, A. W., Bouillon, R., and Thomasset, M., eds) pp. 399-402, University of California, Riverside, Calif.; Vandewalle, B., et al. (1995) *Int. J. Cancer* 61, 806-811; Sergeev, I. N., & Rhoten, W. B., (1998) *Endocrine* 9, 321-327), and has been shown to be a primary mechanism in the activation of the calcium-dependent cysteine proteases, also known as calpains (Nakagawa, T., & Yuan, J., (2000) *J. Cell Biol.* 150, 887-894; Ray, S. K., et al., (2000) *Brain Res.* 852, 326-334; Ishihara, I., et al., (2000) *Neurosci. Lett.* 279, 97-100).

Without wishing to be bound by theory, recent evidence from studies in breast cancer cells suggests that the calpains may be the primary execution proteases in apoptotic death induced by vitamin D3 and EB 1089 (Mathiasen, I. S., et al., (2002) *J. Bio. Chem.* 277, 30738-30745). The protease (protein degradation) function of calpains depend on PEST (Pro, Gly, and Ser/Thr-rich) amino acid motifs present in the peptide sequence of protein targets of calpains (Dice, J. F. (1987) *FASEB J.* 1, 349-357; Tompa, P., et al., (2004) *J. Biol. Chem.* 279, 20775-20785; Rechsteiner, M., & Rogers, S. W., (1996) *Trends Biochem. Sci.* 21, 267-271; Shumway, S. D., et al., (1999) *J. Biol. Chem.* 274, 30874-30881; Fukuda, M., & Itoh, T., (2004) *J. Biol. Chem.* 279, 22314-22321). RAB11FIP1, contains for example three such PEST motifs located between the C2 domain and the RBD (Rab binding domain). In a recent study, Marie, et. al. sought to determine if the PEST motifs in RAB11FIP1 target it for regulated degradation by calpains (Marie, N., et al., (2005) *Biochem. J.* 389, 223-231). They observed that treating cells with increasing concentrations of calcium triggers the degradation of RAB11FIP1, and this degradation can be abolished by addition of specific calpain inhibitors. Furthermore, the involvement of PEST sequences in this calcium-regulated degradation was validated using an RAB11FIP1 mutant in which the PEST sequences were removed. Thus, the authors concluded that the PEST sequences of RAB11FIP1 target the protein for calpain-mediated degradation, presumably as a mechanism of physiological turnover in the cell. Given that for example RAB11FIP1 contains active PEST domains sensitive to calpain action, and that calpains are activated for proteolytic activity via vitamin D3 and its chemotherapeutic analogs such as EB 1089, the methods of the invention allow for RAB11FIP1 mRNA or protein levels to be used as a biomarker for selecting patients for chemotherapy regimens based on vitamin D3 and its related analogs including EB 1089, and any other treatment regimens that biochemically act to elevate intracellular free calcium levels or activate the calpains.

As noted above, in some embodiments of a method of controlling, e.g. a method of preventing, arresting or reversing tumorigenesis in a cell, the levels, the expression and/or the activity of a Rab binding protein are analysed. The cell may be an (e.g. isolated) individual cell, a cell of an organism, which may harbor cancerous tissue, a cell of a tissue, including a cancerous tissue, or a cell of a cell culture. A cancer cell may for instance be a neuronal, glial, lung, liver, brain, breast, bladder, blood, leukemic, colon, endometrial, stomach, skin, ovarian, fat, bone, cervical, esophageal, pancreatic, prostate, kidney, or thyroid cell In some aspects a cancer includes, but is not limited to astrocytoma, acute myelogenous leukemia, breast carcinoma, bladder carcinoma, cervical carcinoma, colorectal carcinoma, endometrial carcinoma, esophageal squamous cell carcinoma, glioma, glioblastoma, gastric carcinoma, hepatocellular carcinoma, Hodgkin lymphoma, leukemia, lipoma, melanoma, mantle cell lymphoma, myxofibrosarcoma, multiple myeloma, neuroblastoma, non-Hodgkin lymphoma, lung carcinoma, non-small cell lung carcinoma, ovarian carcinoma, esophageal carcinoma, osteosarcoma, pancreatic carcinoma, prostate carcinoma, squamous cell carcinoma of the head and neck, thyroid carcinoma and urothelial carcinoma.

An altered amount, an altered expression or an altered activity of a Rab binding protein in a cell may be adjusted to a level corresponding to about an average level or to a commonly found level. Altering the amount of the Rab binding protein in the cell may be achieved via the modulation of the activity or of the expression of a protease. In some embodiments such a protease is a calcium dependent protease (calpain), e.g. calpain I or II. In some embodiments the activity and/or the expression of a calpain protease is modulated via an alteration of intracellular calcium levels, e.g. free intracellular calcium.

In some embodiments the activity and/or the expression of a calpain protease is modulated, e.g. activated, by the use of a member of the vitamin D family, a prodrug of such a member of the vitamin D family or an analog of such a member of the vitamin D family, including by application thereof. A respective vitamin D, analog or prodrug thereof may for example be contacted with a respective cell or be administered to a respective organism, including a respective subject. The activity and/or the expression of a protease may also be modulated by other factors such as a protease modulator that is in turn modulated via signal transduction cascades. Numerous proteases are known to be subject to regulation both in terms of their activity and their expression (see e.g. Turk, B., (2006) *Nature Reviews Drug Discovery*, 5, 9, 785-799). Apoptotic protease activating factor-1 or tissue inhibitors of metalloproteinase may serve as illustrative examples.

A "prodrug" of a member of the vitamin D family or an analog of a member of the vitamin D family is understood to be a compound that is transformed (e.g gradually or rapidly) in vivo to yield the parent vitamin D/vitamin D analog compound, for example by metabolization in the host, including e.g. by hydrolysis in blood or by oxidation, by either enzymatic action or by general acid or base solvolysis, to form an active ingredient. Typically a prodrug is a derivative of the parent vitamin D/vitamin D analog, which on use in vivo releases the original compound through a chemical or physiological process. A prodrug may for instance be converted into the parent vitamin D/vitamin D analog when a physiological pH is reached, by spontaneous chemical reaction(s), enzyme catalyzed chemical reaction(s), photolysis, and/or metabolic chemical reaction(s). Common examples are compounds with biologically labile protecting groups on a functional moiety of the parent compound, including, but not limited to, ester and amide forms of a compound having an active form bearing a carboxylic acid moiety. Further examples include moieties of compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug. A respective prodrug may as such not be fully active or physiologically available until converted in vivo to its therapeutically active or available form. A "prodrug" may also include a product formed, in vitro or physiologically, by a covalent or noncovalent bond between the respective drug molecule (in this case the parent vitamin D/vitamin D analog) and a carrier moiety. It is also to be understood that certain compounds can exist in solvated as well as unsolvated forms such as, for example, hydrated forms. A solvated form is also simply referred to as a "solvate".

As further noted above, in some embodiments of a method of identifying a cell having a predisposition to turn tumorigenic an altered amount, an altered expression or an altered activity of a Rab binding protein in the cell, which may be an (e.g. isolated) individual cell, a cell of an organism or a cell of a cell culture, may be determined. Likewise, in some embodiments of a method of diagnosing the risk of developing a neoplasm in a subject, e.g. a patient, an altered amount, an altered expression or an altered activity of a Rab binding protein may be determined. In such cases determining a respective alteration may be an indication that a respective neoplasm or tumor will be sensitive to an alteration of the activity and/or amount of a protease in the cell or in cells of the subject. In some embodiments such a protease is a calcium dependent protease (calpain) such as the calcium-dependent proteases CDPI or CDP II, also known as calpain proteases calpain I or II (also termed calcium activated neutral proteases I and II). In some embodiments determining an altered activity and/or expression of a Rab binding protein, may be an indication that a respective neoplasm or tumor will be sensitive to an alteration of intracellular calcium levels.

In this regard, a respective method can further include obtaining a sample from the subject as well as isolating nucleic acids from the sample. The nucleic acids may be amplified as well as labelled. Methods of determining the amount of a selected protein are well known in the art. A respective method may for instance rely on proteomics-based techniques. It may involve the use of an antibody, a fragment thereof or a proteinaceous binding molecule with antibody-like functions, which binds to the respective Rab binding protein. Methods of analyzing the expression protein of a protein are well established in the art. mRNA expression may for instance be quantified using northern blotting and in situ hybridization, RNAse protection assays and PCR-based methods. As a further example, an antibody, a fragment thereof or a proteinaceous binding molecule may be employed that can recognise specific duplexes, including DNA duplexes, RNA duplexes, and DNA-RNA hybrid duplexes or DNA-protein duplexes. Illustrative examples of methods of sequencing-based gene expression analysis include Serial Analysis of Gene Expression (SAGE), and gene expression analysis by massively parallel signature sequencing (MPSS).

Examples of (recombinant) antibody fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol*. (2003), 21, 11, 484-490). Single-chain Fv fragments are for instance fusions of variable regions from one heavy chain and one light chain of an immunoglobulin molecule. An example of a proteinaceous binding molecule with antibody-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit*. (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homo-trimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Where desired, a modifying agent may be used that further increases the affinity of the respective moiety for any or a certain form, class etc. of target matter.

PCR (polymerase chain reaction) is a standard technique useful to amplify and detect transcripts from a cell or from a tissue sample such as a melanoma sample. Reverse Transcriptase PCR (RT-PCR), is for instance a sensitive quantitative method that can be used to compare mRNA levels in different samples (e.g., non-metastatic and metastatic melanoma samples, or benign cutaneous and melanoma samples) to examine gene expression signatures. To perform RT-PCR, mRNA is isolated from a sample (e.g., total RNA isolated from a human melanoma sample). mRNA can be extracted, for example, from frozen or archived paraffin-embedded and fixed (e.g. formalin—fixed) tissue samples. Purification kits for RNA isolation are commercially available. The RT-PCR technique may also be used in the embodiment of real time quantitative PCR, which measures PCR product accumulation through a dual-labeled fluorigenic probe. Real time PCR is compatible both with quantitative competitive PCR, where internal competitor for each target sequence is used for normalization, and with quantitative comparative PCR using a normalization gene contained within the sample, or a housekeeping gene for RT-PCR. As a further example, the competitive PCR design may be used for gene expression analysis, possibly including automated, high-throughput matrix-assisted laser desorption ionization time-of-flight (MALDI-TOF) mass spectrometry detection and quantification of nucleic acid molecules. Further examples of techniques that may be included in PCR-based methods suitable for gene expression analysis may include, but are not limited to, differential display, amplified fragment length polymorphism (iAFLP), the BeadAmiy™ technology, BeadsArvay for Detection of Gene Expression (BADGE) and high coverage expression profiling (HiCEP) analysis. As a further example, determining gene expression of a tissue sample can also be performed with microarrays.

In some embodiments determining an altered activity and/or expression of a Rab binding protein, in particular an increased activity and/or expression of a Rab binding protein may be an indication that a respective neoplasm or tumor will be sensitive to treatment with a member of the D vitamins, an analog or a prodrug thereof. In this regard the present invention also provides a method of determining whether a neoplasm (including a tumor, e.g. cancer) is sensitive to an alteration of the activity and/or amount of a protease. The protease may be present, including expressed, therein, in particular in cells thereof. In some embodiments the method is a method of determining whether a neoplasm is sensitive to member of the vitamin D family, an analog or a prodrug thereof.

A large number of vitamin D analogs, including vitamin D3 analogs are known in the art that may be used in a method according to the present invention (for an overview see e.g. Kubodera, N., (2006) *Current Bioactive Compounds*, 2(3), 301-315). Suitable examples including e.g. calcitriol, maxacalcitol, tacalcitol, secalciferol, alfacalcidol or seocalcitol (EB 1089) have for instance been listed in international patent application WO 2007/082542. Seocalcitol has previously been shown to potentiate the response to ionizing radiation in breast cancer tumor cells, which has been suggested to be a consequence of alterations in cell signalling pathways downstream of the initial induction of DNA damage (DeMasters, G., et al., (2006) *Mol Cancer Ther*, 5, 11, 2786-2797). Further recent examples are 16-en-22-oxa-vitamin D3 analogs such as SMD-429, the formation of which has been described by Shimizu et al. ((2006) *Bioorganic & Medicinal Chemistry Letters*, 16, 3323-3329 & references cited therein), 1α,25-dihydroxy-20S,21 (3-hydroxy-3-methylbutyl)-23-yne-26, 27-hexafluorochole-calciferol as described by e.g. Lee et al. ((2007), *Cancer Research*, 67(24), 11840-11847) or the 1α,25-dihydroxyvitamin D3 analogs presented by Yoon et al. ((2008) *International Journal of Oncology*, 23, 387-396), 19-functionalized derivatives of 1α-hydroxy-5,6-trans-vitamin D3 (Wojtkielewicz, A., (2007) *Steroids*, 72(6-7), 552-558.), the analogs with elongated side chains described by Ono et al. ((2007), Journal of Combinatorial Chemistry 9(4), 711-716) or the difluoro analogs described by Posner et al. ((2007) *Journal of Steroid Biochemistry & Molecular Biology*, 103, 213-221).

For some embodiments of the invention, compounds may be used in form of a library. Examples of such libraries are collections of various small organic molecules, chemically synthesized as model compounds, or nucleic acid molecules containing a large number of sequence variants.

In some embodiments the present method of the invention includes detecting the expression, the subcellular localisation and/or the activity of the Rab11-FIP protein, for example in an organism or in a tissue or a cell thereof. As an illustrative example, the cellular amount, the expression, the subcellular localisation and/or the activity of the Rab11-FIP protein may be monitored over a period of time.

The present method of the invention may furthermore include comparing the results of measuring the cellular amount, the expression, the subcellular localisation and/or the activity of the Rab11-FIP protein with results of a control measurement (or "reference" measurement). A control measurement may include the use of conditions that do not modulate the cellular amount, the expression, the subcellular localisation and/or the activity of a Rab11FIP protein. In comparing cellular amount, expression, and/or activity, detected levels may for example be compared to a control level. The term "control level" as used herein refers to the number of molecules of the respective protein, e.g. in a cell, a mRNA or protein expression level of a Rab11FIP protein, as well as to an activity level of a Rab11FIP protein in a control sample. The term thus includes both a normal control level and a cancer control level (see also below). The term can refer to a single reference measurement or to a plurality of reference measurements. In some embodiments the control level may be a database of expression or activity values from previously conducted measurements. The term "customary level" refers to a level of expression of a Rab11FIP protein or an activity level of a Rab11FIP protein detected in a normal, healthy individual or in a population of individuals known not to be suffering from a neoplasm, including cancer. A normal individual is one with no clinical symptoms of a respective neoplasm.

According to the present invention, a gene expression level or an activity level or an amount of a protein, e.g. in a cell, is deemed to be "altered" or to "differ" when gene expression/activity/amount is increased or decreased by about 10%, about 25%, about 50%, about 75%, about 100%, or higher, as compared to the control level. Alternatively, an expression level or an activity level is deemed "increased" or "decreased" when gene expression/or an activity is increased or decreased by at least about 0.1, at least about 0.2, at least about 1, at least about 2, at least about 5, or at least about 10 or more fold as compared to a control level.

The present method of the invention may include altering the activity of extracellular signal-regulated kinase (ERK). In some embodiments the method includes preventing, inhibiting, arresting or reversing activation of ERK. In typical embodiments, modulating the amount or the activity of a Rab11-FIP protein may result in modulating the activity of ERK.

A further method of the invention is a method of identifying a cell that has a predisposition to turn tumorigenic, including cancerogenic. The method includes detecting in the cell an altered amount, an altered expression, an altered subcellular localisation or an altered activity of a Rab11FIP protein. As already explained above for a related method, the method may include measuring the cellular amount, the expression, the subcellular localisation and/or the activity of the Rab11-FIP protein. In some embodiments the method may also include comparing the results of measuring the cellular amount, the expression, the subcellular localisation and/or the activity of the Rab11-FIP protein with results of a control measurement (see above).

The present invention also relates to a method of diagnosing the risk of developing a neoplasm, such as a tumor, including cancer, in a subject. A respective tumor may for example be a breast tumor, a lung tumor, a colorectal tumor, a tumor of the urinary bladder or a tumor of the fallopian tube (also termed oviduct). Likewise, a respective cancer may for instance be breast cancer, lung cancer, colorectal cancer, cancer of the urinary bladder or cancer of the fallopian tube (also termed oviduct), including one of the corresponding carcinomas. An illustrative example of a carcinoma of lung cancer is a non-small cell lung carcinoma. The method includes determining at least one of the amount, the expression level, the activity level and the subcellular localisation of a Rab11FIP protein. The measurement may in some embodiments be carried out in a sample, such as a tissue sample or a cell sample, from the subject. In some embodiments the method may also include comparing the results of measuring the cellular amount, the expression, the subcellular localisation and/or the activity of the Rab11-FIP protein with results of a control measurement (see above). For a respective control measurement a sample may be used, in which the expression and/or the activity of the Rab binding protein is on a customary ("normal") level. In typical embodiments an altered amount, expression level, activity level or subcellular localisation of a Rab binding protein as compared to the control measurement indicates that the subject suffers from or is at risk of developing a neoplasm.

Further methods of the invention are methods, both in-vivo and in-vitro methods, of identifying a respective compound. The compound may be capable of preventing, inhibiting, arresting or reversing tumorigenesis, including carcinogenesis. The compound may be capable of forming a complex with a Rab binding protein, such as a Rab11FIP protein. Typically these methods include exposing the components of this complex to each other, whether in-vitro or in-vivo. One such method is an in-vitro method, which includes contacting the components that form, or are suspected to form, a complex with each other. For example a Rab11FIP protein and a drug candidate molecule, which is suspected to form a complex with the Rab11FIP protein, may be contacted with each other. In some embodiments the method further includes detecting the formation of the complex.

Any suitable method of detecting a complex formation may be used. A detection method may for instance include electrophoresis, HPLC, flow cytometry, fluorescence correlation spectroscopy or a modified form of these techniques. Other techniques involve a measurement of the biomolecular binding itself. Such measurements may for instance rely on spectroscopic, photochemical, photometric, fluorometric, radiological, enzymatic or thermodynamic means, or on cellular effects. An example for a spectroscopic detection method is fluorescence correlation spectroscopy (Thompson, N. L., et al, *Curr. Opin. Struct. Biol.* (2002) 12 (5), 634-641). A photochemical method is for instance photochemical cross-linking (Steen, H., Jensen, O. N., *Mass Spectrom Rev.* (2002) 21, 3, 163-182). The use of photoactive, fluorescent, radioactive or enzymatic labels respectively (for an overview see: Rippe, R. A., et al., *Methods Mol. Biol.* (2001) 160, 459-479) are examples for photometric, fluorometric, radiological and enzymatic detection methods. An example for a thermodynamic detection method is isothermal titration calorimetry (ITC, for an overview see: Velazquez-Campoy, A., et al., *Methods Mol. Biol.* (2004) 261, 35-54). An example of a method using cellular effects is the measurement of cell proliferation or cell viability including its enzymatic detection or cellular replication.

Further related methods are in-vivo methods that include providing a microorganism. The microorganism expresses the Rab binding protein, with which the compound is suspected to be capable of forming a complex, or the expression of which the compound is suspected to be capable of altering (e.g. suppressing). The microorganism may in some embodiments endogenously express the Rab binding protein. In some embodiments the microorganism is a recombinant cell or a transgenic microorganism. In some embodiments the microorganism is a single cell, such as a cancer cell, including a breast cancer cell or a lung cancer cell. In some embodiments the microorganism is a cell obtained from an organism. A respective organism may for instance be a mammal, a fish, an amphibian or a bird. A cell is typically derived from tissue of a respective organism, such as skin tissue or breast tissue. In some embodiments the microorganism is a cell of a cell line, such as a cancer cell line, including a breast cancer cell line or a lung cancer cell line. Examples of a suitable breast cancer cell line include, but are not limited to, a HMEC cell line, 3D, Bcap-37, BT-20, BT-474, BT474M1, Hs578T, Hs578Bst, JIMT-1, MCF-7, M231, MDA-231, MDA-MB-134, MDA-MB-175, MDA-MB-231, MDA-MB-361, MDA-MB-361DYT2, MDA-MB-435, MDA-MB-435HM, MDA-MB-468, MB231, MW1, PMC42, SK-BR-3, SK-BR-7, SUM149, SUM159, SUM1315, SUM-52PE, T-47D, ZR-75, ZR-75-1 and ZR-75-30. A lung cancer cell line may for example be an adenocarcinoma cell line, a squamous-cell carcinoma cell line or a small-cell carcinoma cell line. Examples of a suitable lung cancer cell line include, but are not limited to, ABC-1, A549, Calu-6, EBC-1, H322, H446, H460, HCC2279, HTB-56R, HUT29, IMEC-2, KU-T1, L9981, LCD, LCOK, LK-2, LC-1/sq, Lu135, MS-1, NCI_H69, NCI_H82, NCI_H209, NCI_H446, NCI_H1395, NCI_H1437, NCI_H1770, NCI_H2009, NCI_H2087, NCI-H2122, NCI_H2126, NCI_H2171, NCI_N226, NCI_N231, PC1, PC3, PC7, PC9, PC10, PC14, PLA-801D, QG56, RERF-LCAI, RERF-LCMS, RERF-LCKJ, SBC3, SPC-A1, SQ5 and YTLMC-90. Numerous other cancer cell lines are known in the art, e.g. the additional cell lines named in Pole et al. (2006, supra).

In some embodiments the microorganism is a cell of a colorectal cancer cell line, an urinary bladder cancer cell line and a fallopian tubal carcinoma cell line. Examples of a suitable colorectal cancer cell line include, but are not limited to, Colo-320, HCT116, HT-29, L0, L0-200, L0-500, L0-1000, LoVo, LS1034, LST-R1, RKO, SW480, and WiDr, as well as further colorectal cancer cell lines referred to by Douglas et al. ((2004) *Cancer Research* 64, 14, 4817-4825). Examples of a suitable bladder cancer cell line include, but are not limited to, BIU-87, EJ, KoTCC-1, MBT-2, RT4, ScaBER, T24 and UM-UC-2. Two illustrative examples of a fallopian tubal carcinoma cell line are FT-MZ-1 (Runnebaum, I. B., et al., (1994) *FEBS Lett.,* 353, 1, 29-32) and HEPFT (see Ishiwata, I., et al., (2007) *Human Cell,* 20, 119-130).

In some embodiments the microorganism is a cell of a non-tumorigenic, including non-cancerous tissue cell line, such as the breast cancer epithelial cell line MCF10A, overexpressing a Rab binding protein, such as a Rab11FIP, e.g. RAB11FIP1. Likewise, any cell—whether of a cell line, an individual cell, a cell within a multicellular organism, a cell obtained (including directly obtained and isolated) from a multicellular organism—may be selected and transformed into a cancer cell by overexpressing a Rab binding protein such as RAB11FIP1. The examples below and e.g. FIG. 6 illustrate how a cell can be transformed into a cancer cell accordingly. In this regard the method also provides a method of obtaining a cancer cell, which includes a method of modulating, in particular increasing, the expression of a Rab binding protein in a cell. Thereby the cell is transformed into a cancer cell. The respective Rab binding protein may for example be a Rab11 binding protein such as RAB11FIP1. It may be an endogenous or an heterologous protein, i.e. a protein with an encoding nucleic acid sequence naturally occurring in the cell or a protein of which the encoding nucleic acid sequence is being/has been introduced into the respective cell. The invention also relates to the use of such a cell for identifying a compound capable of modulating the expression of the corresponding Rab binding protein in vivo (see below).

The present methods of the invention include adding the compound, which is suspected to be capable of forming a complex with the Rab binding protein, or to be capable of altering its expression, to the microorganism. In some embodiments of a respective method, the expression of the Rab binding protein, e.g. a Rab11FIP protein, is monitored. In some embodiments of a respective method the activity of the Rab binding protein is monitored. In some embodiments a change in cell phenotype of the Rab binding protein is monitored. In some embodiments such a method includes a control measurement (see also above). The results of the control measurement are compared to the results obtained using the compound. A control measurement may for example include the use of a compound that is known not to affect the expression or the activity of the Rab binding protein.

Yet other related methods are an in-vivo methods that include providing a host organism. Any desired host organism may be provided as long as it is capable of accommodating and growing a cancer cell. Examples of a host organism include, but are not limited to, a mammal, a fish, an amphibian and a bird. Examples of a suitable mammal include, but are not limited to, a rat, a rabbit, a Guinea pig, an opossum, a dog and a cat.

Any desired cancer cell may be used for this purpose (see above for examples). The method further includes introducing a cancer cell into the host organism. Furthermore the method includes the use of a compound as described above, i.e. a compound that is suspected to be capable of forming a complex with a Rab binding protein, to be capable of modulating the amount of a Rab binding protein, or to be capable of modulating the activity of a Rab binding protein. In some embodiments the cancer cell includes the compound. Accordingly the compound may be introduced into the cancer cell before introducing the same into the host organism. In some embodiments the compound is administered to the host organism, before, after or concurrently with introducing the cancer cell therein. Typically the compound is introduced into the cancer cell at a certain stage of the method. The method further includes monitoring the growth of tumors in the host organism.

In order that the invention may be readily understood and put into practical effect, particular embodiments will now be described by way of the following non-limiting examples.

EXAMPLES

The particularly relevant aspects and features of the TRIAGE method developed by the inventors can be summarized as follows (see also FIG. 1):

| TRIAGE steps: | TRIAGE steps: |
| --- | --- |
| Correlating amplicon genes with distant metastasis-free survival | RATIONALE |
| 1. Putative expression amplicons are mapped by genome-wide LSVD; those that overlap with chromosomal regions of known recurrent amplification are further investigated. | 1. Expression footprints of recurrent genomic amplicons can be detected by LSVD. |
| 2. Patients are stratified by each amplicon gene into below-mean and above mean expression groups. | 2. & 3. Some metastasis-promoting oncogenes frequently activated by amplification should have expression patterns that correlate with poor DMFS in breast cancer patients, reflecting their functional involvement in metastatic progression. |
| 3. Cox proportional hazards regression (2-group survival analysis) is performed and the significance of the hazards ratio (p-value) is reported for each gene. | 4. Passenger genes located on survival-associated amplicons may correlate with poor DMFS without functional involvement. Oncogenes activated by multiple cancer mechanisms not limited to amplification should be associated with poor outcome in the absence of the amplicon, whereas passenger genes should not. |
| Testing for robustness; discriminating oncogenes from passenger genes | |
| 4. Tumors are ranked by eigen weight to estimate the amplicon-containing tumors. Steps 2 & 3 are repeated excluding those patients with amplicon containing tumors. | |
| 5. Genes within the amplicon are ranked by their average expression in the amplicon-containing tumors. | 5. The oncogenic driver(s) of an amplicon should be relatively highly and consistently expressed in amplicon-containing tumors. |
| 6. The Pearson correlation between expression pattern and the proliferation signature is calculated for each gene. | 6. DMFS-associated genes also correlated with proliferation are considered with caution, as proliferation itself is associated with metastasis of breast cancer. |

Cells and Drug Treatment

Microarray data and tumor samples. Four previously described breast cancer microarray datasets were used in this study, and all expression profiles were generated using the Affymetrix U133A and U133B genechips as described in the original publications: Uppsala cohort (Miller, L. D., et al. (2005) *Proc Natl Acad Sci USA* 102, 13550-13555.), Stockholm cohort (Pawitan, Y., et al. (2005) *Breast Cancer Res* 7, R953-964), Belgium cohort (Loi, S., et al. (2007) *J Clin Oncol* 25, 1239-1246) and Singapore cohort (Ivshina, A. V., et al. (2006) *Cancer Res* 66, 10292-10301). All Affymetrix CEL files were retrieved from the Gene Expression Omnibus (http://www.ncbi.nlm.nih.gov/geo/), normalized using the global mean method (Miller et al., 2005, supra), and probe set signal intensities were natural log transformed and scaled by adjusting the mean intensity to a target signal value of log 500. To remove cohort-dependent array biases, arrays within each cohort were mean-centered prior to combining them into one dataset. Clinical characteristics of all patients and tumor samples are summarized in FIG. 2.

Local Singular Value Decomposition (LSVD). Microarray probe sets were mapped to genomic coordinates according to the UCSD Genome Browser. Candidate PEAs were identified as the localized coordinated overexpression of genes in a corresponding subset of tumors. First, a gene was defined as overexpressed in a sample if its expression in that sample was >2.5 times the adjusted median absolute deviation (aMAD) from its median expression across all samples (FIG. 1, step 1). Second, localized coordinated overexpression was quantified by the principal eigen value obtained by SVD applied on a sliding window of 50 probes. Probes corresponding to the same gene (according to UniGene ID, build #177) were averaged to represent a single gene measurement. Candidate PEAs were identified as contiguous chromosomal regions having local principal eigen values above a baseline threshold. Candidate PEAs were scored and ranked by the peak principal eigen value. Highest scoring candidate PEAs were subjected to a second round of LSVD using a window size of 10 probes to better resolve peak structure (ie, to distinguish one from multiple sub-peaks). Finally, highest scoring sub-peaks were then subjected to SVD to derive eigen weights for the individual genes and tumors. Eigen weights reflect the relative contribution of genes and tumors to the magnitude of a principal eigen peak. For a given peak, genes with nonzero eigen weights were considered components of the PEA. Tumors with an eigen weight greater than the median plus 2 standard deviations were labeled as amplicon-containing tumors (TRIAGE, step 4).

Local Singular Value Decomposition (LSVD) to identify recurrent genomic amplifications. LSVD analysis of gene expression profiles from a cohort of tumor samples is a key first step in identifying probable expression amplicons (PEAs), from which oncogenes contributing to metastasis may be discovered by the TRIAGE methodology (Triangulating Oncogenes through Clinico-Genomic Intersects). LSVD identifies PEAs based on the hypothesis that a recurrent amplicon will manifest as the coordinated overexpression of genomically localized genes in a subset of tumor samples. LSVD is built around singular value decomposition (SVD) (Strang, G., (1998) "Introduction to Linear Algebra", Section 6.7. 3rd ed., Wellesley-Cambridge Press. ISBN 0-9614088-5-5) and predicts PEAs as peaks in the coordinated local overexpression plot which is a local principal eigen value (LPEV) plot obtained by the local application of SVD on a chromosome-by-chromosome basis. LSVD is achieved by deriving local expression matrices for each genomic position on the genome, transforming it to a binary connectivity matrix and applying SVD on the binary matrix. The principal eigen value obtained upon such application is a measure of the coordinated overexpression of genes at that locus (Kluger, Y., et al., (2003) *Genome Research*, 13, 703-716; Kleinberg, J. M., (1999) *Jl of the ACM*, 46, 5, 604-632). Eigen value "peaks" that exceed a certain basal threshold in the plot of LPEV vs. genomic location (LPEV plot) demarcate the PEAs. The detailed description of the LSVD procedure is provided below.

Let $E_c$ be the gene expression matrix of chromosome G; $E_{cij}$ is the $\log_2$ of the expression of gene at location $l_i$ in tumor $T_j$, where i=1, 2, ..., $N_c$ and j=1, 2, ..., M. Probable Expression Amplicons (PEAs) on G are predicted by analyzing $E_c$ using LSVD which has the following sequence of steps: (1) Transforming $E_c$ to binary connectivity matrix $A_c$; (2) Deriving Chromosome Localized Matrices, $Ap_c$; (3) SVD on $Ap_c$; and, (4) Identifying PEAs.

1. Transforming $E_c$ to binary connectivity matrix $A_c$: $E_c$ is transformed to a binary connectivity matrix $A_e$ through a boolean descretization rule as follows:

$$A_{cij}=1 \ if \ E_{cij}>\mu_i+x^*\nu_i$$

$$A_{cij}=0 \ if \ E_{cij}\leq\mu_i+x^*\nu_i$$

where $\mu_i$ and $\nu_i$ are the median and adjusted Median Absolute Deviation (aMAD) of $E_{ci}=\{E_{ci1}, E_{ci2}, ..., E_{ciM}\}$. aMAD is 1.4826 times the MAD. x is 2.5 for the first pass of coarse map and the 2 for the finer map obtained in the second pass.

2. Deriving Localized Matrices, $Ap_c$: A local matrix $Ap_c$ at position $Lp_c$ is derived from $A_c$ using genes at positions from p−w to p+w on chromosome $C_c$ where w is the window size, a predefined parameter. w is 50 for the first pass coarse map and 10 for the second pass finer map.

3. Singular Value Decomposition (SVD): The application of SVD on $Ap_c$ is a crucial step to predict PEAs. The SVD of $Ap_c$ decomposes $Ap_c$ into a product of three matrices $Up_c$, $\Sigma p_c$ and $Vp_c$ i.e. $Ap_c=Up_c\times\Sigma p_c\times Vp_c^T$. $Up_c$ and $Vp_c$ are of (2w+1)×(2w+1) and M×M matrices respectively while $\Sigma p_c$ is (2w+1)×M diagnol matrix. The column vectors of $Up_c$ and $Vp_c$ are the eigen vectors of $Ap_c Ap_c^T$ and $Ap_c^T Ap_c$ respectively while the diagonal elements of $\Sigma p_c$ are the respective eigen values. The highest eigen value is called the principal eigen value (denoted by $\lambda p_c$) and the respective eigen vectors are called the principal eigen vectors. Eigen weight of tumor $T_j$ at position $Lp_c$ is denoted by $Tp_{cj}$ and it defined as the absolute of the $j^{th}$ component of the principal eigen vector of the matrix $Ap_c^T Ap_c$. Similarly, eigen weight of a gene $G_i$ at position $Lp_c$, denoted by $Gp_{cj}$ is the absolute of the $j^{th}$ component of the principal eigen vector of the matrix $Ap_c Ap_c^T$.

To improve the contrast between true PEA signal and background, in our LSVD implementation, we use SVD on $(Ap_c Ap_c^T)^3$ instead of on $Ap_c$ to find $\lambda p_c$. The eigen weights of tumors and genes are obtained, following the above definitions, from the principal eigen vectors of $(Ap_c^T Ap_c)^4$ and $(Ap_c Ap_c^T)^4$ respectively. Now, $\lambda p_c$ is the ratio of the fourth root of the principal eigen value of $(Ap_c Ap_c^T)^4$ to $M^4$; the eigen weights of genes and tumors are the fourth root of the respective components of the principal eigen vectors of $(Ap_c Ap_c^T)_4/M^4$ and $(Ap_c^T Ap_c)^4/M^4$ respectively.

4. Predicting PEAs: Plotting $\lambda p_c$ vs. $Lp_c$ gives the plot of LPEVs, this is called LPEV plot. The peaks in this plot show the PEAs. Higher the value of $\lambda p_c$ at the peak, higher the confidence of PEA at around $Lp_c$. Finally, a PEA is reported at a peak with range that covers a contiguous region with $\lambda p_c > T_\lambda = 20$ and centered around the peak.

TRIAGE gene-survival analysis. For each probe set, the mean expression level was first computed for a given cohort. Patients were then stratified into below-mean and above-mean groups, and the Cox proportional hazards regression model was fit to this data to compute a hazard ratio based on distant metastasis-free survival (DMFS). The null hypothesis was that the two groups would have the same risk of recurrence, and the likelihood ratio test p-value was computed as evidence against this hypothesis. Cox model fitting and statistical calculations were performed using the survival package in R. In the case of multiple probe sets mapping to the same gene, the results of the probe set with the most significant association was reported. DMFS was defined as the time interval from surgery until the first distant recurrence event or last date of follow-up. All patients with bilateral and contralateral cancers, and those with recurrence or disease-specific death >10 years post-diagnosis were systematically censored for events. The Uppsala cohort was used to generate the survival data in TRIAGE as it was our largest population-based cohort with longest and most complete patient follow-up.

Figure 10A:
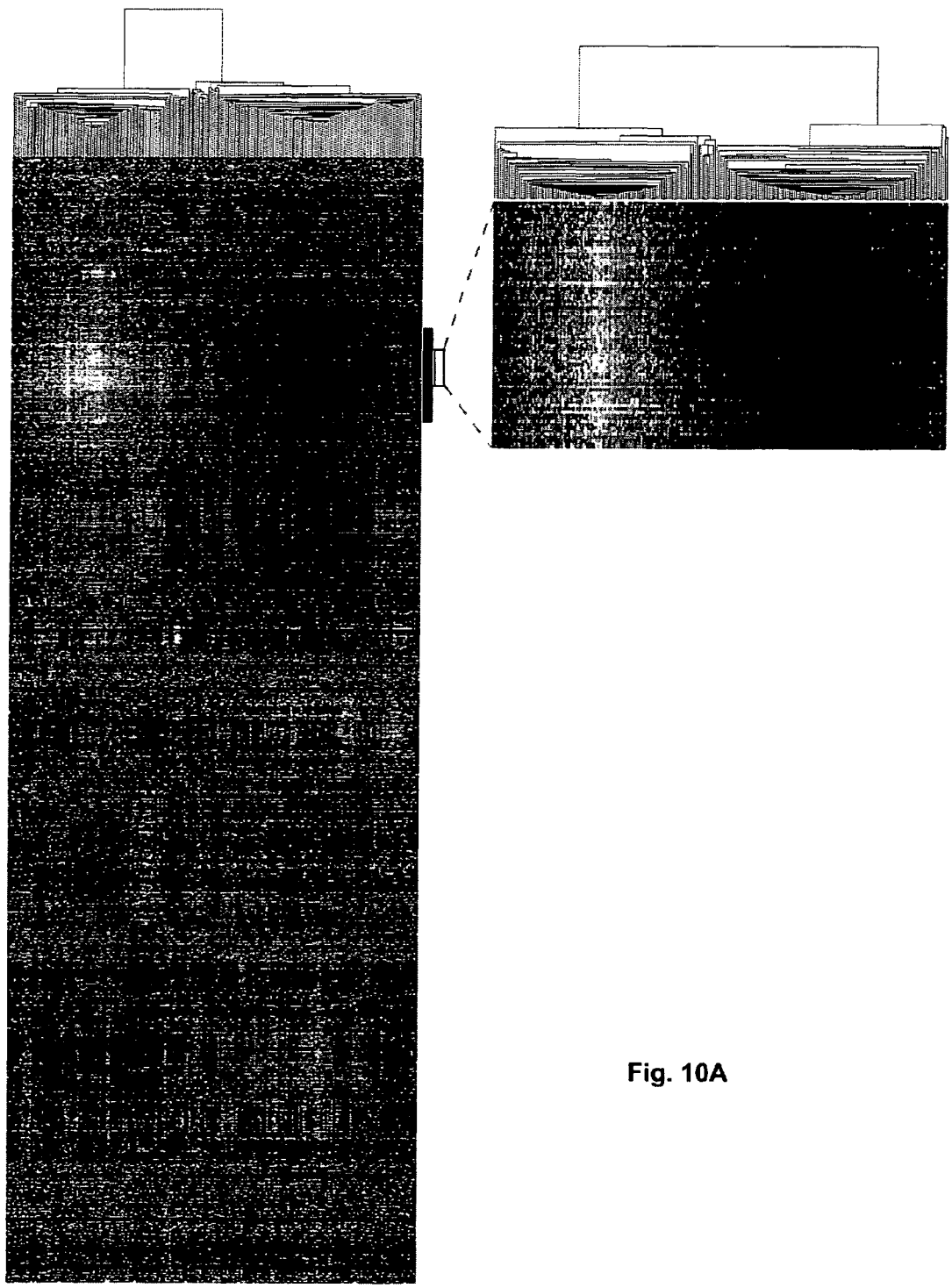
FIG. 10 depicts the derivation of the proliferation signature. 1,134 IMAGE clones identified by Whitfield et al., ((2002) *Mol Biol Cell*, 13, 1977-2000) as cell cycle regulated genes (in HeLa cells) were mapped to 884 UniGene IDs (build #187), corresponding to 2,113 Affymetrix probe sets (U133A and U133B). Using these probe sets, expression profiles of the Uppsala tumor cohort (n=251) were hierarchically clustered (Pearson correlation, average linkage) and visualized in an Eigen clustergram heatmap (left side). White signals in FIG. 10A indicate above-mean expression, white signals in FIG. 10B reflect below-mean expression. The respective degree of brightness reflects the magnitude of expression. (Due to space limitations, the gene dendrograms have been omitted.) The dark bar designates a cluster of genes mostly expressed in G2/M that was previously identified by Whitfield and Perou as being associated with proliferation in human breast tumors. 78 probe sets corresponding to 67 genes of the proliferation cluster had an average correlation of >0.8 (designated by the white bar) and are shown to the right hierarchically clustered. These probe sets (right side) were designated as the core proliferation signature genes, and averaged to derive Pearson correlations between all probe sets and the proliferation signature (i.e., step 6 of TRIAGE).
Figure 10B:
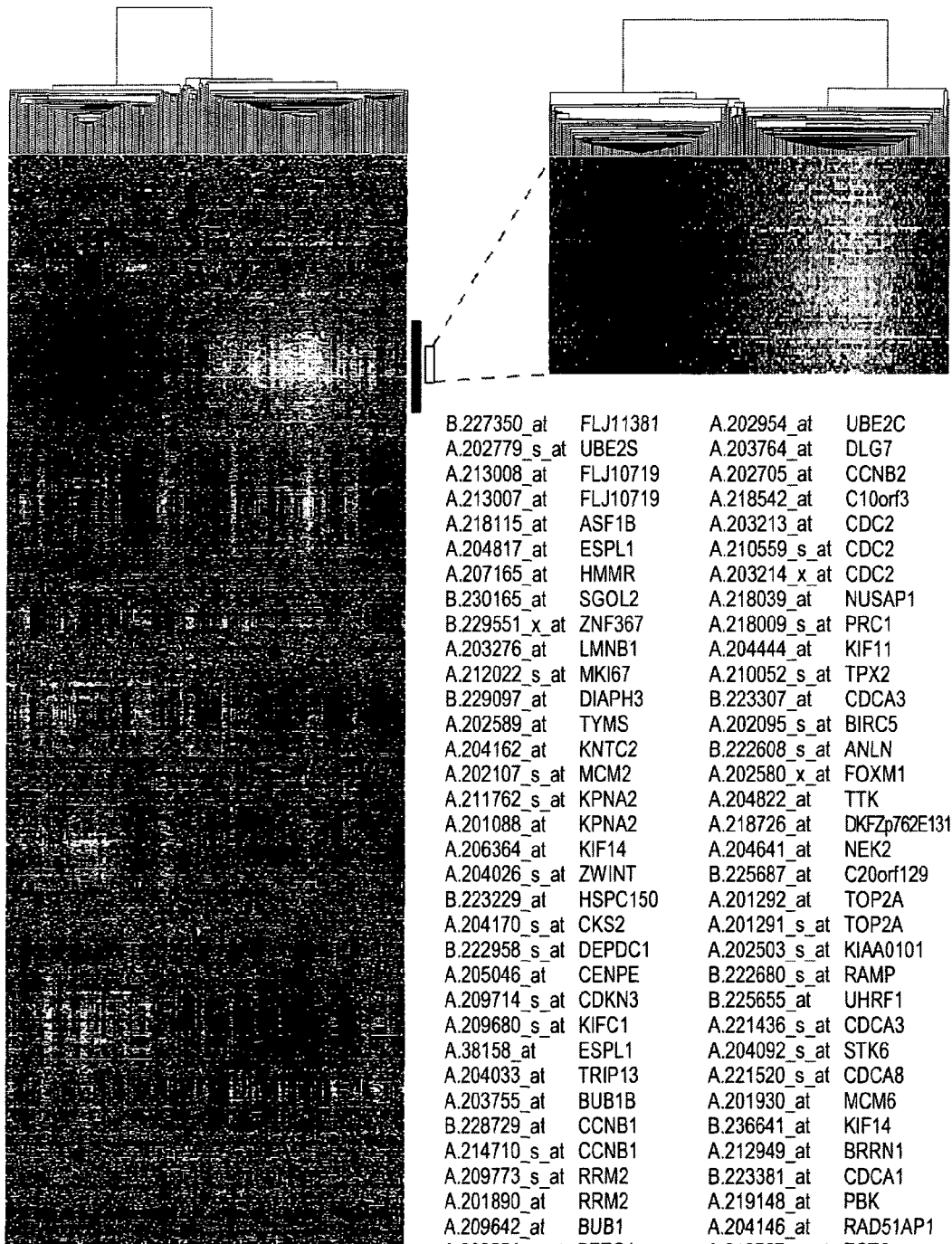

The proliferation signature and gene correlations. Using cDNA Microarrays, Whitfield et al previously identified >850 cell cycle regulated genes in HeLa cervical carcinoma cells (Whitfield, M. L., et al., (2002) *Mol Biol Cell*, 13, 1977-2000). The authors discovered a fraction of these genes that displayed highly correlated expression in breast tumors and were associated with tumor cell proliferation in the Perou et al breast cancer dataset (Perou, C. M., et al. (2000) *Nature* 406, 747-752). To approximate this proliferation signature, we mapped the cell cycle regulated genes (corresponding to 1,134 IMAGE clones in the Whitfield study) to Affymetrix probe sets via UniGene build #187, and hierarchically clustered the Uppsala cohort tumors. A distinctive cluster containing the proliferation associated genes emerged (see FIG. 10) and was found to be highly correlated with markers of proliferation in the Uppsala cohort including histologic grade, mitotic index, and KI67 scores (data not shown). Probe sets central to this cluster having an average correlation of >0.8 (n=78 probe sets corresponding to 67 genes [see FIG. 10]) were designated the "core proliferation signature" genes, and their average expression was used to calculate Pearson correlations between the proliferation signature and all other probe sets for the TRIAGE analysis, step #7. Notably, this step may not be essential for TRIAGE analysis of other cancer types, depending on the clinical association between proliferation and cancer recurrence.

Selection and cloning of RAB11FIP1 (RCP). Three splice variants of RCP were identified in GenBank: variant 1 (NM_025151), variant 2 (NM_001002233) and variant 3 (NM_001002814). Of these, only variants 1 and 3 could be detected consistently in tumor samples and cell lines by RT-PCR (data not shown), and only variant 1 was observed by Western blot with the polyclonal RCP antibody (GenWay). Thus, the full-length variant 1 of RCP was amplified from normal human blood by RT-PCR (forward primer: 5'-ACCATG TCCCTAATGGTCTCGGCT-3' (SEQ ID NO: 1); reverse primer: 5'-TGCTGATTTACA TCTTTCCTCT-3') (SEQ ID NO: 2), sequence verified, and used to investigate RCP function in this study.

Cell lines and transient transfection. Human mammary cell lines, MCF10A, MCF7 and MDA-MB231 were obtained from American Type Culture Collection (ATCC) and maintained at 37° C. with 5% $CO_2$ with growth medium recommended by ATCC. Full-length RCP was ligated into the BamH1 and EcoR1 site of pcDNA3.1. Two RCP-specific RNAi constructs were designed as previously described (Reynolds, A., et al., (2004) *Nat Biotechnol*, 22, 326-330) and manufactured by Ambion. Transient plasmid and RNAi transfection on MCF7 was carried out using Lipofectamine 2000 (Invitrogen) according to the manufacturer's protocol.

Generation of stable cell lines by lentiviral infection. For the generation of cell lines stably overexpressing shRNA, oligonucleotides encoding the target sequence (forward: 5'-TCGATAAGCAAGAAGGAGTTTTCAA-gAgAAACTCCTTCTTGCTTATCGTTTTTTC-3' (SEQ ID NO: 3), and reverse: 5'-TCGAGAAAAAACGATAAGCAA-GAAGGAGTTTCT CTTGAAAACTCCTTCTTGCT-TATCGA-3') (SEQ ID NO: 4) were annealed and cloned into the LentiLox pLL3.7 vector. For control shRNA, a non-targeting "scramble" sequence was cloned into pLL3.7. (forward: 5'-TGAACGGCATCAAGGTGAACttcaa-gagaGTTCA CCTTGATGCCGTTCTTTTTTC-3' (SEQ ID NO: 5), and reverse: 5'-TCGAGAAAAAAG AACGGCAT-CAAGGTGAACTCTCTTGAAGTTCACCT-TGATGCCGTTCA-3') (SEQ ID NO: 6). For overexpression of RCP by lentivirus, RCP was first cloned into the Invitrogen gateway entry vector pENTR3c and further recombined into the lentivirus vector, pLenti6/V5-DEST (Invitrogen) by LR recombination reaction according to the manufacturer's protocol. For lentivirus production, pLL3.7 or pLenti6/V5-DEST was co-transfected with packaging vectors into 293FT cells and the supernatant was harvested after 48 h. Virus was concentrated by ultracentrifugation for 2 h at 25,000 rpm in a Beckman SW28 rotor and resuspended in phosphate-buffered saline. Titers were determined by infecting NIH/3T3 cells with a serial dilution of the concentrated virus. For a typical preparation, the titer was approximately $1-5\times10^8$ particles for pLL3.7 and $4-10\times10^7$ particles for pLenti6/V5-DEST vector. For infection of MCF10A, MCF7 and MB231 cells, $2\times10^8$ cells were incubated in suspension with $1\times10^7$ particles and 8 μg/ml polybrene for 3 h at 37° C. The cells were then re-plated and cultured as previously described. To obtain a pure population of RCP knock-down stable cells, GFP-positive cells were sorted after 4 days of culture. For generating RCP overexpressing stable lines, cells were selected with blastacidin for 2 weeks after infection.

Western blot analysis. Whole cell lysates were prepared using RIPA buffer. The proteins were separated by SDS-PAGE and transferred to Hybond-P PVDF membrane (GE Healthcare). Antibodies to RCP (Genway, Catalog Number (CN): 15-288-21574A), β-actin (Sigma, CN: A5441), phospho-Akt (Cell Signaling Technology, CN: 9271), Akt (Cell Signaling Technology, CN: 9272), phospho-Erk (Cell Signaling Technology, CN: 9101), and Erk (Cell Signalling, CN: 9102) were used to probe the membrane, and antibody-protein complex was detected by HRP-conjugated antibodies and ECL (Amersham Biosciences).

Cell proliferation and colony formation. Cells were plated at a density of 5000 cells/well in 96-well plates, and cell proliferation was measured in quadruplicate (ie, 4 wells per condition) using WST-1 (Roche) according to the manufacturer's protocol. For the MAPK inhibition assays, cells were treated with MEK inhibitor U0126 (Promega) overnight in medium with 0.5% serum before being re-plated into 96-well plates. To test the effect of RCP on anchorage-independent colony formation, cells were suspended in 250 μl of 0.3% agar (Sigma) dissolved in complete medium containing 25 FBS, and plated in quadruplicate (ie, 4 wells per condition) in 24-well plates pre-coated with 500 ul of 0.6% agar base. Colony forming efficiency was examined 21 days or more after plating by staining with Iodonitro-tetrazolium chloride (Sigma). Colonies of size >50 um were counted using Leica QWin software.

In vitro invasion and migration. Transwell migration and invasion assays were performed using Falcon FluoroBlok 24-Multiwell inserts (BD Biosciences) with 8 µm pores. For invasion assays, the inserts were coated with 20 µg Matrigel (BD Biosciences) in 80 µL serum-free growth medium. For both assays, 5000 cells in 200 µL serum-free growth medium were loaded into each transwell insert with 750 µL complete growth medium with 10% fetal bovine serum in the lower chamber. After 24 hours, cells that had migrated or invaded through the pores of the inserts were fixed with 3.7% formaldehyde, stained with 2.5 µg/mL Hoechst 33342 (Invitrogen) for 15 mins, washed with PBS and counted using the Target Activation Bioapplication on an ArrayScan VTI (Cellomics). Field size was 1 mm$^2$. For invasion assays, experiments were performed with 4- to 5-fold replication, with 10-16 fields scanned per experiment. For migration assays, experiments were performed with 3-fold replication, with 10-16 fields scanned per experiment.

Immunofluorescence microscopy of cells. Cell cultures were fixed in 4% para-formaldehyde and permeabilized with 0.25% Triton X-100, followed by blocking with 1% goat serum in PBS. Cells were stained with anti E-Cadherin (BD Pharmingen, CN: 610404) and fibronectin antibody (BD Pharmingen, CN: 610077) at 1:500 dilution, followed by the appropriate secondary antibodies detecting mouse and rabbit IgG conjugated with Alexa Fluor 594 or 488 (Molecular Probes), respectively. F-actin was labeled with Texas Red-X phalloidin (Molecular Probes). DAPI was used to stain the nucleus. Images were captured with a confocal microscope (LSM 510 META, Zeiss).

Cell cycle analysis. MCF10A cells were starved in 1% serum for 48 h. Cells were then fixed in 75% ethanol, treated with RNase A (0.25 mg/ml), stained with propidium iodide (10 ng/ml) and analyzed on a LDR2 flow cytometer (BD Biosciences). Sorted cells was analyzed using FACS DiVa software (BD Biosciences).

Apoptosis assay. MB231 cells were maintained in complete medium or starved with 1% serum for 48 h. Apoptotic cells were detected with the In Situ Cell Death Detection Kit (Roche). Cells with DNA strand breaks were labeled with TMR (red) by TUNEL (TdT-mediated dUTP nick end labeling) reactions and analyzed by fluorescence microscopy and flow cytometry.

Tumorigenicity in nude mice. Female BALB/c-nu/nu (nude) mice 6-8 weeks old were housed under pathogen-free conditions in a temperature controlled room on 12/12 h light/dark schedule with food and water ad libitum. All procedures involving animals and their care were in accordance with national and international regulations. For MCF-7 tumor formation experiments, a 1.7 mg 17β-estradiol pellet (90-day release, Innovative Research of America) was implanted in each mouse 1 week prior to tumor cell injection to supplement the estrogen requirements of MCF-7 cells. The experimental groups were: MCF7-RNAi RCP (stable RCP knock down), MCF7-RNAi Ctrl (control), MB231-RNAi RCP, MB231-RNAi Ctrl. For each experimental group, 8 mice were injected subcutaneously (above the right and left hind legs) with 2.0×10$^6$ cells. Subcutaneous tumors were measured with a digital caliper once a week. Tumor volume was calculated as ab$^2$/2 in mm$^3$, where a and b are the longest and the shortest perpendicular diameters of the tumor, respectively. Tumor weights were taken at termination and mice were killed in compliance with Singapore animal holding rules.

Immunohistochemistry. Four µm thick paraffin-embedded tumor tissue sections were stained using ABC immunohistochemistry reagents and avidin-biotin blocking reagents (Vector Laboratories) according to the manufacturer's protocols. The slides were incubated with anti-RCP antibody at a 1:500 dilution and counterstained with hematoxylin.

Results

The above data demonstrates that the coordinate analysis of genomic, transcriptomic and clinical information can successfully direct the discovery of novel genes in cancer that likely contribute to metastatic recurrence and patient death, thereby facilitating the rational prioritization of genes for downstream functional investigations. The exemplary validation of RAB11FIP1 as a multifunctional and frequently occurring oncogene in human breast cancer underscores its importance as a therapeutic target and provides new insight into the emerging role of endocytic recycling pathways in carcinogenesis.

For illustration purposes, a functionally validation of RAB11FIP1, located on chromosome 8p11, as a novel oncogene with multiple pathological roles in breast tumorigenesis is herein provided. RAB11FIP1 was previously identified as the Rab4 and Rab11 interacting protein, also called Rab coupling protein (RCP), which functions in endosomal recycling and receptor sorting (Lindsay, A. J., et al. (2002) *J Biol Chem* 277, 12190-12199; Peden, A. A., et al. (2004) *Mol Biol Cell* 15, 3530-3541). Though dysregulation of RAB11 and RAB25 expression has been implied as a generalized component of many human tumors (see e.g. Cheng, K. W., et al. (2004) *Nat Med* 10, 1251-1256; Cheng, K. W., et al. (2005) *Methods Enzymol* 403, 202-215; Gebhardt, C., et al. (2005) *Am J Pathol* 167, 243-253; Goldenring, J. R., et al. (1999) *Yale J Biol Med* 72, 113-120; Yoon, S. O., et al. (2005) *Cancer Res* 65, 2761-2769), a role for Rab interacting proteins in tumor progression has not been described. The present inventors devised an integrated analytical strategy for triangulating critical oncogenes in cancer forms through clinical and genomic intersects, which takes into account expression frequency, coexpression in an amplicon, association with patient disease-free survival, and which discounts fortuitous association with tumor proliferation. Using this multi-step data mining approach, abbreviated TRIAGE (Triangulating Oncogenes through Clinico-Genomic Intersects, see below), the present inventors have identified RAB11FIP1 as an oncogene.

Oncogene Deduction by TRIAGE

To identify oncogenes contributing to aggressive breast cancer, it was hypothesized that a particular subset of such genes might be discovered through triangulation of transcriptomic, genomic and clinical information. Specifically, the inventors sought to uncover oncogenes that are: 1) located in regions of recurrent amplification, 2) activated by gene dysregulation, and 3) associated with metastatic dissemination of cancer. To this end, we developed a multi-step data mining approach termed TRIAGE (Triangulating Oncogenes through Clinico-Genomic Intersects), that identifies expression footprints of recurrent genomic amplicons in expression microarray data, relates gene expression to risk of metastatic recurrence, and evaluates the candidacy of genes based on survival correlations and comparative mRNA dynamics (FIG. 1).

Figure 3:
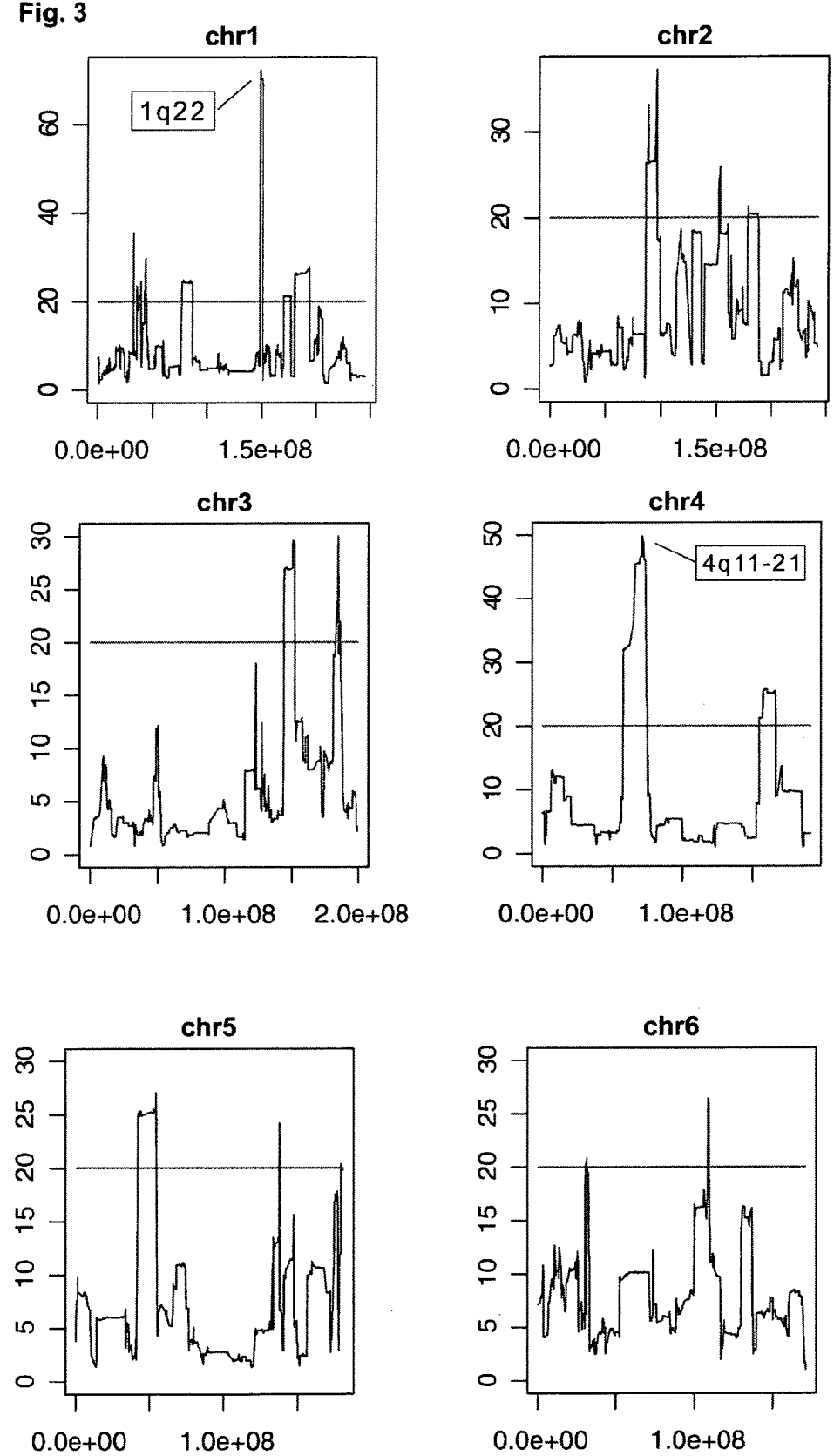
FIG. 3 depicts the LSVD analysis of the breast cancer oncogenome. Eigen values (y-axis) are plotted along the length of each chromosome (x-axis). The genomic locations of the highest-scoring principle eigen peaks are highlighted.
Figure 3:
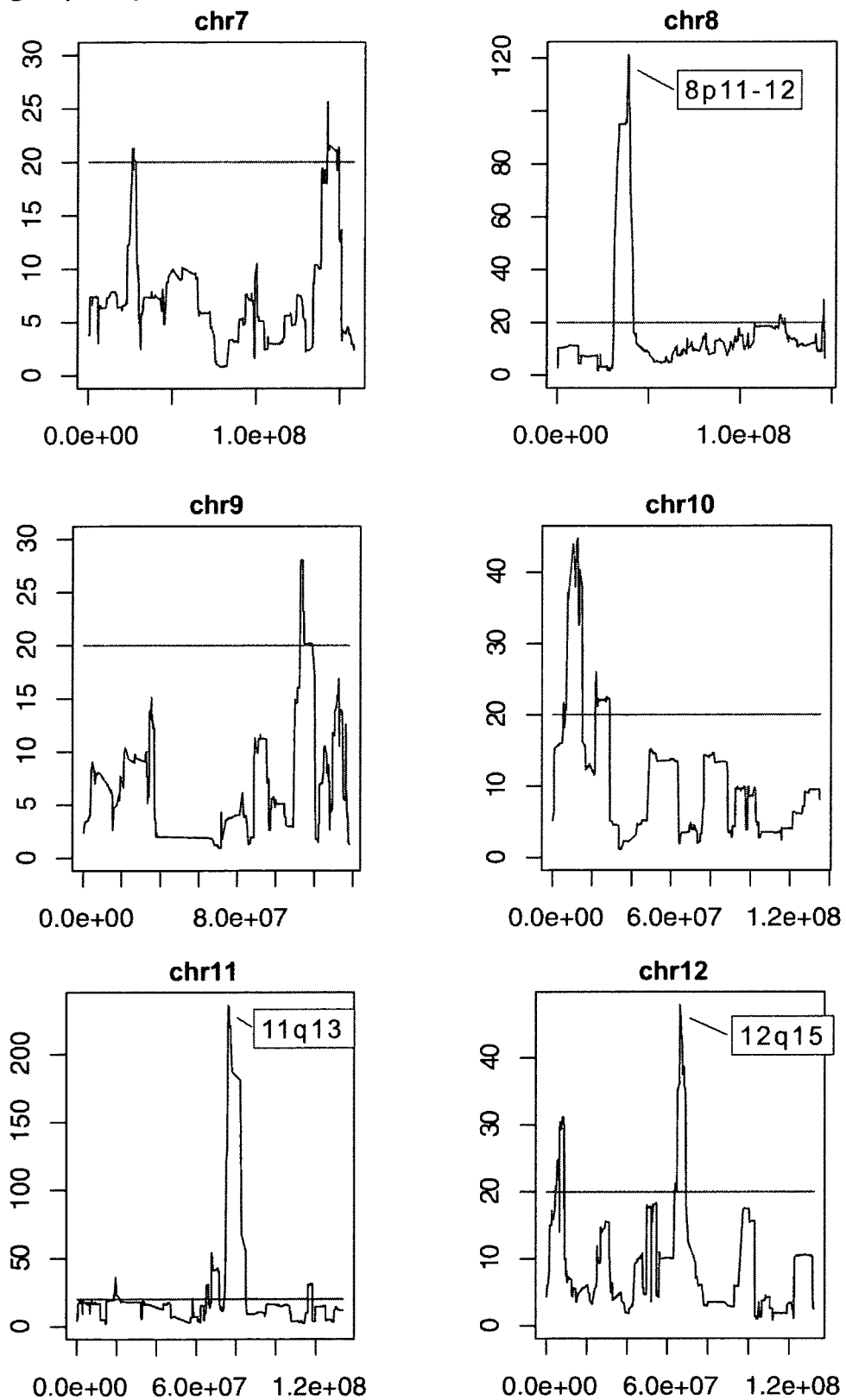
Figure 3:
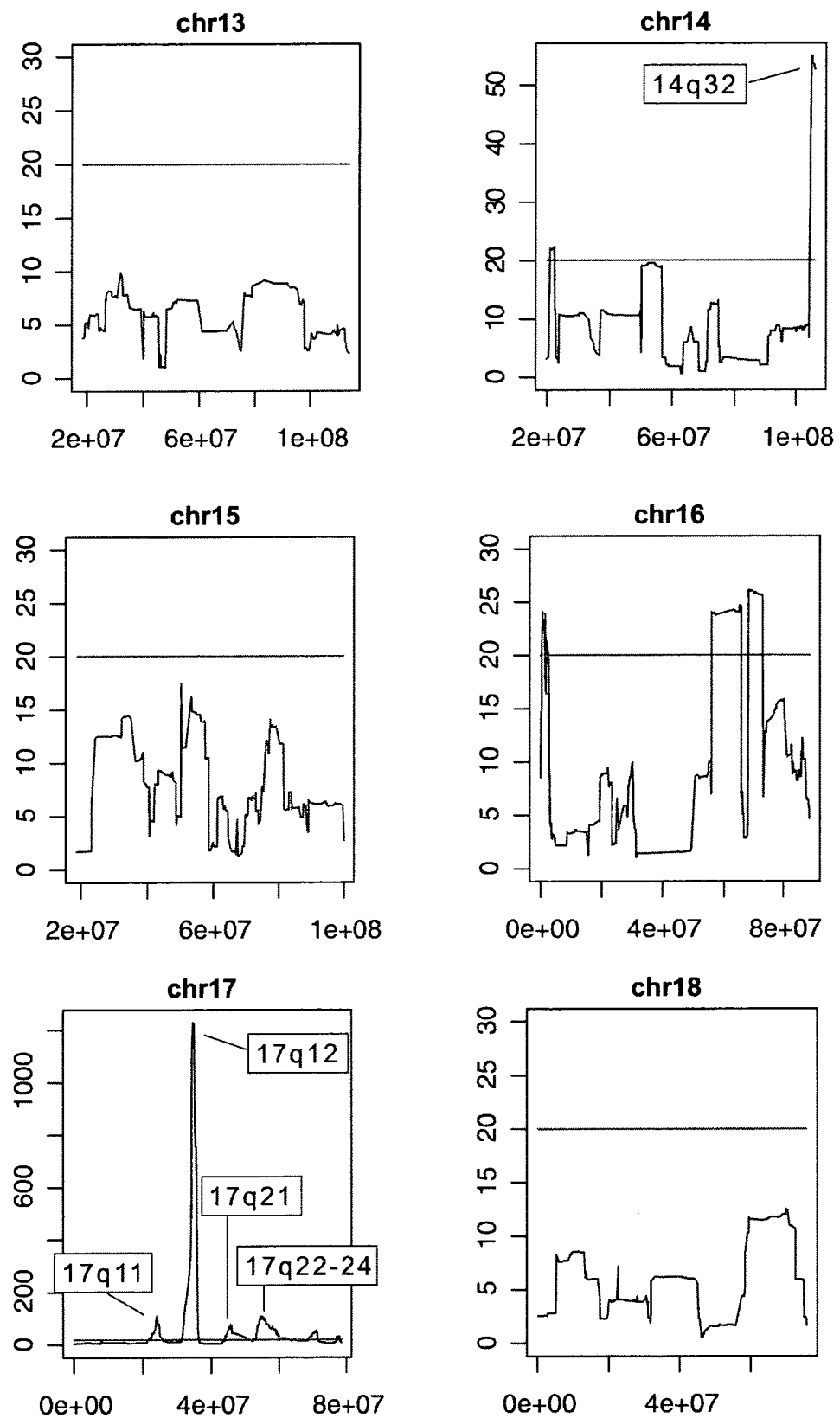
Figure 3:
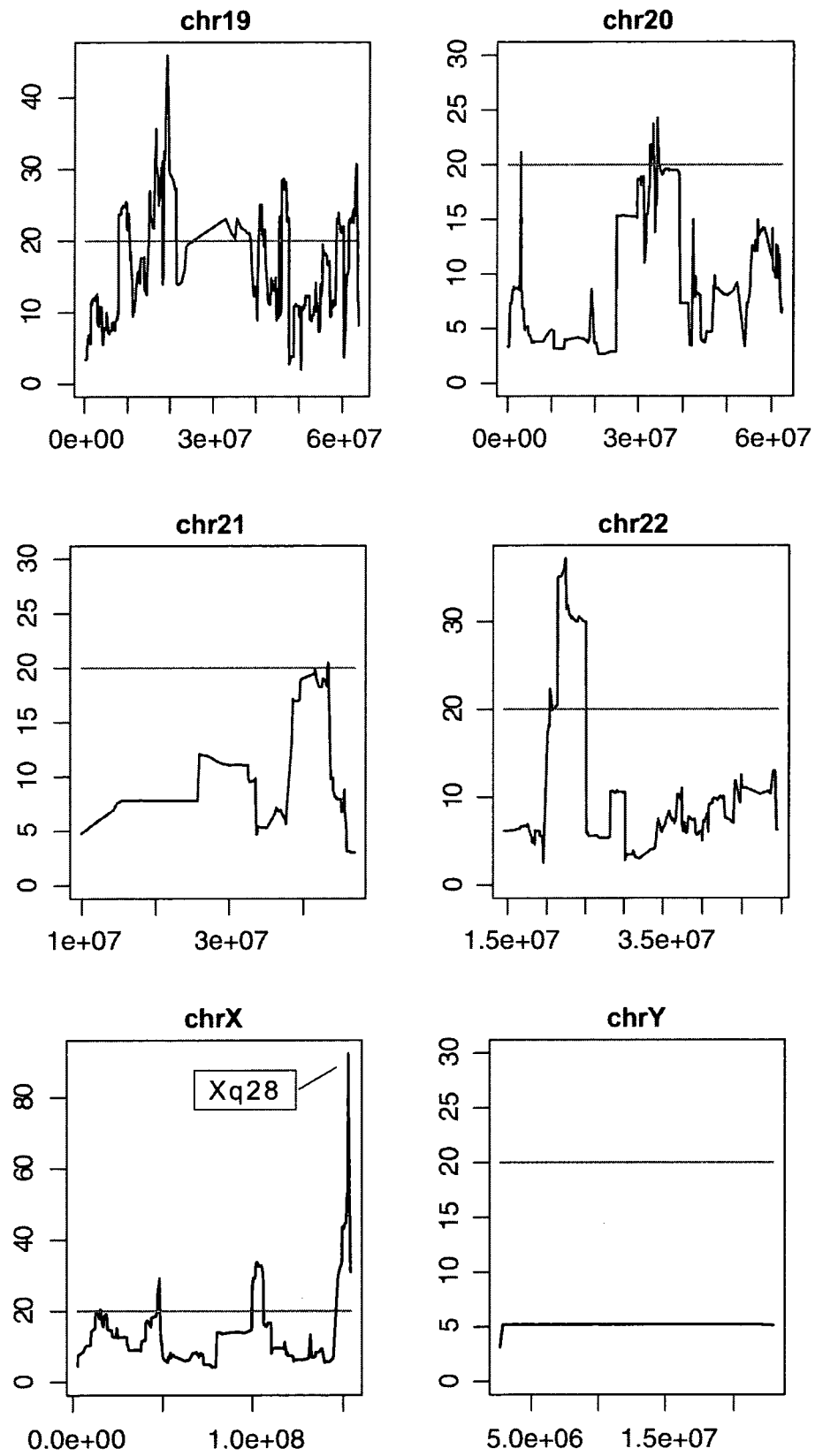

In the first step, microarray expression profiles of 737 primary invasive breast tumors (FIG. 2) were analyzed by Local Singular Value Decomposition (LSVD) to infer the presence and location of recurrent genomic amplicons. This approach is based on the premise that recurrent amplicons can be detected by the coordinate overexpression of involved genes (Chin, K., et al. (2006) *Cancer Cell* 10, 529-541; Reyal, F., et al. (2005) *Cancer Res* 65, 1376-1383), and is supported by evidence that the majority of highly amplified genes in breast cancer are concurrently overexpressed (Pollack, J. R., et al., (2002) *Proc Natl Acad Sci USA*, 99, 12963-12968). LSVD allows for the simultaneous identification of genomic loci enriched for gene overexpression, and the fraction of tumors where "locus-specific" overexpression occurs. The output is viewed as principal eigen peaks that reflect both the degree of locus-specific overexpression and the number of tumors involved. The highest-scoring principal eigen peaks discovered by whole-genome LSVD mapped predominantly to loci corresponding with known regions of recurrent copy number gain (see FIG. 3). Though not all peaks identified by LSVD would be expected to represent recurrent amplification events, those with high magnitude and precise genomic overlap with known recurrent amplicons were termed probable expression amplicons (PEAs), and were further investigated by the TRIAGE process.

Based on the precept that the expression level of an oncogene of interest would correlate with poor patient outcome, genes within PEAs were assessed for significant associations with distant relapse. For each gene, tumors (and corresponding patients) were dichotomized into low expression (below mean) or high expression (above mean) groups and analyzed by Cox proportional hazards regression for distant metastasis-free survival (DMFS) (FIG. 1, steps 2&3). Likelihood ratio test P-values reflecting the significance of the resulting hazard ratios were used as an initial measure of the oncogenic potential of the PEA genes (FIG. 1, step 3, unselected survival). However, since recurrent genomic amplicons may correlate with poor patient survival, benign "passenger genes" physically present on the amplicon may also correlate with poor DMFS without functionally contributing to tumor aggression, whereas the driving oncogenes (which may be activated in cancer by mechanisms other than copy number gain) would be expected to remain correlated with poor DMFS in tumors lacking the amplicon, while passenger genes would not. Therefore, the correlations between gene expression and DMFS with the amplicon-containing tumors censored from the analysis were re-examined (FIG. 1, step 4, selected survival). In this manner, only those candidate oncogenes robustly associated with poor DMFS independent of an amplification event will emerge.

Candidate oncogenes significant at both steps of survival analysis were further scrutinized through comparisons of mRNA expression patterns (FIG. 1, steps 5&6). Following the assumption that the driving oncogenes should be relatively highly and consistently expressed in amplicon-containing tumors, the expression levels of genes within PEAs were averaged, and the genes were subsequently ranked by mean expression (where a rank of 1 denotes the highest average expression level). In this way, the expression ranking serves as an additional relative gauge of oncogenic potential at a given locus.

Figure 4A:
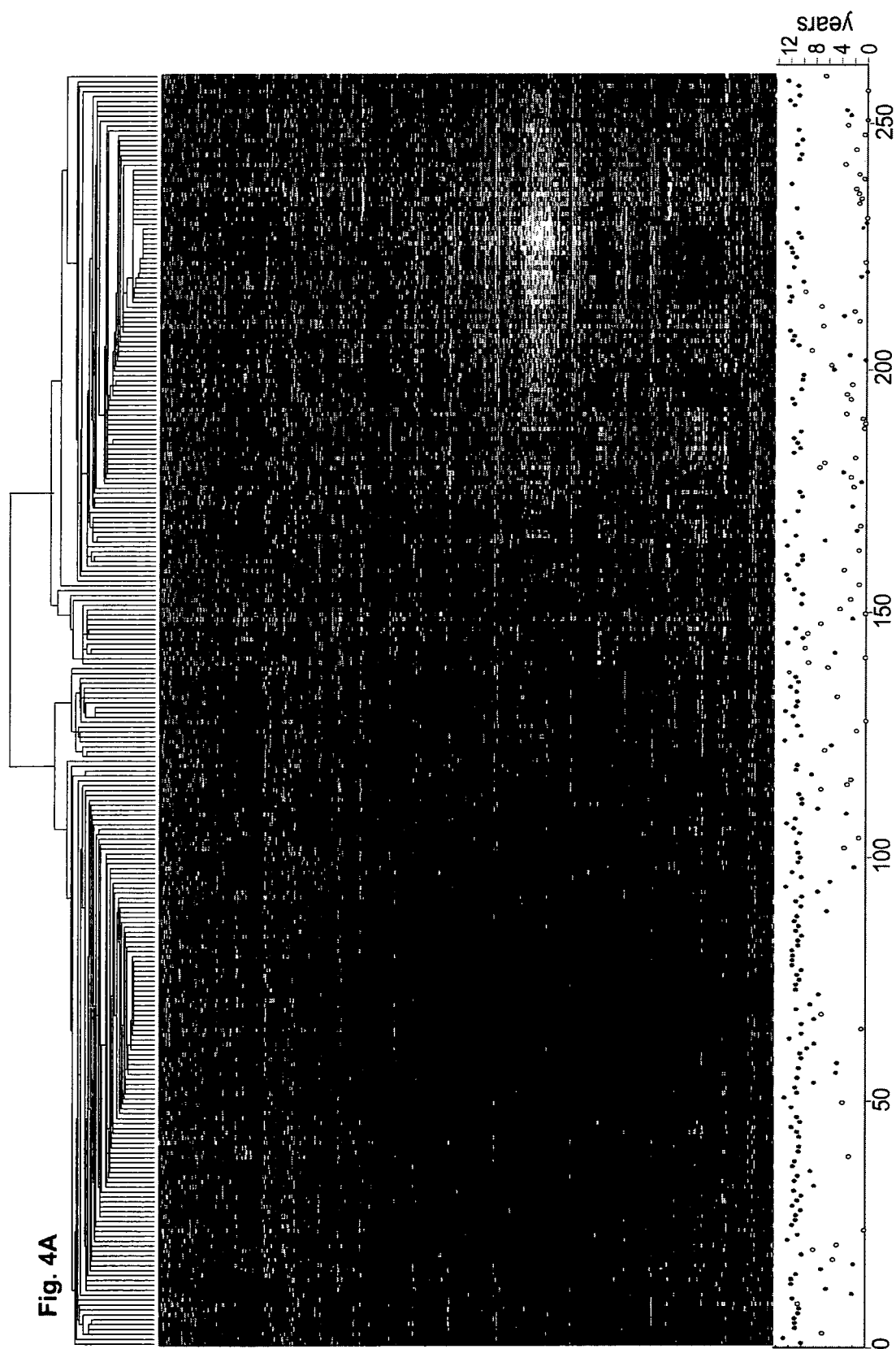
FIG. 4 shows the proliferation signature and distant metastasis-free survival (DMFS). A,B: All probe sets (n=2, 377) correlated with poor DMFS (P<0.05; likelihood ratio test) in the Uppsala cohort (n=251) are shown hierarchically clustered. The predominant gene cluster reflects the proliferation signature. The central core genes of the proliferation signature are, in clustered order are named in the examples below. Below the clustergram, tumors that metastasized (white circles) and did not (dark circles) are shown as a function of time. C: Probe sets associated with poor DMFS (n=2,377) were binned according to P-value and the fraction of probesets correlated with the proliferation signature at >0.4 are indicated in white and shown as a percentage of each bin. Approximately 35% of all DMFS-associated probesets are correlated with the proliferation signature at >0.4.
Figure 4B:
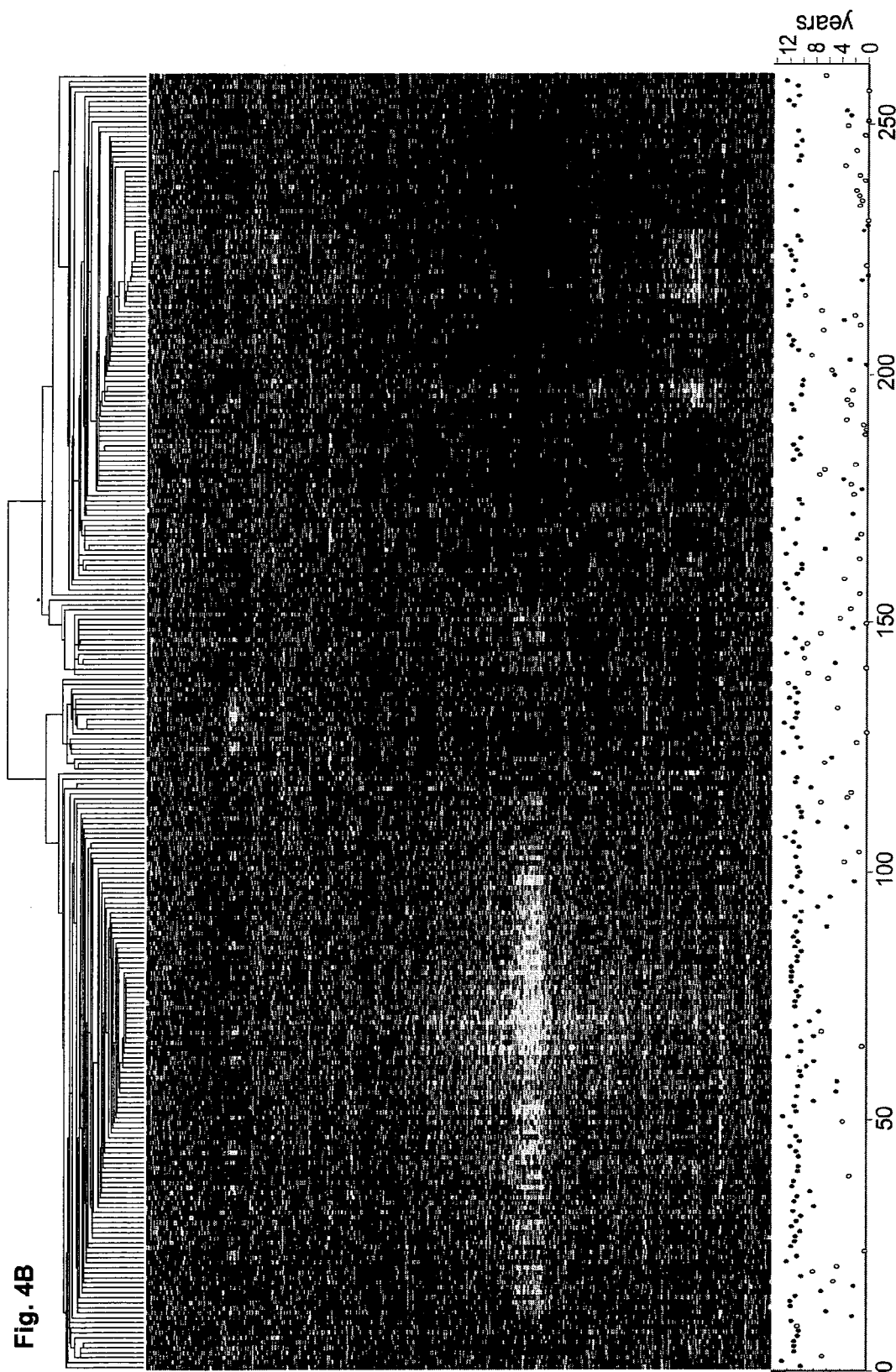

Highly proliferative breast tumors are more likely to relapse, and genes associated with proliferation are often correlated with poor DMFS. This is exemplified in the proliferation signature comprised of many hundreds of highly correlated genes enriched for cell cycle functions, and which has been found to be positively correlated with recurrence of many cancer types (Dai, H., et al., (2005) *Cancer Res* 65, 4059-4066; Ivshina, A. V., et al., (2006) *Cancer Res* 66, 10292-10301; Perou, C. M., et al., (2000) *Nature* 406, 747-752; Rosenwald, A., et al. (2003) *Cancer Cell* 3, 185-197; Whitfield, M. L., et al., (2002) *Mol Biol Cell* 13, 1977-2000; Whitfield, M. L., et al., (2006) *Nat Rev Cancer* 6, 99-106). As in the search was for genes with unique contributions to oncogenesis independent of association with proliferation, in the final step of TRIAGE, the expression patterns of candidate genes were examined for correlation with the proliferation signature to consider the extent to which survival associations might be explained by tumor proliferation rate. Probe sets in the Uppsala breast tumor cohort (n=251 tumors) correlating with poor DMFS are depicted in FIG. 4. Of the 2,377 probe sets found to be significantly correlated with poor DMFS ($p<0.05$), ~35% were also found to be members of this proliferation signature at a Pearson correlation of >0.4 (see FIG. 4). The central core genes of the proliferation signature are, in clustered order: B.222958_s_at DEPDC1, A.204170_s_at CKS2, B.222680_s_at DTL, A.209680_s_at KIFC1, A.202503_s_at CSNK1G1, A.201291_s_at TOP2A, A.201292_at TOP2A, A.204033_at TRIP13, B.225687_at FAM83D, A.200853_at H2AFZ, A.213911_s_at H2AFZ, A.203362_s_at MAD2L1, B.228729_at CCNB1, A.214710_s_at CCNB1, A.203755_at BUB1B, B.228323_at CASC5, A.204825_at MELK, A.204822_at TTK, A.207828_s_at Unknown, A.202870_s_at CDC20, A.222039_at LOC146909, A.204962_s_at CENPA, B.228273_at Unknown, A.209408_at KIF2C, A.202705_at CCNB2, A.222077_s_at RACGAP1, A.218542_atCEP55, A.203213_at CDC2, A.203214_x_at CDC2, A.210559_s_at CDC2, A.218039_at NUSAP1, A.218009_s_at PRC1, A.204444_at KIF11, A.210052_s_at TPX2, A.219918_s_at Unknown, A.203764_at DLG7, B.223307_at CDCA3, A.202095_s_at BIRC5, A.202954_at UBE2C, A.202580_x_at FOXM1, A.218726_at DKFZp762E1312, A.203554_x_at PTTG1, A.209642_at BUB1, A.209773_s_at RRM2, A.201890_at RRM2, A.204641_at NEK2, A.218355_at KIF4A, A.208079_s_at Unknown, A.204092_s_at AURKA, A.38158_at SP1 and A.218755_at KIF20A. As approximately one third of the probe sets significantly correlating with poor DMFS were identified to be members of the proliferation signature, in breast cancer, approximately one in three poor survival-associated genes may be best explained by association with proliferation, rather than an independent oncogenic mechanism. We therefore de-prioritized or discounted candidate genes with significant survival associations yet correlated with the proliferation signature (at >0.4) in the selection process.

Figure 5E:
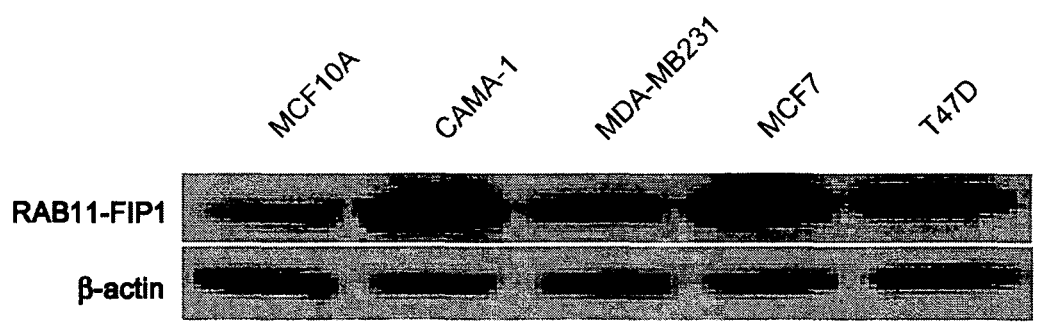
FIG. 5E summarises the obtained data. NS indicates "not significant". Asterisks indicate >0.4 correlation with the proliferation signature. Black vertical bars above the heatmap in panel A denote ERBB2 (HER2/neu) positivity by immunohistochemistry.

To test the validity of this analytical approach, TRIAGE was applied to the principal eigen peak of greatest magnitude identified by whole-genome LSVD. This corresponded to a 1 Mb region on chromosome 17q12 encompassing about 30 genes. The gene components of this PEA mapped precisely to the well-characterized 17q12 amplicon housing the EGFR-related oncogene ERBB2 (HER2/neu) and known to occur in ~20-30% of breast cancer cases. Notably, the expression footprint of this amplicon has previously been observed in microarray studies and shown to correlate well with the boundaries of the physical amplicon as discerned by array-CGH (Chin et al., 2006, supra; Pollack et al., 2002, supra). In tumors exhibiting this PEA, we found a strong enrichment for HER2 positivity by immuno-histochemistry ($P<1.0\times10^{-26}$; Chi-square test), consistent with the evidence that this PEA corresponds with the physical 17q12 amplicon (FIG. 5A, FIG. 5C, black vertical bars). Initial (unselected) gene-survival analysis identified 6 genes within this PEA significantly associated with DMFS (FIG. 5A). Upon re-analysis of survival in the absence of patients with tumors harboring the PEA (ie, selected survival), only 2 genes remained significantly associated with DMFS: TCAP and ERBB2. While neither was strongly correlated with the proliferation signature, ERBB2 had the highest expression ranking (FIG. 5E).

Thus, TRIAGE identified ERBB2 (encoding the precursor of receptor tyrosine-protein kinase erbB-2) as a "top candidate" oncogenic driver at the 17q12 locus, independent of its known roles as a metastasis-promoting oncogene and therapeutic target in breast cancer.

A second large principal eigen peak identified by LSVD mapped to the p-arm of chromosome 8 to a region spanning 1.5 Mb and encompassing 22 genes. This PEA was found to precisely overlap at the gene level with the previously described 8p11-12 amplicon known to occur in 10-25% of breast cancers (Garcia, M. J., et al., (2005) *Oncogene* 24, 5235-5245; Gelsi-Boyer, et al., (2005) *Mol Cancer Res* 3, 655-667; Letessier, A., et al. (2006) *BMC Cancer* 6, 245; Ray, M. E., et al., (2004) *Cancer Res* 64, 40-47). The oncogenic drivers of this amplicon have not been well characterized. By TRIAGE, we identified 3 genes on this amplicon significantly associated with increased risk of distant metastasis: RAB11FIP1, EIF4EBP1, and WHSC1L1 (FIG. 5B). Upon analysis for selected gene-survival correlations, only two genes remained significantly associated with distant metastasis, RAB11FIP1 and WHSC1L1 (encoding Histone-lysine N-methyltransferase NSD3), with RAB11FIP1 having the most significant association with distant recurrence and highest expression rank (FIG. 5E). Based on this finding, we investigated the functional impact of RAB11FIP1 on oncogenic properties of breast cancer.

RCP Overexpression Transforms MCF10A Cells

To verify if RAB11FIP1 (herein also referred to as RCP) is amplified in mammary tumors at the protein level, western blot analysis was performed on a panel of cell lines with different grades of tumor progression using a commercially available antibody. RCP was the lowest in the non-tumorigenic (normal) mammary epithelial cell line MCF10A, but was expressed at 4- to 10-fold higher levels in the breast cancer cell lines CAMA-1, MDA-MB231, MCF7 and T47D (FIG. 6A).

Figure 6B:
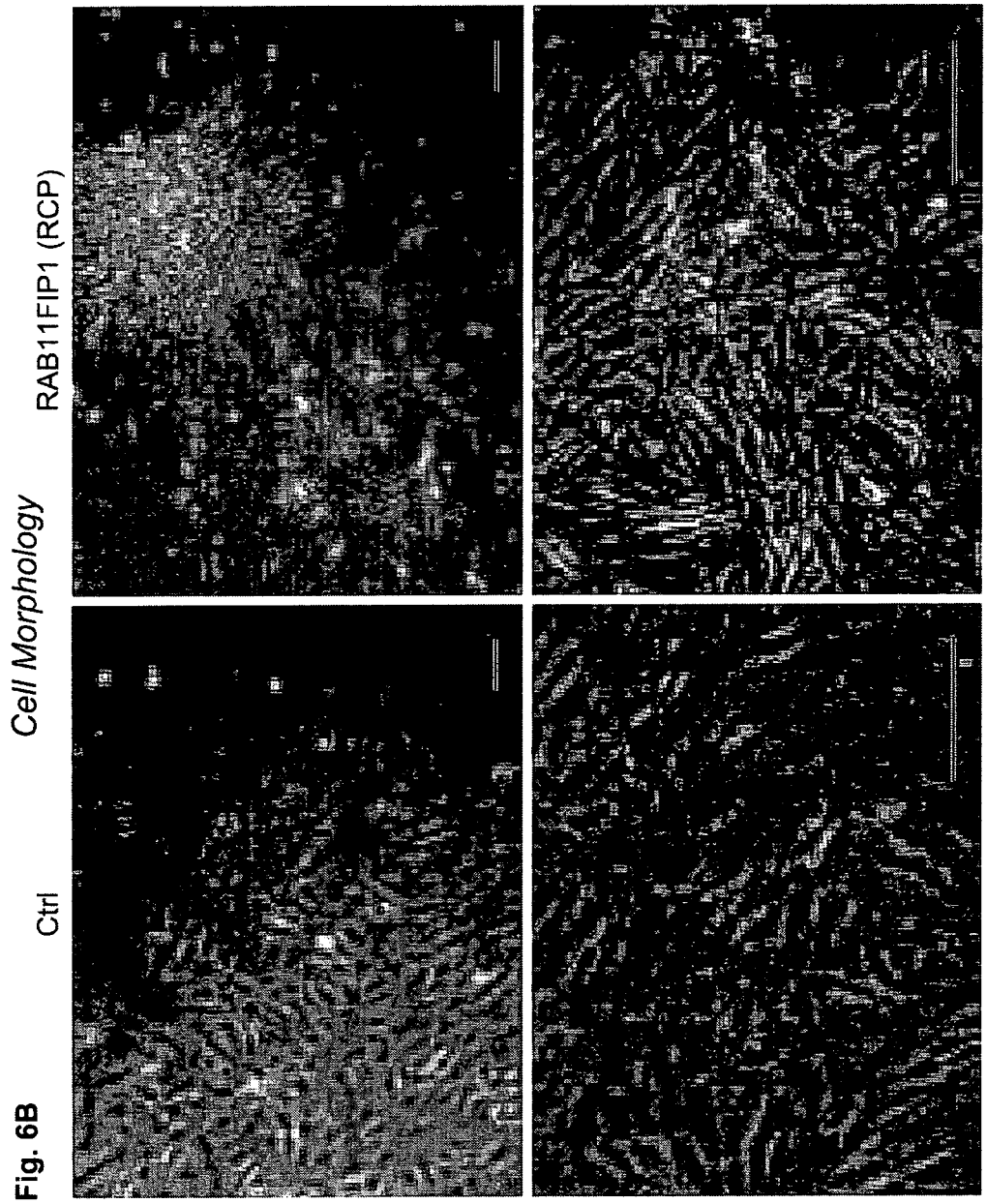
FIG. 6 illustrates that RCP overexpression in MCF10A cells induces oncogenic phenotypes. A: Endogenous RCP levels assessed by Western blot in MCF10A and breast cancer cell lines. B: Impact of RCP overexpression on cell morphology. (Scale bars, 100 µm.). C: Effects of RCP overexpression on localization of E-cadherin at cell-cell junctions (top), organization of F-actin (middle) and expression of fibronectin under serum starvation (bottom) by immunofluorescence. (Scale bars, 50 µm.) D-F: Effects of RCP overexpression on (D) growth factor-independent proliferation of MCF10A cells by WST assay (mean+/−s.d.), (E) anchorage-independent colony formation in soft agar (magnification, 5×), and (F) cell migration by wound healing (scratch) assay. (Scale bars, 100 µm.)
Figure 6C:
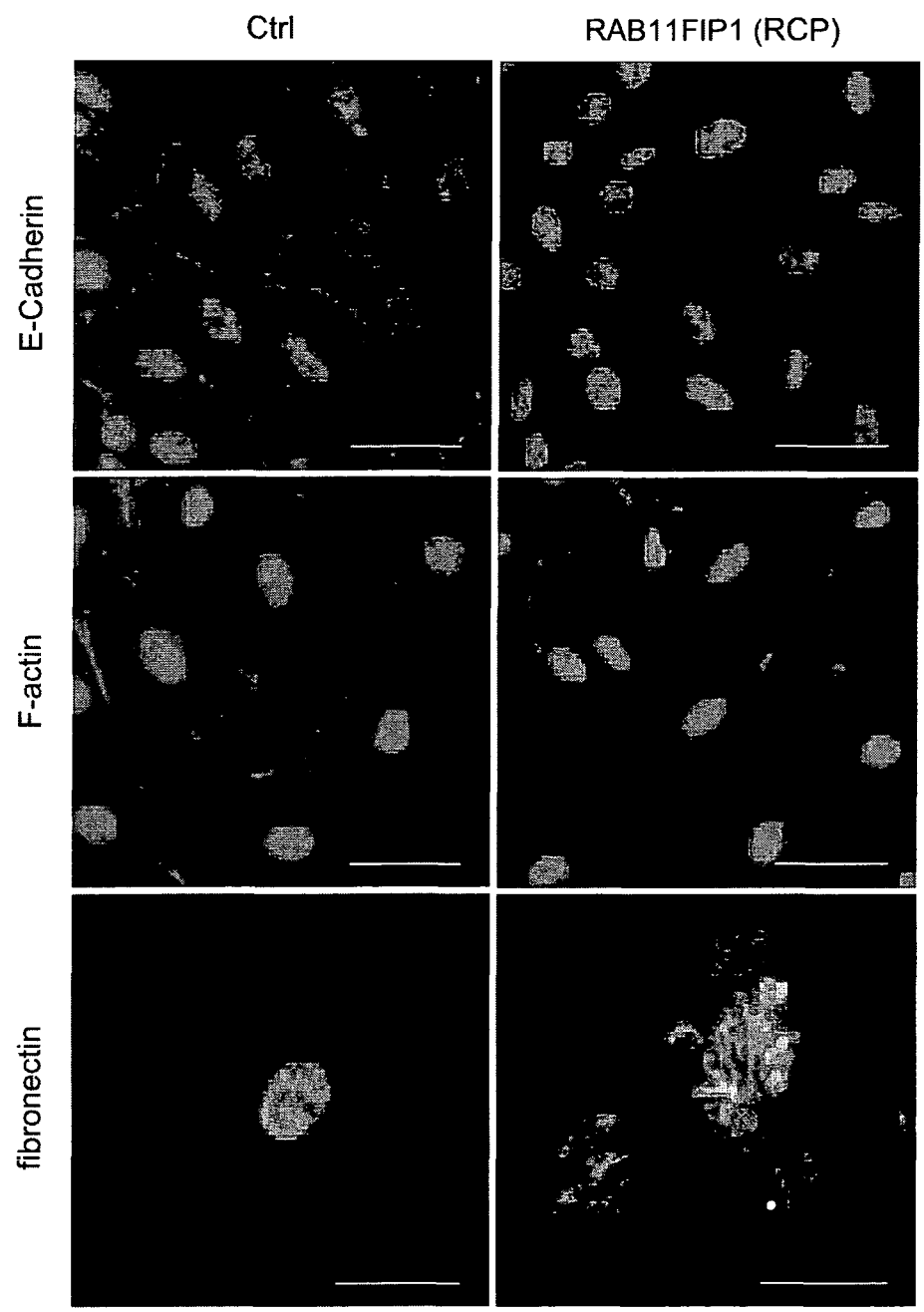
Figure 6F:
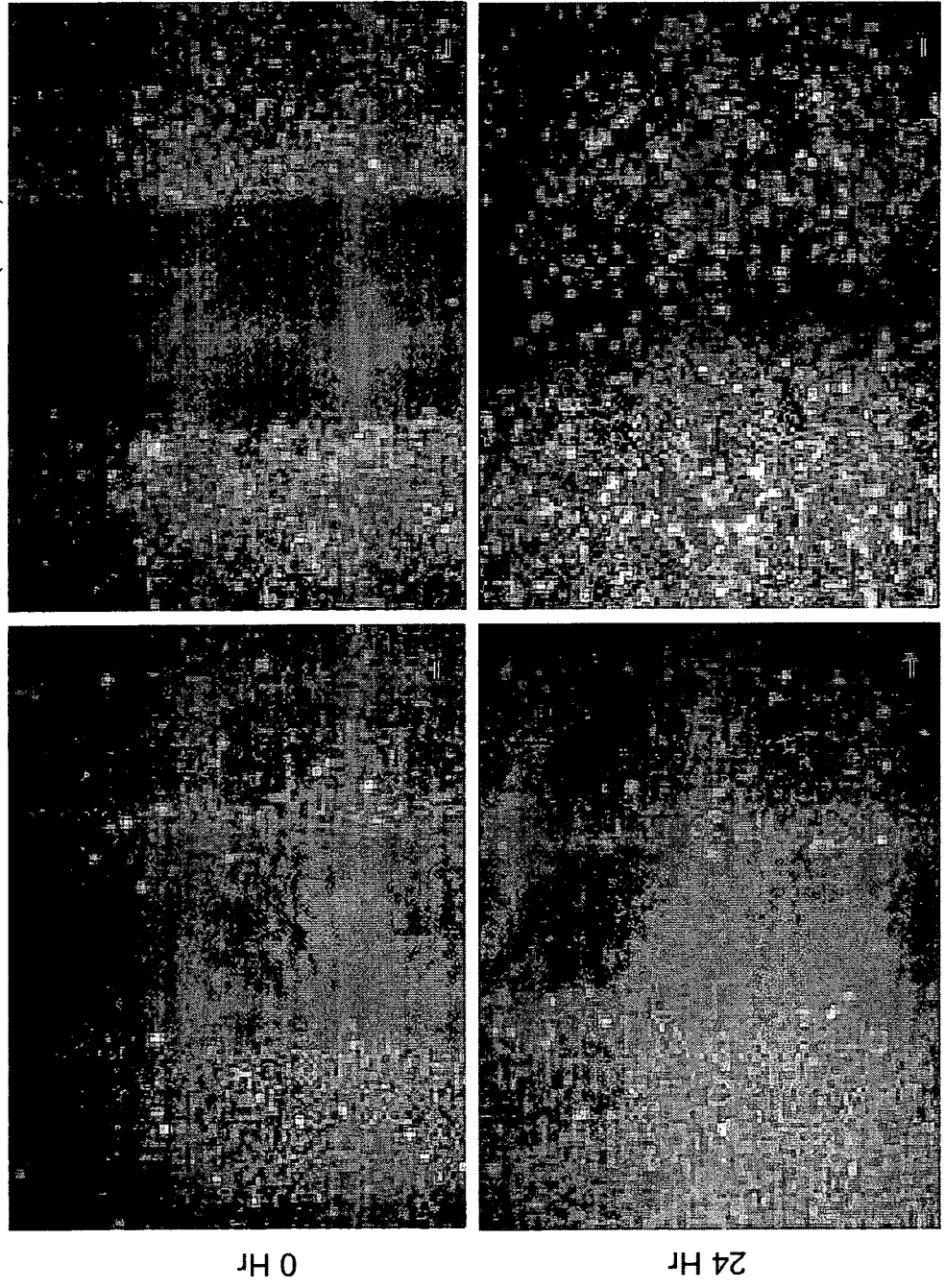

Next the role of RCP amplification in breast cancer was investigated by establishing MCF10A cell lines stably overexpressing full length RCP (MCF10A-RCP) (Genbank Accession: NM_025151) or the control vector. While the control cells exhibited a flattened morphology and monolayer growth characteristic of normal epithelium (FIG. 6B; left panels), RCP overexpression resulted in dramatic morphological changes, including spindle-like projections and a scattered growth pattern occasionally interspersed with foci-like formations reminiscent of transformed fibroblasts (FIG. 6B; right panels). The control MCF10A cells, on the other hand, exhibited a flattened morphology and monolayer growth in epithelial-type islands—more characteristic of normal epithelium. Furthermore, at confluence, the MCF10A RCP overexpressing cells displayed loss of contact inhibition and exhibited continuous multilayer growth. Immunofluorescent staining of cells revealed that RCP overexpression was associated with loss of E-cadherin at cell-cell junctions and disorganization of beta-actin. Additionally, fibronectin was observed to be more abundant in MCF10A-RCP cells than control cells under serum starvation conditions (FIG. 6C). Loss of E-cadherin at sites of cell-cell contact (an epithelial marker) and increased expression of fibronectin (a mesenchymal marker) are both consistent with an RCP-dependent epithelial to mesenchymal (EMT) transition.

Figure 7A:
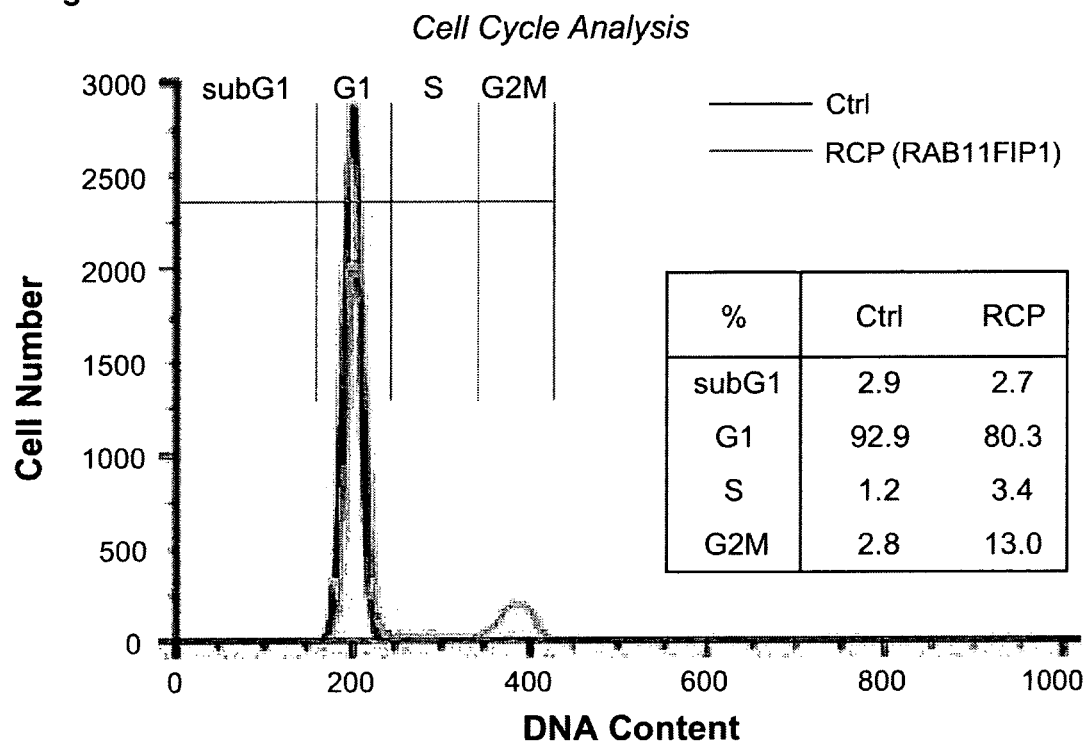
FIG. 7 illustrates the mechanisms of RCP action. A: Cell cycle analysis of serum-starved MCF10A-RCP and control cells by flow cytometry. B: Western blots showing Erk and Akt phosphorylation status in response to RCP overexpression (MCF10A cells) and RNAi-mediated knock down of RCP (MCF7 cells). C: Inhibition of RCP-mediated Erk phosphorylation by the MAPK inhibitor, U0126 (upper panel), and D: U0126-mediated inhibition of the RCP proliferation phenotype (lower panel; mean +/−s.d.).
Figure 8A:
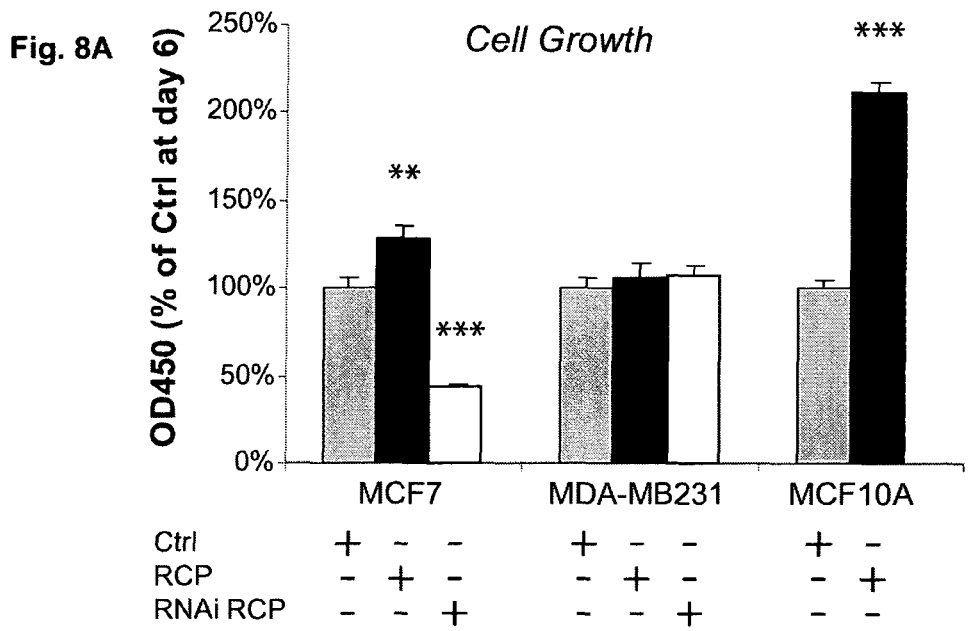
FIG. 8 shows oncogenic phenotypes of RCP in breast cancer cell lines. A: Effects of RCP overexpression and RNAi-mediated knock down of RCP on cell proliferation by WST assay. Left panel, results at 6 days post-transfection. Middle panel, proliferation time course of RCP overexpression in MCF10A cells. Right panel, proliferation time course of RCP inhibition in MCF7 cells using two different RNAi RCP constructs and (scramble sequence) controls. B: Effects of RCP overexpression and inhibition on anchorage-independent colony formation in soft agar. C-D: Effects of RCP overexpression and inhibition on (E) cell invasion through matrigel, and (F) cell migration. All error bars computed from mean+/−s.d. *, p<0.05, , p<0.01 and *, p<0.001, Student's t-test (two-tailed).

To further evaluate the effects of RCP, the inventors took advantage of the stringent requirement of MCF10A cells for serum and supplemental growth factors to support their proliferation. The stable lines were maintained both in the presence and absence of growth factors. MCF10A-RCP cells showed significant increased rate of proliferation in both culture conditions than control cells (FIG. 6D and FIG. 8A). Most interestingly, in the most stringent medium of 1% FBS without supplemented growth factors (EGF, insulin), the control lines died within 6 days, while MCF10A-RCP cells could be maintained for over a month indicating a RCP-mediated loss of growth factor dependence (FIG. 6D). The cell cycle analysis by propidium iodide staining revealed that after 48 hr of serum and growth factor starvation, 93% of the control cells had arrested at G1 phase compared to only 3% of the cells at G2M stage, whereas in MCF10A-RCP cells, about 80% of cells were at G1 phase and 12% of cells were in G2M stage, confirming the role of RCP in regulating cell cycle progression (FIG. 7A).

Figure 8B:
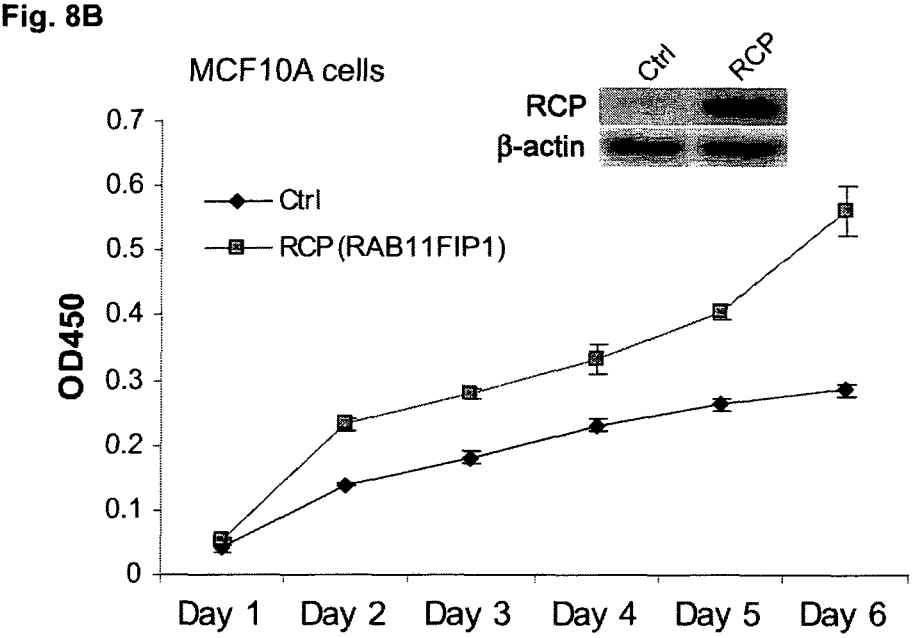

Next, the capacity of RCP to drive anchorage-independent growth in MCF10A cells in soft agar colony formation assays was examined. As expected, the control cells failed to produce colonies in soft agar. In marked contrast, however, MCF10A-RCP cells formed numerous colonies after 4 weeks, demonstrating that RCP is able to induce a transformed phenotype (FIG. 6E and FIG. 8B). Additionally, we observed that RCP overexpression enhanced the migratory potential of MCF10A cells as demonstrated by wound-healing assays (FIG. 6F) and transwell assays (FIG. 8D).

Figure 7B:
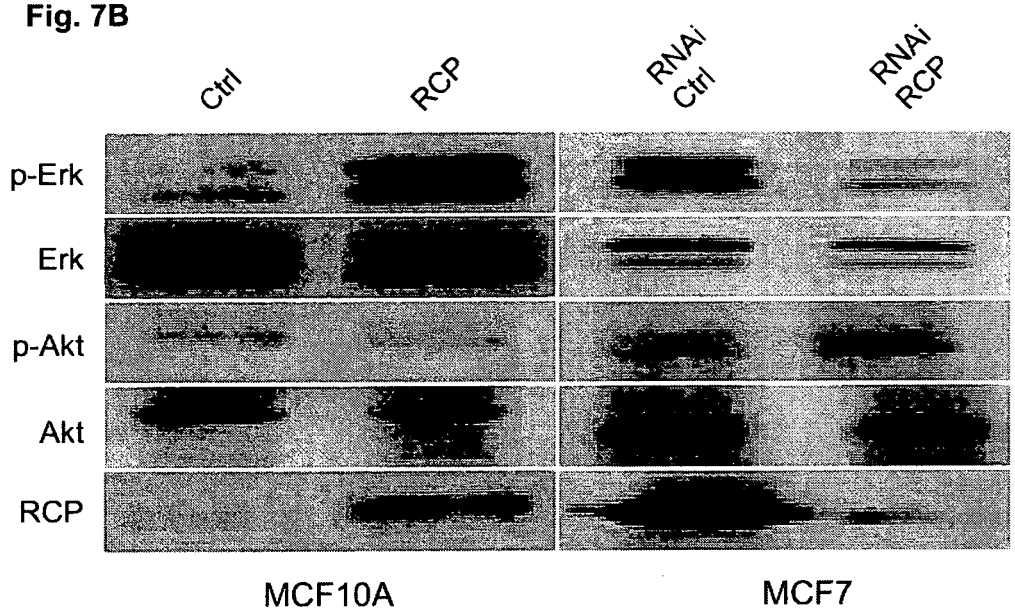
Figure 7C:
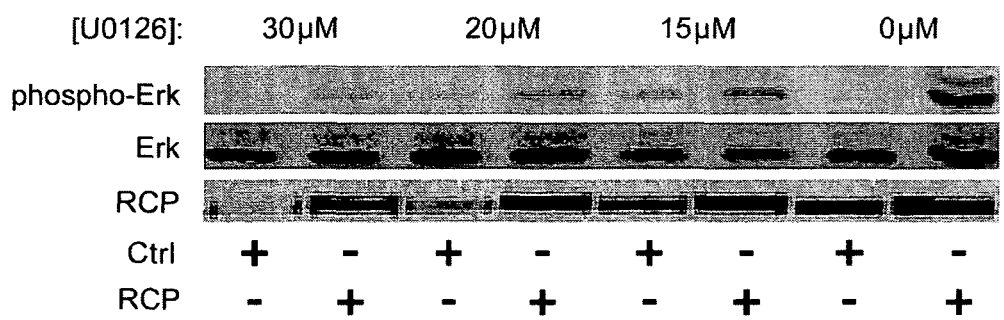
Figure 7D:
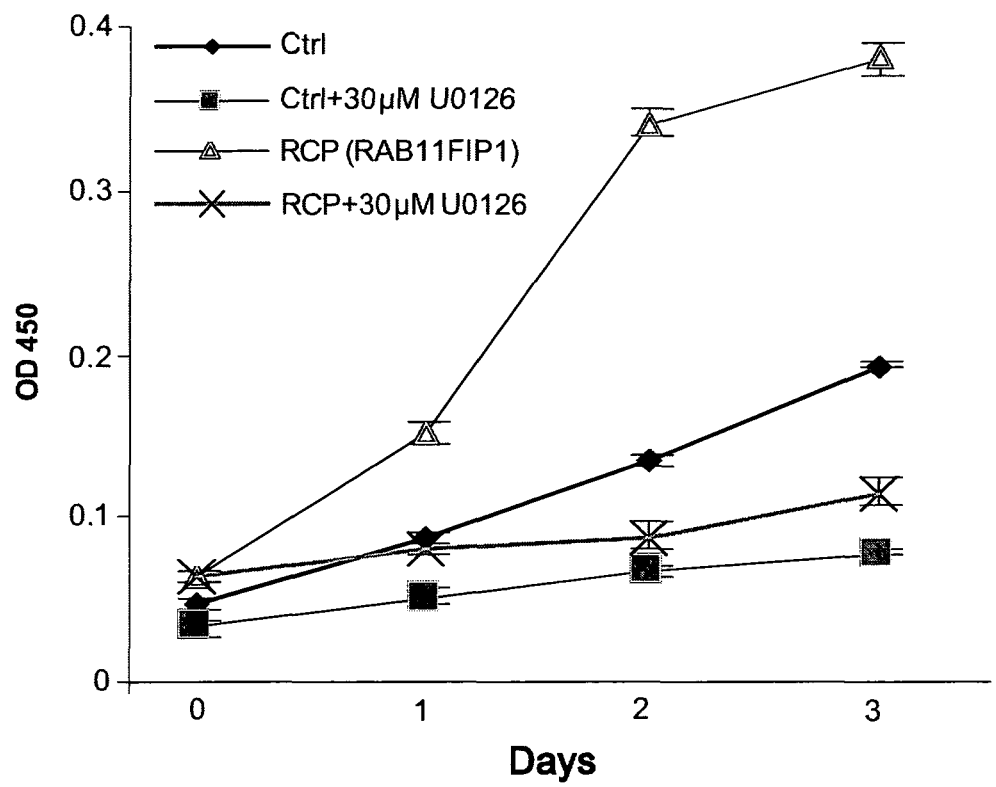

To gain insight into the mechanism(s) by which RCP exerts its oncogenic phenotypes, it was examined whether RCP expression could activate growth signaling through either ERK or AKT, two of the major pathways regulating oncogenic growth. MCF10A-RCP cells displayed strong activation of ERK but not AKT (FIG. 7B). To test whether RCP-induced Erk activation was associated with the proliferative advantage of MCF10A-RCP cells, MCF10A cells were treated with U0126, a potent inhibitor of both active and inactive MEK1/2. While control cells displayed low phosphorylation of ERK across a range of U0126 concentrations, ERK phosphorylation status in MCF10A-RCP cells was concentration dependent (FIG. 7C). At 30 µM of U0126, RCP-induced phosphorylation of ERK was reduced to baseline (same level as control), while RCP levels remained unaltered. Importantly, the MCF10A-RCP cells attenuated for ERK phosphorylation by 30 uM U0126, showed a reduction of proliferation down to control levels (FIG. 7D) despite high RCP expression, suggesting that the RCP proliferation phenotype is dependent on activation of the MAPK pathway via phosphorylation of ERK.

RCP Enhances Tumorigenicity in Multiple Breast Cancer Cell Lines

Figure 8C:
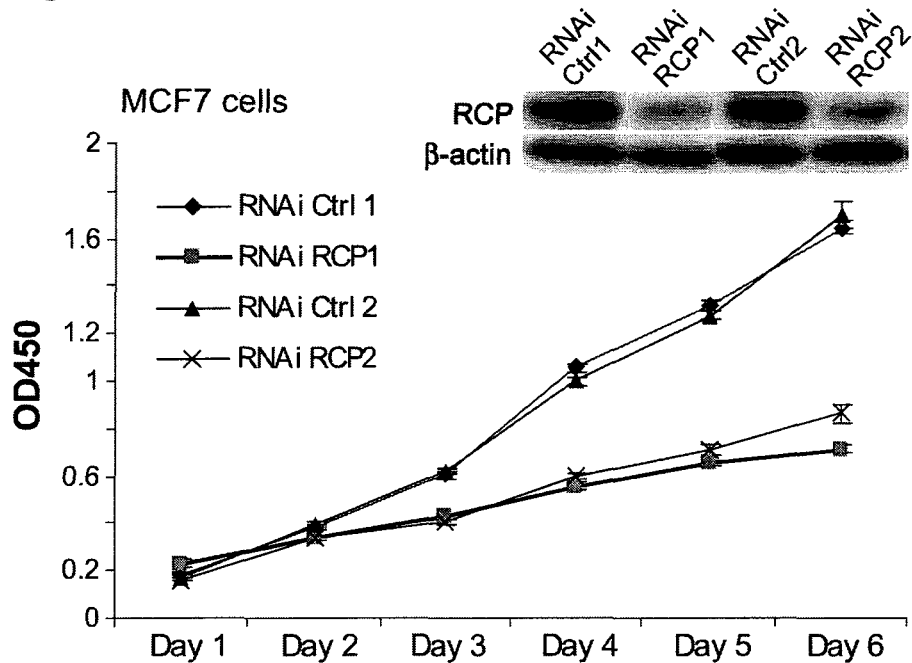
Figure 8D:
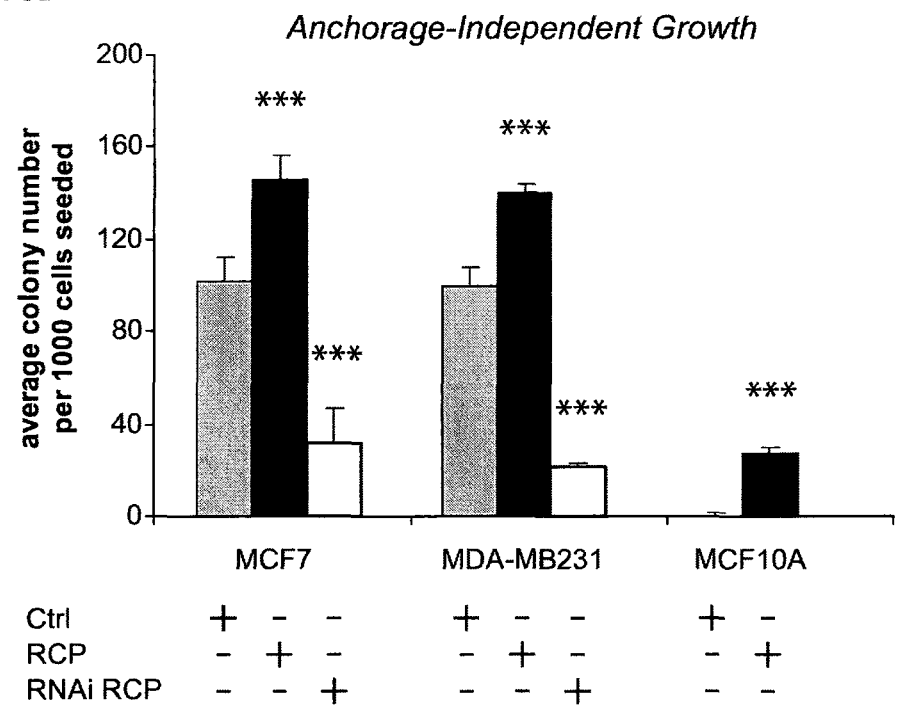
Figure 8E:
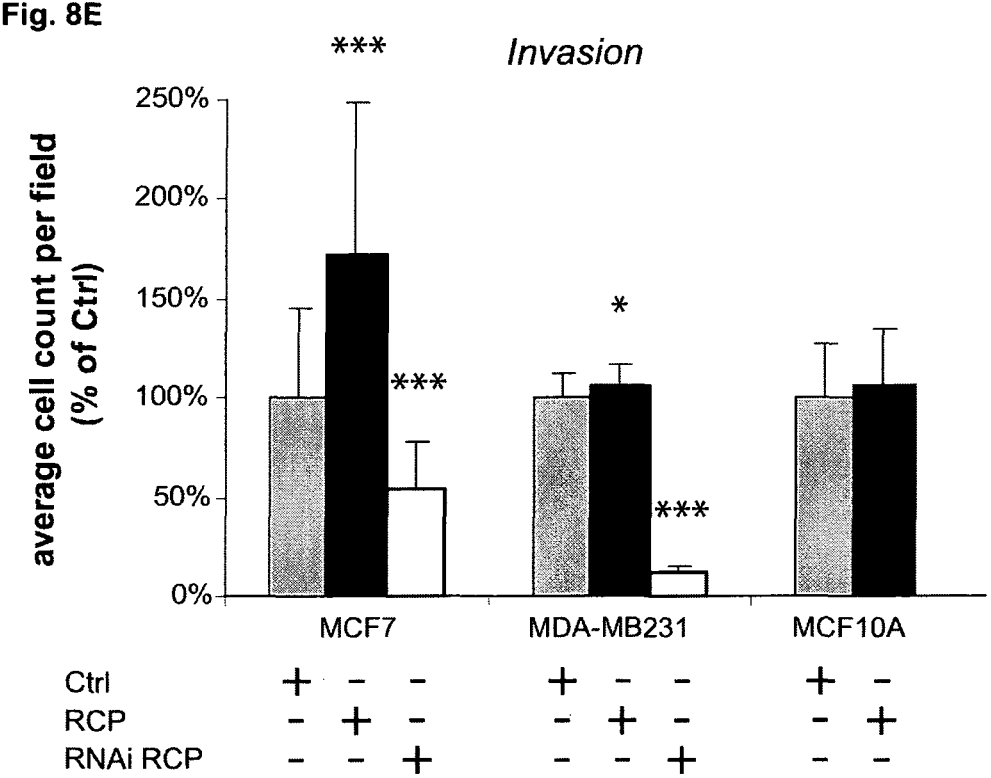
Figure 8F:
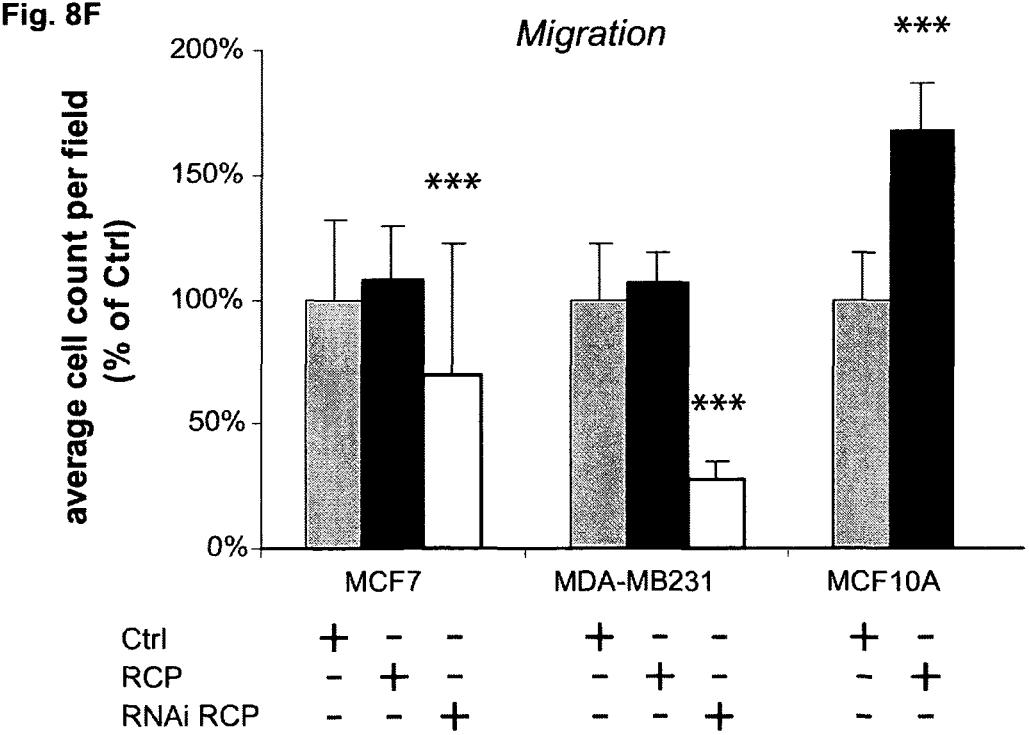

Overexpression of RCP in MCF7 (estrogen receptor-positive, p53-wild type) breast cancer cells moderately increased cell proliferation rate, colony forming activity in soft agar and invasion ability (FIG. 8A-C). In MDA-MB-231 (MB231; estrogen receptor-negative, p53 negative) cells, RCP overexpression increased colony forming activity but not the cell proliferation rate, invasion or migration ability (FIG. 8A-D). To further verify the role of RCP in regulating tumorigenicity, we attenuated the expression of endogenous RCP with RNAi technology. RCP was "knocked down" either by transient transfection with an siRNA construct or by stable transduction of a lentivirus vector expressing an shRNA targeting RCP. RNAi constructs with scrambled sequence were used as controls. Two independent and non-overlapping siRNAs directed against RCP led to a 40-80% reduction in protein levels as well as a significant decrease in cell proliferation in MCF7 cells (FIG. 8A, right panel). Knock down of RCP in MCF7 cells also significantly reduced colony formation in soft agar (FIG. 8B). In MB231 cells, RCP reduction inhibited colony formation but not cell proliferation rate (FIG. 8A,B). In both cell lines, RCP knock down markedly attenuated invasion and migration (FIG. 8C,D). Furthermore, consistent with observations in MCF10A cells, reduction of RCP in MCF7 cells also led to dephosphorylation of ERK (FIG. 7B). Together, these results suggest that expression of endogenous RCP in tumor cells is crucial for maintaining capacity for proliferation, migration and invasion, and the targeted attenuation of RCP function might represent a viable therapeutic strategy.

RCP Knock Down Inhibits Tumor Formation in vivo

Figure 9A:
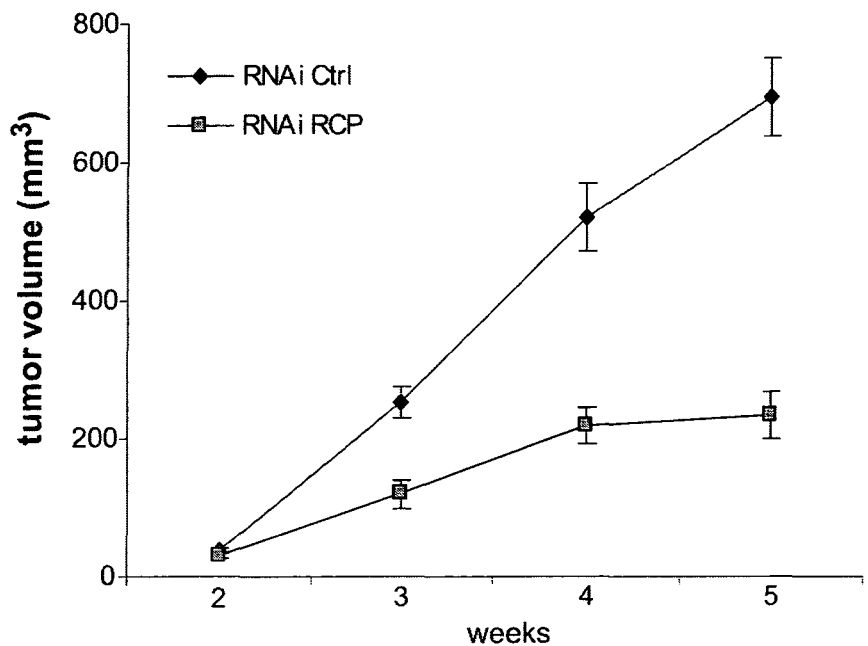
FIGS. 9A and 9D depict average tumor volume plotted as a function of time (mean+/−s.e.m.).
Figure 9B:
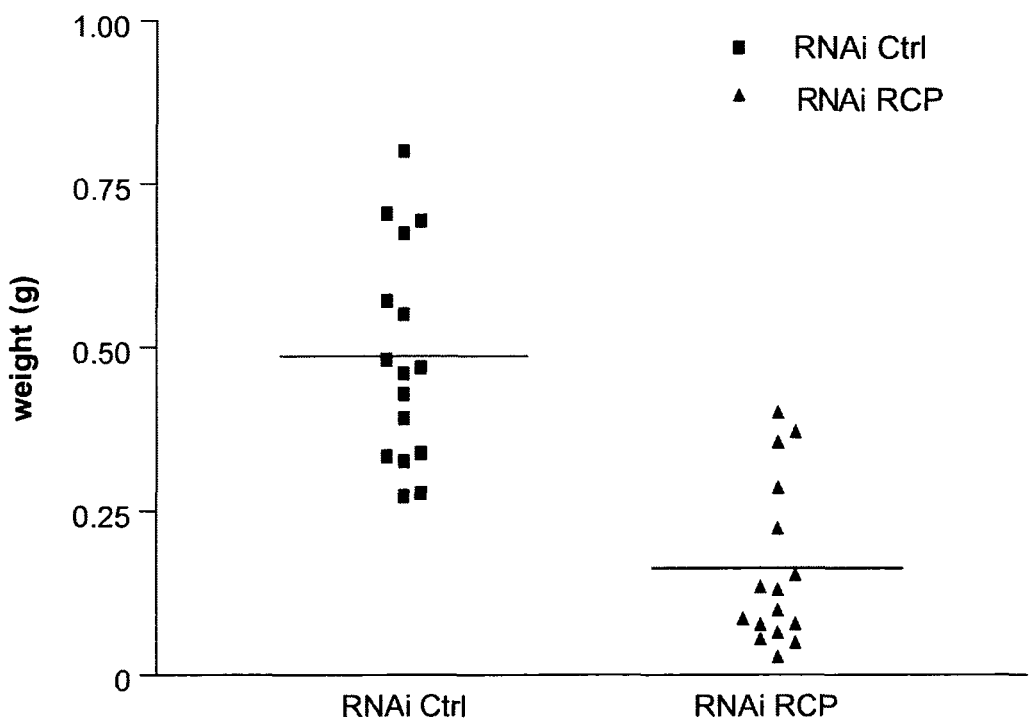
FIGS. 9B and 9E depict tumors plotted by weight at 5 weeks (MCF7) and 7 weeks (MB231); mean weight indicated by solid line.
Figure 9C:
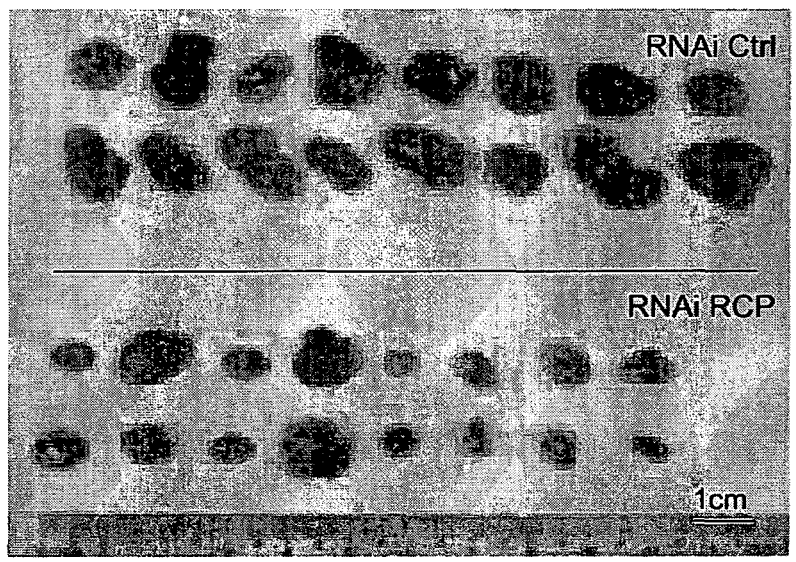
In FIGS. 9C and 9F resected whole tumors are shown.
Figure 9D:
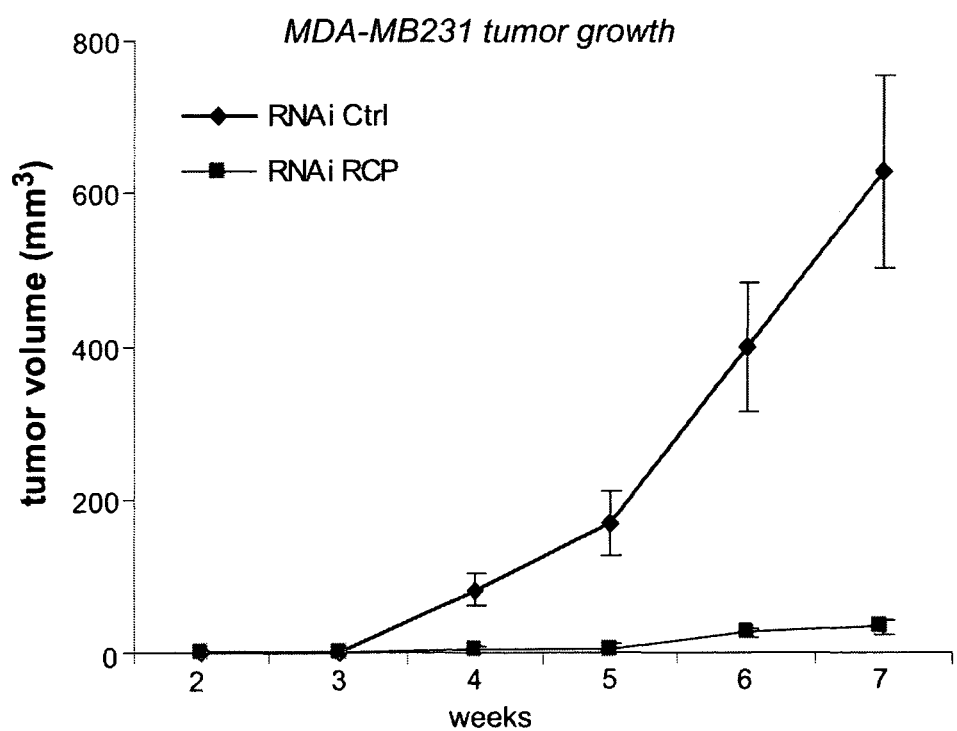
Figure 9E:
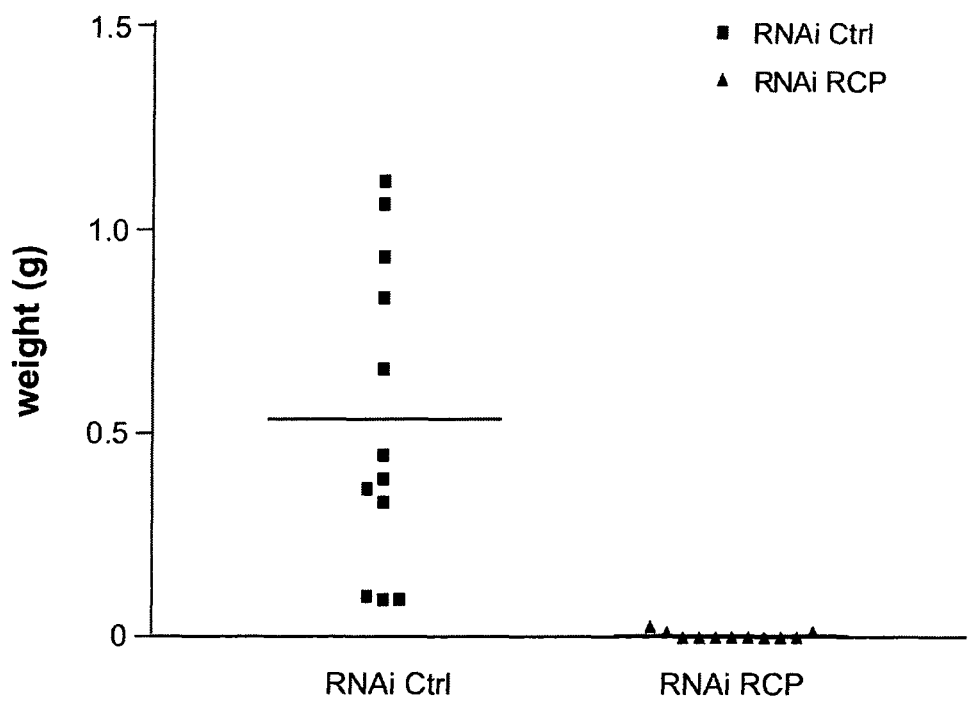
Figure 9F:
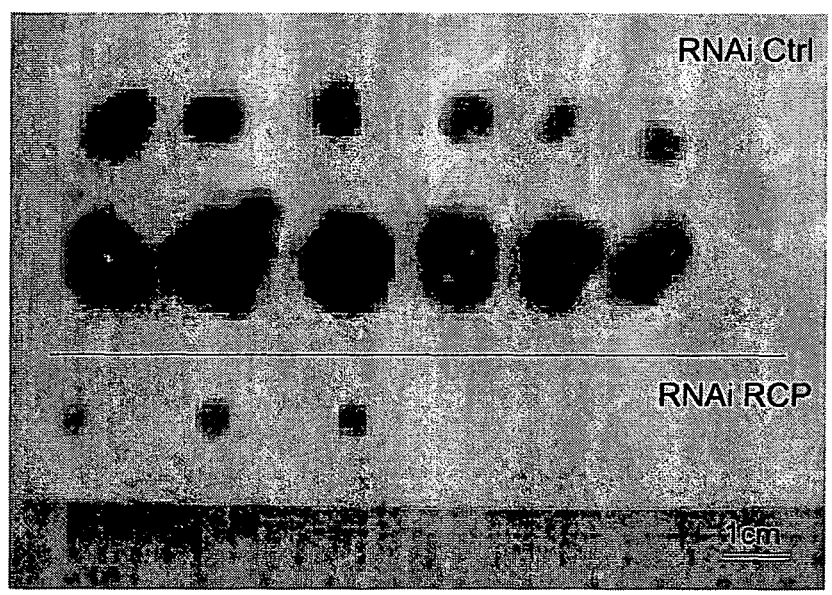

To investigate the effects of RCP attenuation in cancer cells in vivo, we compared the tumor forming abilities of MCF7 and MB231 cells stably expressing shRNA against RCP (RNAi RCP) to that of controls (RNAi Ctrl) in nude mice. Each cell type was implanted subcutaneously above the left and right hind legs of 8 mice. MCF7 is an estrogen-dependent cell line which forms moderately malignant tumors in nude mice in the presence of supplemental estrogen. While all estrogen-supplemented mice implanted with MCF7-RNAi Ctrl (n=8) or MCF7-RNAi RCP (n=8) developed overt tumors, the RCP-inhibited cells developed significantly smaller sized tumors (P=0.00007; Student's t-test) (FIG. 9A, FIG. 9B, FIG. 9C). MB231, on the other hand, is an estrogen-independent breast cancer cell line that forms highly malignant and metastatic tumors in nude mice. All of the mice injected with MB231-RNAi Ctrl cells developed large tumors, however, only 2 of 8 mice injected with MB231-RNAi RCP cells developed tumors (i.e, 2 tumors in one mouse and 1 tumor in another) (FIG. 9D, FIG. 9E, FIG. 9F). Notably, these tumors were much smaller than that of the control mice, the average weight being only 1% of the controls. The knock down of RCP in these tumors was verified by immunohistochemistry (FIG. 9G).

The fact that RCP knock down in MB231 cells had no effect on proliferation in vitro suggests that the strong anti-tumor effects observed for RCP inhibition in vivo may be related to induction of cell death under serum deprivation, given that tumor vascularization of the subcutaneous implant takes several days to manifest. Accordingly, we investigated the sensitivity of the MB231 stable cell lines to cell death and apoptosis under different culture conditions. In complete medium, the MB231-RNAi RCP and control lines showed no difference in cell death as evidenced by very few apoptotic cells in either line. Under serum-starved conditions, however, the controls remained resistant to cell death while the RNAi RCP cells did not. Significantly more RCP-attenuated cells died as a consequence of serum starvation, among which, apoptosis could be detected in ~13% (FIG. 9H). This suggests that RCP reduction enhances the vulnerability of MB231 cells to a poor nutrient environment, which may explain the dramatic anti-tumor effect of RCP knockdown in vivo. Intriguingly, we did not observe an increase in tumorigenicity associated with RCP overexpression in vivo (data not shown), perhaps reflecting a maximal pathological effect on tumor formation achieved by endogenous levels of RCP. Overall, the results indicate that the targeted knock down of RCP suppresses the in vivo growth of both estrogen-dependent and independent breast tumors, and implicates RCP as a potentially valuable new target for therapeutic intervention.

Discussion

Genome-wide microarray analysis of primary tumors has enabled the discovery of novel, clinically-relevant tumor subtypes defined by unique patterns of gene expression. More recently, however, the inverse of this concept has been explored through bottom-up analytical strategies that seek to identify gene subtypes with functional roles in tumorigenesis. These strategies probe the conditional relationships between gene expression and clinical and genomic features of cancer. Adler and colleagues used a genetic linkage approach (stepwise linkage analysis of microarray signatures) to uncover transcriptional mechanisms driving the expression of a prognostic "wound signature" in breast cancer (Adler, A. S., & Chang, H. Y., (2006) *Cell Cycle* 5, 1148-1151). By identifying changes in both copy number and gene expression that were significantly associated with tumors positive or negative for the wound signature, the authors deduced and biochemically verified that MYC (at 8q24) and CSN5 (at 8q13) functionally interact to regulate transcription of the wound response genes. In the present work, we have built on this concept of data integration and functional discovery, and developed a novel correlation-based strategy to deduce genes with mechanistic roles in cancer progression.

The above described approach, termed TRIAGE, combines gene expression characteristics with positional information (genomic location), clinical data (distant metastasis-free survival of patients) and predictive tumor biology (proliferative capacity) to pinpoint over-expressed and survival-correlated genes at sites of recurrent amplification. While TRIAGE does not detect all types of functional oncogenes, by design, it has the potential to resolve those that drive malignant processes contributing to distant metastasis in human patients. TRIAGE is also optimized to discover oncogenes that are activated with high frequency in cancer, as well as those that are associated with resistance to routine therapies. For example, our search for oncogenes is prioritized by the magnitude of principal eigen peaks identified by the LSVD procedure. Since this magnitude is positively related to the frequency of an amplification event, high frequency amplicons (corresponding to high magnitude peaks) are given greater priority. While LSVD allows the robust application of TRIAGE to any comprehensive collection of tumor expression profiles, it has inherent limitations that should be noted. LSVD provides only an approximation of tumors that possess a given amplification event, with poor resolution of the actual amplicon boundaries. Corresponding copy number data, such as that afforded by high-resolution array-CGH, could substantially enhance the performance of TRIAGE by improving the accuracy and precision of amplicon determination.

Additional factors that influence TRIAGE performance include cohort size, duration of patient follow-up, and treatment characteristics—all of which impact candidate gene selection. Our gene-survival associations were calculated using our largest population-based cohort, the Uppsala cohort (n=251 patients), which also has the longest and most complete patient follow-up data. Importantly, the tumors in this collection span a range of aggressive types (FIG. 2), from early-stage (small diameter, lymphnode negative, untreated) to late-stage (large diameter, lymphnode positive, aggressively treated) breast cancer. Thus, this cohort reflects a variety of cancer pathophysiologies presumably driven by a diverse range of oncogenes. The mixed therapeutic background of the patients, however, favors the identification of genes with survival associations independent of therapeutic type. Thus, oncogenes with treatment-dependent or bifunctional survival associations (Andre, F., et al., (2007) *Clin*

Cancer Res 13, 2061-2067) may be unrecognized in this cohort, but potentially identified in others.

LSVD analysis of our integrated breast tumor dataset resulted in the discovery of a large principal eigen peak centered on a group of genes located in a frequently amplified region of 8p11-12. Amplification of this locus has been observed in ~10-25% of breast tumor cases (Adnane, J., et al. (1991) Oncogene 6, 659-663; Garcia, M. J., et al., (2005) Oncogene 24, 5235-5245; Letessier et al., 2006, supra; Theillet, C., et al., (1993) Genes Chromosomes Cancer 7, 219-226), and has been associated with poor patient survival and short interval to distant metastasis in multiple independent studies (Chin et al., 2006, supra; Cuny, M., et al., (2000) Cancer Res 60, 1077-1083; Gelsi-Boyer, V., et al., (2005) Mol Cancer Res 3, 655-667; Letessier et al., 2006, supra). Recently, this amplicon has been the focus of several intensive functional genomics investigations involving primary breast tumors and cell lines (Garcia et al., 2005, supra; Gelsi-Boyer et al., 2005, supra; Ray et al., 2004, supra). Using a high-resolution BAC microarray specific for chromosome 8p, Gelsi-Boyer and colleagues (2005, supra) determine that the 8p11-12 amplicon actually comprises of four well demarcated sub-amplicons, termed A1, A2, A3 and A4, with minimal overlap. The authors of this and other studies have proposed a number of candidate oncogenes in this region based on strong correlations between gene amplification and mRNA overexpression (Garcia et al., 2005, supra; Gelsi-Boyer et al., 2005, supra; Ray et al., 2004, supra). Cummulatively, these studies have identified ZNF703 (FLJ14299), ERLIN2 (SPFH2), PROSC, BRF2, RAB11FIP1 (RCP), and LSM1 as having the strongest correlations between amplification and overexpression, with all but LSM1 localizing to a 1-Mb "minimal amplicon" (Garcia et al., 2005, supra) and overlapping precisely with the A1 sub-amplicon (Gelsi-Boyer et al., 2005, supra). Notably, the genes identified by LSVD in our study specifically comprise the A1 and A2 sub-amplicons and thus include all the "best candidate" oncogenes described by these earlier studies.

Application of TRIAGE to 8p11-12 resulted in the identification of RAB11FIP1 (RCP) as the strongest candidate oncogene at this amplicon, potentially driving metastaticdissemination in patients. Of the other candidate oncogenes in this region previously shown to possess some transforming properties in breast epithelial cells (Streicher, K. L., et al., (2007) Oncogene 26, 2104-2114; Yang, Z. Q., et al., (2006) Cancer Res 66, 11632-11643), LSM1, BAG4 and C8orf4 (TC1) all reside primarily on the A2 and A3 sub-amplicons (Gelsi-Boyer et al., 2005, supra). RAB11FIP1 (RCP), in contrast, is located closer to the core of the A1 amplicon on the 1-Mb minimal amplicon (Garcia et al., 2005, supra), and is the first in this region to be functionally characterized as an oncogene.

Using their novel approach, the inventors have discovered a broad range of cancer-promoting effects linked to RCP expression. In noncancerous breast epithelial cells, RCP overexpression led to malignant transformation, and increased cell motility and migration. In breast cancer cell lines, attenuation of endogenous RCP by RNA inhibition reduced proliferation, anchorage-independent growth, invasion and apoptotic resistance, and diminished tumor formation in nude mice. Physiologically, RCP is thought to interact primarily with Rab11 to regulate protein sorting in tubular endosomes (Peden et al., 2004, supra). Rab11-RCP complexes have been shown to channel transferrin receptor away from lysosomes (the degradation pathway) to recycling endosomes (the recycling pathway), thereby promoting a relative increase in the level of membrane-bound receptor (Peden et al., 2004, supra). Though speculative, it is plausible that the transforming effects of RCP may be mediated by this shift towards the recycling pathway, prolonging the membrane localization (and thus function) of certain membrane proteins such as the integrins or growth factor receptors with oncogenic roles. The strong correlation we observed between RCP expression and ERK phosphorylation may reflect this possibility, as it may indicate a specific link between RCP and growth factor receptor-mediated MAPK activation. The above data indicate that RAB11FIP1 may represent a key driving force behind the recurrent selection of the 8p11-12 amplicon, and functionally contribute to the metastatic spread of breast cancer which is associated with this amplified region and the expression of RAB11FIP1 itself. That this amplicon has also been observed with frequency in other solid tumors including non-small cell lung carcinomas (Balsara, B. R., et al., (1997) Cancer Res 57, 2116-2120), colorectal cancer (Nakao, K., et al., (2004) Carcinogenesis 25, 1345-1357), and tumors of the urinary bladder (Simon, R., et al. (2001) Cancer Res 61, 4514-4519) and fallopian tube (Snijders, A. M., et al., (2003) Oncogene 22, 4281-4286) suggests that RAB11FIP1 acting alone, or in synergy with neighboring oncogenes, may represent a ubiquitous path to cancer progression.

The listing or discussion of a previously published document in this specification should not necessarily be taken as an acknowledgement that the document is part of the state of the art or is common general knowledge.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" etc. shall be read expansively and without limitation, and are not limited to only the listed components they directly reference, but include also other non-specified components or elements. As such they may be exchanged with each other. Additionally, the terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of diagnosing the risk of developing a neoplasm in a subject, the method comprising:
   determining at least one of an expression level, an activity level and a subcellular localisation of a Rab binding protein; and
   comparing the results of the expression level, the activity level and the subcellular localization of a Rab binding protein with results of a customary control level, wherein an increase above the customary control level indicates that the subject suffers from or is at risk of developing a neoplasm, and wherein the Rab binding protein is a Rab11FIP protein.

2. The method of claim 1, wherein the Rab binding protein is a Rab11FIP protein selected from the group consisting of Rab11FIP1, Rab11FIP2, Rab11FIP3 (eferin), Rab11FIP4, Rab11FIP5 (Rip11), and isoforms thereof.

3. The method of claim 1, wherein said neoplasm is a tumor.

4. The method of claim 3, wherein said tumor is one of a breast tumor, a lung tumor, a colorectal tumor, a tumor of the urinary bladder and a tumor of the fallopian tube.

5. The method of claim 3, wherein said tumor is cancer.

6. The method of claim 1, wherein determining at least one of the expression level, the activity level and the subcellular localisation of a Rab binding protein is carried out in a sample from the subject.

7. The method of claim 1, wherein the increased expression or the increased activity of the Rab binding protein Rab11FIP is an indication that a respective neoplasm will be sensitive to an alteration of intracellular calcium levels.

8. The method of claim 7, wherein the alternation of intracellular calcium levels comprises an increase of intracellular calcium levels achievable by administering a member of the D vitamins, a prodrug of a member of the D vitamins and an analog of a member of the D vitamins.

9. The method of claim 8, wherein the member of the D vitamins is vitamin D3.

* * * * *

```
                              SEQUENCE LISTING

<160> NUMBER OF SEQ ID NOS: 6

<210> SEQ ID NO 1
<211> LENGTH: 24
<212> TYPE: DNA
<213> ORGANISM: artificial sequence
<220> FEATURE:
<223> OTHER INFORMATION: primer

<400> SEQUENCE: 1
accatgtccc taatggtctc ggct                                             24

<210> SEQ ID NO 2
<211> LENGTH: 22
<212> TYPE: DNA
<213> ORGANISM: artificial sequence
<220> FEATURE:
<223> OTHER INFORMATION: primer

<400> SEQUENCE: 2
tgctgattta catctttcct ct                                               22

<210> SEQ ID NO 3
<211> LENGTH: 55
<212> TYPE: DNA
<213> ORGANISM: artificial sequence
<220> FEATURE:
<223> OTHER INFORMATION: oligonucleotide forward, encoding shRNA

<400> SEQUENCE: 3
tcgataagca agaaggagtt ttcaagagaa actccttctt gcttatcgtt ttttc           55

<210> SEQ ID NO 4
<211> LENGTH: 59
<212> TYPE: DNA
<213> ORGANISM: artificial sequence
<220> FEATURE:
<223> OTHER INFORMATION: oligonucleotide reverse, encoding shRNA

<400> SEQUENCE: 4
tcgagaaaaa acgataagca agaaggagtt tctcttgaaa actccttctt gcttatcga       59

<210> SEQ ID NO 5
<211> LENGTH: 55
<212> TYPE: DNA
<213> ORGANISM: artificial sequence
<220> FEATURE:
<223> OTHER INFORMATION: control oligonucleotide forward

<400> SEQUENCE: 5
tgaacggcat caaggtgaac ttcaagagag ttcaccttga tgccgttctt ttttc           55

<210> SEQ ID NO 6
<211> LENGTH: 59
<212> TYPE: DNA
<213> ORGANISM: artificial sequence
<220> FEATURE:
<223> OTHER INFORMATION: control oligonucleotide reverse

<400> SEQUENCE: 6
tcgagaaaaa agaacggcat caaggtgaac tctcttgaag ttcaccttga tgccgttca       59
```